(12) United States Patent
deCharms

(10) Patent No.: US 7,567,693 B2
(45) Date of Patent: *Jul. 28, 2009

(54) METHODS FOR PHYSIOLOGICAL MONITORING TRAINING, EXERCISE AND REGULATION

(76) Inventor: R. Christopher deCharms, 11 Julliana Ave., Moss Beach, CA (US) 94038

(*) Notice: Subject to any disclaimer, the term of this patent is extended or adjusted under 35 U.S.C. 154(b) by 0 days.

This patent is subject to a terminal disclaimer.

(21) Appl. No.: 11/270,064

(22) Filed: Nov. 8, 2005

(65) Prior Publication Data

US 2006/0078183 A1 Apr. 13, 2006

Related U.S. Application Data

(63) Continuation of application No. 10/062,627, filed on Jan. 30, 2002, now Pat. No. 6,996,261.

(60) Provisional application No. 60/265,204, filed on Jan. 30, 2001, provisional application No. 60/265,214, filed on Jan. 30, 2001, provisional application No. 60/350,211, filed on Nov. 2, 2001.

(51) Int. Cl.
*G06K 9/00* (2006.01)
*A61B 6/00* (2006.01)

(52) U.S. Cl. .......................... 382/128; 382/154; 378/4

(58) Field of Classification Search ................ 382/128, 382/129, 130, 131, 132, 133, 154, 155, 170, 382/171, 172, 203, 254, 260, 274, 285, 305, 382/100; 600/410, 417, 544, 558; 424/9.2; 514/214.01; 378/21, 4

See application file for complete search history.

(56) References Cited

U.S. PATENT DOCUMENTS

3,893,450 A 7/1975 Ertl (Continued)

FOREIGN PATENT DOCUMENTS

EP 0512577 11/1992

(Continued)

OTHER PUBLICATIONS

Voyvodic, J. Real-Time tMRI Paradigm Control, Physiology, and Behavior Combine with Near Real-Time Statistical Analysis. NeuroImage. 1999; vol. 10: 91-106.*

(Continued)

*Primary Examiner*—Seyed Azarian
(74) *Attorney, Agent, or Firm*—Wilson Sonsini Goodrich & Rosati

(57) ABSTRACT

Computer executable software and device for guiding brain activity training comprising: logic which takes data corresponding to activity measurements of one or more internal voxels of a brain and determines one or more members of the group consisting of: a) what next stimulus to communicate to the subject, b) what next behavior to instruct the subject to perform, c) when a subject is to be exposed to a next stimulus, d) when the subject is to perform a next behavior, e) one or more activity metrics computed from the measured activity, f) a spatial pattern computed from the measured activity, g) a location of a region of interest computed from the measured activity, h) performance targets that a subject is to achieve computed from the measured activity, i) a performance measure of a subject's success computed from the measured activity, j) a subject's position relative to an activity measurement instrument; and logic for communicating information based on the determinations to the subject in substantially real time relative to when the activity is measured.

34 Claims, 14 Drawing Sheets

U.S. PATENT DOCUMENTS

| | | | |
|---|---|---|---|
| 4,919,143 A | 4/1990 | Ayers | |
| 4,983,917 A | 1/1991 | Le Roux | |
| 4,993,414 A | 2/1991 | Macovski et al. | |
| 5,184,074 A | 2/1993 | Kaufman et al. | |
| 5,190,744 A | 3/1993 | Rocklage et al. | |
| 5,195,524 A | 3/1993 | Takiguchi et al. | |
| 5,215,095 A | 6/1993 | Macvicar | |
| 5,227,725 A | 7/1993 | Cory et al. | |
| 5,243,283 A | 9/1993 | Tokunaga et al. | |
| 5,267,570 A * | 12/1993 | Preston | 600/544 |
| 5,280,793 A | 1/1994 | Rosenfeld | |
| 5,281,916 A | 1/1994 | Hinks et al. | |
| 5,293,879 A | 3/1994 | Vonk et al. | |
| 5,331,969 A | 7/1994 | Silberstein | |
| 5,406,957 A | 4/1995 | Tansey | |
| 5,445,608 A | 8/1995 | Chen et al. | |
| 5,450,855 A | 9/1995 | Rosenfeld | |
| 5,522,863 A | 6/1996 | Spano | |
| 5,531,227 A | 7/1996 | Schneider | |
| 5,603,322 A * | 2/1997 | Jesmanowicz et al. | 600/410 |
| 5,638,826 A | 6/1997 | Wolpaw | |
| 5,674,258 A | 10/1997 | Henschel et al. | |
| 5,716,377 A | 2/1998 | Rise et al. | |
| 5,810,747 A | 9/1998 | Brudny | |
| 5,824,027 A | 10/1998 | Hoffer et al. | |
| 5,844,241 A | 12/1998 | Liu et al. | |
| 5,875,108 A | 2/1999 | Hoffberg | |
| 5,887,074 A | 3/1999 | Lai et al. | |
| 5,899,867 A | 5/1999 | Collura | |
| 5,917,324 A | 6/1999 | Leussler | |
| 5,945,826 A | 8/1999 | Leussler | |
| 5,995,857 A | 11/1999 | Toomim et al. | |
| 6,018,675 A | 1/2000 | Apkarian et al. | |
| 6,042,548 A | 3/2000 | Giuffre | |
| 6,048,359 A | 4/2000 | Biel | |
| 6,066,163 A | 5/2000 | John | |
| 6,097,981 A | 8/2000 | Freer | |
| 6,099,319 A | 8/2000 | Zaltman et al. | |
| 6,161,031 A | 12/2000 | Hochman | |
| 6,169,398 B1 | 1/2001 | Watanabe et al. | |
| 6,234,979 B1 | 5/2001 | Merzenich | |
| 6,275,723 B1 * | 8/2001 | Ferris et al. | 600/417 |
| 6,289,232 B1 | 9/2001 | Jakob et al. | |
| 6,321,105 B1 | 11/2001 | Jenkins et al. | |
| 6,356,781 B1 | 3/2002 | Lee et al. | |
| 6,370,416 B1 * | 4/2002 | Rosenfeld | 600/410 |
| 6,374,140 B1 | 4/2002 | Rise | |
| 6,377,833 B1 | 4/2002 | Albert | |
| 6,391,871 B1 * | 5/2002 | Olney et al. | 514/214.01 |
| 6,402,520 B1 | 6/2002 | Freer | |
| 6,463,315 B1 * | 10/2002 | Klingberg et al. | 600/410 |
| 6,477,399 B2 * | 11/2002 | Biswal et al. | 600/410 |
| 6,517,812 B1 * | 2/2003 | Breiter et al. | 424/9.2 |
| 6,539,246 B2 | 3/2003 | Heid | |
| 6,539,263 B1 | 3/2003 | Schiff | |
| 6,597,937 B2 | 7/2003 | Liu et al. | |
| 6,687,525 B2 | 2/2004 | Llinas et al. | |
| 6,711,430 B1 | 3/2004 | Ferris et al. | |
| 6,907,280 B2 | 6/2005 | Becerra et al. | |
| 6,921,413 B2 | 7/2005 | Mahadevan-Jansen et al. | |
| 6,925,328 B2 | 8/2005 | Foster et al. | |
| 6,996,261 B2 | 2/2006 | Decharms | |
| 7,211,050 B1 * | 5/2007 | Caplygin | 600/558 |
| 7,338,455 B2 | 3/2008 | White et al. | |
| 2001/0056231 A1 | 12/2001 | Jesmanowicz et al. | |
| 2002/0019364 A1 | 2/2002 | Renshaw | |
| 2002/0042563 A1 | 4/2002 | Becerra et al. | |
| 2002/0055675 A1 | 5/2002 | Llinas et al. | |
| 2002/0058867 A1 | 5/2002 | Breiter et al. | |
| 2002/0103428 A1 | 8/2002 | deCharms | |
| 2002/0103429 A1 | 8/2002 | deCharms | |
| 2002/0183817 A1 | 12/2002 | Van Venrooij et al. | |
| 2003/0144709 A1 | 7/2003 | Zabara et al. | |
| 2003/0181960 A1 | 9/2003 | Carter et al. | |
| 2003/0208245 A1 | 11/2003 | Mahadevan-Jansen et al. | |
| 2003/0225326 A1 | 12/2003 | Querleux et al. | |
| 2003/0229107 A1 | 12/2003 | Cowan et al. | |
| 2004/0013291 A1 | 1/2004 | Hillman | |
| 2004/0092809 A1 | 5/2004 | deCharms | |
| 2004/0096395 A1 | 5/2004 | Xiong et al. | |
| 2004/0214790 A1 | 10/2004 | Borgens | |
| 2004/0215286 A1 | 10/2004 | Stypulkowski | |
| 2005/0033154 A1 | 2/2005 | deCharms | |
| 2005/0053550 A1 | 3/2005 | Paskavitz et al. | |
| 2005/0079636 A1 | 4/2005 | White et al. | |
| 2005/0154290 A1 | 7/2005 | Langleben | |
| 2005/0283053 A1 | 12/2005 | deCharms | |
| 2006/0155348 A1 | 7/2006 | deCharms | |
| 2007/0191704 A1 | 8/2007 | deCharms | |
| 2008/0001600 A1 | 1/2008 | de Charms | |

FOREIGN PATENT DOCUMENTS

| | | |
|---|---|---|
| EP | 1128188 | 8/2001 |
| GB | 221759 | 9/1924 |
| WO | WO 97/10747 | 3/1997 |
| WO | WO 97/26823 | 7/1997 |
| WO | WO 97/33515 A1 | 9/1997 |
| WO | WO 99/63355 | 12/1999 |
| WO | WO 02/061457 | 8/2002 |

OTHER PUBLICATIONS

Arfanakis, et al. Combining Independent Component Analysis' and Correlation Analysis to Probe Interregional Connectivity in fMRI Task Activation Datasets. Magnetic Resonance Imaging. 2000; 18 (8): 921-930.

Bock, et al. Pulsewave Velocity Measurement Using a New Real-Time MR-Method. Magnetic Resonance Imaging. 1995; vol. 13 (1): 21-29.

D'Esposito, et al. A Functional MRI Study of Mental Image Generation. Neuropsychologia. 1997; vol. 35, No. 5: 725-730.

Downing, et al. Testing Cognitive Models of Visual Attention with fMRI and MEG. Neuropsychologia. 2001; vol. 39: 1329-1342.

Fong, et al. Event-Related fMRI Reveals Distinct Neural Correlates of Reward Anticipation versus Feedback. NeuroImage. 2001; vol. 13, No. 6, Part 2 of 2 Parts.

Fernandez, et al. Language Mapping in Less Than 15 Minutes: Real-Time Functional MRI during Routine Clinical Investigation. NeuroImage. 2001; vol. 14: 585-594.

Kotchoubey et al. A New Method For Self-Regulation of Slow Cortical Potentials in a Timed Paradigm. Applied Psychophysiology and Biofeedback. 1997; vol. 22, No. 2: 77-93.

Ngan, et al. Activation Detection in Event-Related fMRI Data based on Spatio-Temporal Properties. Magnetic Resonance Imaging. 2001; vol. 19, No. 9: 1149-1158.

Pantel, et al. Quantitative Magnetic Resonance Imaging and Neuropsychological Functions in Dementia of the Alzheimer type. Psychological Medicine. 1997; vol. 27: 221-229.

Paus, Tomáš. Imaging the Brain Before, During, and After Transcranial Magnetic Stimulation. Neuropsychologia. 1999; vol. 37: 219-224.

Schröder, et al. Motor Dysfunction and Sensorimotor Cortex Activation Changes in Schizophrenia: A Study with Functional Magnetic Resonance Imaging. NeuroImage. 1999; vol. 9: 81-87.

Siniatchkin, et al. Neurofeedback The Significance of Reinforcement and the Search for an Appropriate Strategy for the Success of Self-regulation. Applied Psychophysiology and Biofeedback. 1998; vol. 25, No. 3: 167-175.

Thompson, et al. Neurofeedback Combined with Training in Metacognitive Strategies: Effectiveness in Students with ADD. Applied Psychophysiology and Biofeedback. 1998; vol. 23, No. 4: 243-263.

Voyvodic, J. Real-Time fMRI Paradigm Control, Physiology, and Behavior Combine with Near Real-Time Statistical Analysis. NeuroImage. 1999; vol. 10: 91-106.

Wilding, Edward L. Event-Related Functional Imaging and Episodic Memory. Neuroscience & Biobehavioral Reviews. 2001; vol. 25: 545-554.

Yoo, et al. Real-Time Adaptive Functional MRI. NeuroImage. 1999; vol. 10: 596-606.

Zacks, et al. Imagined Transformations of Bodies: An fMRI Investigation. Neuropsychologia. 1999; vol. 37: 1029-1040.

Toni, et al. The Time Course of Changes during Motor Sequence Learning: A Whole-Brain fMRI Study. Neuroimage. 1998; vol. 8: 50-61.

"Virtual Retinal Display (VRD) Technology", presented in www.cs.nps.navy.mil/people/faculty/capps/4473/projects/fiambolis/vrd/vrd_full.html. Accessed Jan. 27, 2006.

Allegre, G. et al. Stimulation in the rat of a nerve fiber bundle by a short UV pulse from an excimer laser. Neuroscience Letters. 1994; 180(2): 261-4 (Abstract).

Capecci, M. et al. Chronic Bilateral Subthalamic Deep Brain Stimulation in a Patient with Homozygous Deletion in the Parkin Gene. Movements Disorders. 2004; vol. 19(12): 1450-1452.

Cuschieri, A. Laparoscopic surgery: current status, issues and future developments. Surgeon. 2005; 3(3):125-30, 132-3, 135-8. (Abstract).

deCharms, et al. Control over brain activation and pain learned by using real-time functional MRI. Proc Natl Acad Sci U S A. 2005; 102(51):18626-31.

deCharms, et al. Learned regulation of spatially localized brain activation using real-time fMRI. Neuroimage. 2004; 21(1):436-43.

Edwards, G. et al. Tissue ablation by a free-electron laser tuned to the amide II band. Nature. 1994: 371(6496): 416-9, 1994. (Abstract).

Kuncel, A. M., et al. Selection of Stimulus Parameters for Deep Brain Stimulation. Clinical Neurophysiology. 2004; 115: 2431-2441.

Van Horne, C.G. et al. Multichannel semiconductor-based electrodes for in vivo electrochemical and electrophysiological studies in rat CNS. Neuroscience Letters. 1990; 120 (2): 249-252. (Abstract).

Sachs, H. G. et al. Retinal Replacement—the Development of Microelectronic Retinal Prostheses—Experience with Subretinal Implants and New Aspects. Graefe's Arch Clin Exp Ophthalmol. 2004: 242: 717-723.

Schachter, S. C. Vagus nerve stimulation: current status and clinical applications. Expert Opin Investig Drugs. 1997; 6(10): 1327-35. (Abstract).

Schmitz, D. et al. Synaptic activation of presynaptic kainate receptors on hippocampal mossy fiber synapses. Neuron. 2000; 27(2): 327-338. (Abstract).

Simpson, K. H. et al. A Randomized, Double-Blind, Crossover Study of the Use of Transcutaneous Spinal Electroanalgesia in Patients with Pain from Chronic Critical Limb Ischemia. Journal of Pain and Symptom Management. 2004; vol. 28(5): 511-516.

Turner, J. A. et al. Spinal Cord Stimulation for Patients With Failed Back Surgery Syndrome or Complex regional Pain Syndrome: A Systematic Review of Effectiveness and Complications. Pain. 2004; 108: 137-147.

Viirre, E. et al. The virtual retinal display: a new technology for virtual reality and augmented vision in medicine. Stud Health Technol Inform. 1998; 50:252-7.

Richard Christopher deCharms. U.S. Appl. No. 11/678,386, entitled "Methods for measurement of magnetic resonance signal perturbations," filed Feb. 23, 2007.

Examination report for EP 02706085.4 dated Nov. 20, 2008.

Richard Christopher de Charms. U.S. Appl. No. 60/399,055 entitled "Methods for measurement and analysis of brain activity," filed Jul. 26, 2002.

Cox, et al. Real-time functional magnetic resonance imaging. Magn Reson Med. 1995; 33(2): 230-6.

deCharms, et al. Neural representation and the cortical code. Annu Rev Neurosci. 2000; 23:613-647.

Gembris, et al. Functional magnetic resonance imaging in real time (FIRE): sliding-window correlation analysis and reference-vector optimization. Magn Reson Med. 2000; 43(2): 259-68.

Kwong, et al. Dynamic magnetic resonance imaging of human brain activity during primary sensory stimulation. Proc Natl Acad Sci USA. 1992; 89(12): 5675-9.

Posse, et al. A new approach to measure single-event related brain activity using real-time fMRI: feasibility of sensory, motor, and higher cognitive tasks. Hum Brain Mapp. 2001; 12(1): 25-41.

Yoo, et al. Functional MRI for neurofeedback: feasibility study on a hand motor task. Neuroreport. 2002; 13(11): 1377-81.

* cited by examiner

FIGURE 2

FOREBRAIN
Diencephalon
  Subthalamus
    Zona incerta
    Subthalamic nucleus
  Hypothalamus
    Intermediate hypothalamic region
    Hypophysis
      Adenohypophysis
      Neurohypophysis
  Thalamus (including all sub-
    divisions)
  Metathalamus
    Medial geniculate body
    Lateral geniculate body
  Epithalamus
    Habenula
    Pineal body
Telencephalon
  Cerebral cortex including all 47
  areas as described by Brodmann
  Archicortex
    Hippocampal formation
      Hippocampus
      Dentate gyrus
      Subiculum
    Parahippocampal gyrus
    Cingulate gyrus
  Occipital lobe
  Temporal lobe
  Insula
  Parietal lobe
  Frontal lobe
  Cerebral white matter
    Anterior commissure
    Internal capsule
    Corpus callosum
  Basal ganglia
    Amygdala
    Globus pallidus
    Striatum
    Substantia Nigra
    (pars compacta and pars
      reticulata)
    Caudate nucleus
    Putamen
  Septum
  Fornix
  Olfactory bulb
MIDBRAIN
  Cerebral Peduncle
  Substantia nigra
  Midbrain tegmentum
    Midbrain reticular formation
    Red nucleus
    Oculomotor nuclei
  Tectum
    Inferior colliculus
    Superior colliculus
    Pretectal region
HINDBRAIN
  Medulla oblongata
    Cochlear nuclei
    Medullary reticular formation
    Solitary nucleus
    Inferior olivary complex
    Vestibular nuclei
  Metencephalon
    Cerebellum
      Deep cerebellar nuclei
        Dentate nucleus
        Fastigial nucleus
        Globose nucleus
        Emboliform nucleus
      Cerebellar cortex
        Flocculonodular lobe
        Posterior lobe
          Vermis of posterior lobe
        Anterior lobe
  Pons
    Basal part of pons
    Pontine nuclei
    Pontine tegmentum
    Pontine reticular formation
    Superior olivary complex
    Locus ceruleus A more complete list is available in cited neuroanatomical texts.

FIGURE 3

Alzheimer's Disease
Amyotrophic Lateral Sclerosis
Anxiety Disorders
Aphasia
Apraxia
Asperger Syndrome
Attention Deficit-Hyperactivity Disorder
Autism
Autonomic Dysfunction
Back Pain
Bell's Palsy
Bipolar Disorder
Brain and Spinal Tumors
Brain Aneurysm
Brain Injury
Carpal Tunnel Syndrome
Causalgia
Central Pain
Cerebral Aneurysm
Cerebral Arteriosclerosis
Cerebral Palsy
Charcot-Marie-Tooth Disorder
Chiari Malformation
Chorea
Chronic Pain
Chronic Regional Pain Syndrome
Cns Trauma
Cushing's Syndrome
Dandy-Walker Syndrome
Dementia - Multi-Infarct
Dementia With Lewy Bodies
Depression
Diabetic Neuropathy
Diffuse Sclerosis
Dysgraphia
Dyslexia
Dystonias
Encephalitis and Meningitis
Epilepsy
Epilepsy
Friedreich's Ataxia
Gaucher's Disease
Guillain-Barre Syndrome
Head Injury
Headache
Herpes Zoster
Huntington's Disease
Hydrocephalus
Landau-Kleffner Syndrome
Lateral Medullary Syndrome
Learning Disabilities
Leigh's Disease
Lewy Body Dementia
Lissencephaly
Locked-In Syndrome
Lou Gehrig's Disease
Lupus - Neurological Sequelae
Lyme Disease - Neurological Sequelae
Meningitis
Migraine
Mini-Strokes
Motor Neuron Diseases
Multiple Sclerosis
Muscular Dystrophy (MD)
Myasthenia Gravis
Myoclonus
Myopathy
Myotonia Congenita
Narcolepsy
Neurofibromatosis
Neurological Manifestations of AIDS
Neuronal Migration Disorders
Niemann-Pick Disease
Obesity
Occipital Neuralgia
Overuse Syndrome
Pain - Chronic
Paresthesia
Parkinson's Disease
Parkinson's Disease
Parmyotonia Congenita
Parry Romberg
Peripheral Neuropathy
Pervasive Developmental Disorders
Pick's Disease
Pinched Nerve
Pituitary Tumors
Postherpetic Neuralgia
Repetitive Motion Disorders
Repetitive Stress Injuries
Restless Legs Syndrome
Rett Syndrome
Schizophrenia
Seizure Disorder
Shingles
Sleep Apnea
Sleep Disorders
Spasticity
Spina Bifida
Spinal Cord Injury
Spinal Cord Tumors
Stroke
Sturge-Weber Syndrome
Tardive Dyskinesia
Tay-Sachs Disease
Temporal Arteritis
Tic Douloureux
Tourette Syndrome
Traumatic Brain Injury
Tremor
Trigeminal Neuralgia
Wallenberg's Syndrome
Zellweger Syndrome

FIGURE 14

| Region | Coords. | Condition | Neuro-modulator |
|---|---|---|---|
| subthalamic nucleus | X=+-10 Y=-13 Z=-4 | PD | - |
| substantia nigra | X=+-10 Y=-17 Z=-8 | PD,Schz | DA |
| thalamic nucleus VA ventro anterior | X=+-10 Y=-5 Z=8 | PD | - |
| nucleus accumbens | X=+-10 Y=7 Z=-8 | SA, Rew, Schz | DA |
| thalamic nucleus VL ventrolateral | X=+-14 Y=-11 Z=8 | PD | - |
| globus pallidus internus | X=+-15 Y=-2 Z=-4 | PD | - |
| pulvinar nucleus | X=+-15 Y=-27 Z=4 | ADD | - |
| thalamic nucleus VP | X=+-17 Y=17 Z=9 | Pain | - |
| locus coeruleus | X=+-2 Y=-31 Z=-14 | ADD, SA, Rew | NA |
| globus pallidus externus | X=+-20 Y=-2 Z=-4 | PD | - |
| amygdala | X=+-22 Y=-5 Z=-12 | Pain | - |
| medial frontal lobe | X=+-3 Y=14 Z=40 | Pain | - |
| periaqueductal gray matter | X=0 Y=-26 Z=-12 | Pain | opiates |
| raphe dorsalis | X=+-2 Y=-30 Z=-12 | Pain | 5-HT |
| nucleus basalis of Meynert | X=+4 Y=1 Z=-12 | AD, learning & plasticity | Ach |
| dorsolateral pre-frontal cortex | X=+-28 Y=34 Z=35 | Dep | - |
| anterior pre-frontal cortex | X=+-17 Y=64 Z=16 | Dep | - |
| rostral ventromedial medulla | X=2 Y=-28 Z=-28 | Pain | opiates |
| nucleus raphe magnus | X=2 Y=-30 Z=-28 | Pain | 5-HT, opiate |
| thalamic nucleus Vim ventrointeromedial | X=+-7 Y=-12 Z=4 | PD | - |
| Brodmann's areas 4 | X=+-48 Y=-15 Z=40 | Motor impairments | - |
| Brodmann's areas 6 | X=59 Y=-9 Z=40 | Motor impairments | - |
| PD - Parkinson's disease; AD - Alzheimer's disease, ADD - attention & attention deficit/attention deficit/hyperactivity disorder, Dep - depression/mood/affect, SA -substance abuse & addiction, Schz - schizophrenia, Rew - reward DA - dopamine, 5-HT - serotonin, Ach - acetyl choline, NA - noradrenaline | | | |

METHODS FOR PHYSIOLOGICAL MONITORING TRAINING, EXERCISE AND REGULATION

RELATED APPLICATION

This application is a continuation of patent application Ser. No. 10/062,627 filed Jan. 30, 2002, now U.S. Pat. No. 6,996,261, claims the benefit of U.S. Provisional Patent Application No. 60/265,204, filed Jan. 30, 2001; U.S. Provisional Patent Application No. 60/265,214, filed Jan. 30, 2001; and U.S. Provisional Patent Application No. 60/350,211, filed Nov. 2, 2001, each of which are incorporated herein in their entirety.

FIELD OF THE INVENTION

The present invention relates to methods, software and systems for monitoring physiological activity, particularly in the human brain and nervous system and therapeutic applications relating thereto.

DESCRIPTION OF RELATED ART

A variety of different brain scanning methodologies have been developed that may be used to identify changes of mental states or conditions including Positron Emission Tomography (PET) and Single Photon Emission Computed Tomography (SPECT), electroencephalogram (EEG) based imaging, magnetoencephalogram (MEG) based imaging, and functional magnetic resonance imaging (fMRI).

For example, magnetic resonance imaging (MRI) has been used successfully to study blood flow in vivo. U.S. Pat. Nos. 4,983,917, 4,993,414, 5,195,524, 5,243,283, 5,281,916, and 5,227,725 provide examples of the techniques that have been employed. These patents are generally related to measuring blood flow with or without the use of a contrast bolus, some of these techniques referred to in the art as MRI angiography. Many such techniques are directed to measuring the signal from moving moieties (e.g., the signal from arterial blood water) in the vascular compartment, not from stationary tissue. Thus, images are based directly on water flowing in the arteries, for example. U.S. Pat. No. 5,184,074, describes a method for the presentation of MRI images to the physician during a scan, or to the subject undergoing MRI scanning.

In the brain, several researchers have studied perfusion by dynamic MR imaging using an intravenous bolus administration of a contrast agent in both humans and animal models (See, A. Villringer et al, Magn. Reson, Med., Vol. 6 (1988), pp 164-174; B. R. Rosen et al, Magn. Reson. Med., Vol. 14 (1999), pp. 249-265; J. W. Belliveau et al, Science, Vol. 254 (1990), page 716). These methods are based on the susceptibility induced signal losses upon the passage of the contrast agent through the microvasculature. Although these methods do not measure perfusion (or cerebral blood flow, CBF) in classical units, they allow for evaluation of the related variable rCBV (relative cerebral blood volume). For example, in U.S. Pat. No. 5,190,744 to Rocklage, quantitative detection of blood flow abnormalities is based on the rate, degree, duration, and magnitude of signal intensity loss which takes place for a region following MR contrast agent administration as measured in a rapid sequence of magnetic resonance images.

With the advent of these brain scanning methodologies, blood flow in various brain areas has been effectively correlated with various brain disorders such as Attention Deficit Disorder (ADD), Schizophrenia, Parkinson's Disease, Dementia, Alzheimers Disease, Endogenous Depression, Oppositional Defiant Disorder, Bipolar Disorder, memory loss, brain trauma, Epilepsy and others.

The prior art also describes a variety of inventions dating back to the 1960's have provided a way allowing subjects to learn to control muscle, autonomic or neural activity through processes. Examples and descriptions are included in U.S. Pat. No. 4,919,143. U.S. Pat. No. 4,919,143, U.S. Pat. No. 5,406,957, U.S. Pat. No. 5,899,867 and U.S. Pat. No. 6,097,981.

Considerable research has also been directed to biological feedback of brainwave signals known as electroencephalogram (EEG) signals. One conventional neurophysiological study established a functional relationship between behavior and bandwidths in the 12-15 Hz range relating to sensorimotor cortex rhythm EEG activity (SMR). Sterman, M. B., Lopresti, R. W., & Fairchild, M. D. (1969). Electroencephalographic and behavioral studies of monomethylhdrazine toxicity in the cat. Technical Report AMRL-TR-69 3, Wright-Patterson Air Force Base, Ohio, Air Systems Command. A cat's ability to maintain muscular calm, explosively execute precise, complex and coordinated sequences of movements and return to a state of calm was studied by monitoring a 14 cycle brainwave. The brainwave was determined to be directly responsible for the suppression of muscular tension and spasm. It was also demonstrated that the cats could be trained to increase the strength of specific brainwave patterns associated with suppression of muscular tension and spasm. Thereafter, when the cats were administered drugs which would induce spasms, the cats that were trained to strengthen their brainwaves were resistent to the drugs.

The 12-15 Hz SMR brainwave band has been used in EEG training for rectifying pathological brain underactivation. In particular the following disorders have been treated using this type of training: epilepsy (as exemplified in M. B. Sterman's, M. B. 1973 work on the "Neurophysiologic and Clinical Studies of Sensorimotor EEG Biofeedback Training: Some Effects on Epilepsy" L. Birk (Ed.), Biofeedback: Behavioral Medicine, New York: Grune and Stratton); Giles de la Tourette's syndrome and muscle tics (as exemplified in the inventor's 1986 work on "A Simple and a Complex Tic (Giles de la Tourette's Syndrome): Their response to EEG Sensorimotor Rhythm Biofeedback Training", International Journal of Psychophysiology, 4, 91-97 (1986)); hyperactivity (described by M. N. Shouse, & J. F. Lubar's in the work entitled "Operant Conditioning of EEG Rhythms and Ritalin in the Treatment of Hyperkinesis", Biofeedback and Self-Regulation, 4, 299-312 (1979); reading disorders (described by M. A. Tansey, & Bruner, R. L.'s in "EMG and EEG Biofeedback Training in the Treatment of a 10-year old Hyperactive Boy with a Developmental Reading Disorder", Biofeedback and Self-Regulation, 8, 25-37 (1983)); learning disabilities related to the finding of consistent patterns for amplitudes of various brainwaves (described in Lubar, Bianchini, Calhoun, Lambert, Brody & Shabsin's work entitled "Spectral Analysis of EEG Differences Between Children with and without Learning Disabilities", Journal of Learning Disabilities, 18, 403-408 (1985)) and; learning disabilities (described by M. A. Tansey in "Brainwave signatures—An Index Reflective of the Brain's Functional Neuroanatomy: Further Findings on the Effect of EEG Sensorimotor Rhythm Biofeedback Training on the Neurologic Precursors of Learning Disabilities", International Journal of Psychophysiology, 3, 85-89 (1985)). In sum, a wide variety of disorders, whose symptomology includes impaired voluntary control of one's own muscles and a lowered cerebral threshold of overload under stress, were found to be treatable by "exercising" the supplementary and sensorimotor areas of the brain using EEG biofeedback.

U.S. Pat. No. 5,995,857 describes an apparatus and method for providing biofeedback of human central nervous system activity using radiation detection. In this patent, radiation from the brain resulting either from an ingested or injected radioactive material or radio frequency excitation or light from an external source impinging on the brain is measured by suitable means and is made available to the subject on which the measurement is being made for his voluntary control. The measurement may be metabolic products of brain activity or some quality of the blood, such as its oxygen content. The system described therein utilizes red and infrared light to illuminate the brain through the translucent skull and scalp.

SUMMARY OF THE INVENTION

The present invention is directed to various methods relating to the use of behaviors performed by a subject and/or perceptions made by a subject that alter the activity of one or more brain regions of interest. It should be recognized that this alteration in activation may be a decrease or increase in activity at the different regions of interest.

One particular aspect of the invention relates to the use of behaviors performed by a subject and/or perceptions made by a subject that alter the activity of one or more regions of interest in combination with measuring the activation of the one or more regions of interest. Preferably, the measurement is performed in substantially real time relative to the behavior or perception. Activation metrics may be calculated based on the measured activity and used to monitor changes in activation.

Another particular aspect of the invention relates to the communication of information to a subject in combination with measuring the activation of the one or more regions of interest of the subject where the what, when, and/or how the information is communicated is determined, at least partially, based on the measured activity. Preferably, activity measurements are made continuously so that what, when, and/or how information is communicated to a subject in view of the activity measurements can be continuously determined. Examples of types of information that may be controlled in this manner include, but are not limited to instructions, stimuli, physiological measurement related information, and subject performance related information.

The present invention also relates to software that is designed to perform one or more operations employed in combination with the methods of the present invention. The various operations that are or may be performed by software will be understood by one of ordinary skill, in view of the teaching provided herein.

The present invention also relates to systems that may be used in combination with performing the various methods according to the present invention. These systems may include a brain activity measurement apparatus, such as a magnetic resonance imaging scanner, one or more processors and software according to the present invention. These systems may also include mechanisms for communicating information such as instructions, stimulus information, physiological measurement related information, and/or subject performance related information to the subject or an operator. Such communication mechanisms may include a display, preferably a display adapted to be viewable by the subject while brain activity measurements are being taken. The communication mechanisms may also include mechanisms for delivering audio, tactile, temperature, or proprioceptive information to the subject. In some instances, the systems further include a mechanism by which the subject may input information to the system, preferably while brain activity measurements are being taken.

In one embodiment, a method is provided for selecting how to achieve activation of one or more regions of interest of a subject, the method comprising: evaluating a set of behaviors that a subject separately performs regarding how well each of the behaviors in the set activate the one or more regions of interest; and selecting a subset of the behaviors from the set found to be effective in activating the one or more regions of interest. In one variation, evaluating the set of behaviors comprises calculating and comparing activation metrics computed for each behavior based on measured activities for the different behaviors. In one variation, the behaviors evaluated are overt behaviors involving a physical motion of the body of the subject. In another variation, the behaviors are covert behaviors only cognitive processes which do not lead to a physical motion of the body of the subject.

In another embodiment, a method is provided for selecting how to achieve activation of one or more regions of interest of a subject, the method comprising: evaluating a set of stimuli that a subject is separately exposed to regarding how well each of the different stimuli cause the subject to have a perception that activates the one or more regions of interest; and selecting a subset of the stimuli from the set found to be effective in causing activation of the one or more regions of interest. In one variation, evaluating the set of stimuli comprises calculating and comparing activation metrics computed for each stimuli based on measured activities for the different stimuli.

In another embodiment, a method is provided, the method comprising: evaluating a set of perceptions that a subject may have regarding how well each of the perceptions activate the one or more regions of interest; and selecting a subset of the perceptions from the set found to be effective causing activation of the one or more regions of interest. In one variation, evaluating the set of perceptions comprises calculating and comparing activation metrics computed for each stimuli based on measured activities for the different perceptions.

In another embodiment, computer executable logic is provided for selecting how to achieve activation of one or more regions of interest of a subject, the software comprising: logic for calculating activation metrics for activity measured for one or more regions of interest; and logic for comparing a set of calculated activation metrics and selecting a subset of the activation metrics having a superior activation of the one or more regions of interest.

In another embodiment, computer executable logic is provided for selecting how to achieve activation of one or more regions of interest of a subject, the software comprising: logic for calculating activation metrics for activity measured for one or more regions of interest during for a plurality of different behaviors; and logic for comparing the calculated activation metrics for the plurality of behaviors and selecting behaviors from the plurality based on the comparison of activation metrics.

In another embodiment, a method is provided for selecting a behavior for causing activation of one or more regions of interest of a subject, the method comprising: employing computer executable logic to select in substantially real time a next behavior for a subject to perform during training based, at least in part, on activity measurements made at or before the time the selection is made.

In another embodiment, a method is provided for directing behavior, the method comprising: employing computer executable logic to select in substantially real time a next behavior for a subject to perform during training based, at least in part, on activity measurements made at or before the time the selection is made.

In another embodiment, a method is provided for selecting a behavior for causing activation of one or more regions of interest of a subject, the method comprising: employing computer executable logic to select a next behavior for a subject to perform during training based, at least in part, on one or more behaviors previously used during training. In a variation, the selection is based on a combination of the one or more behaviors previously used during training and the activity measurements associated with the behaviors.

In another embodiment, a method is provided for selecting a behavior for causing activation of one or more regions of interest of a subject, the method comprising: employing computer executable logic to select a next behavior for a subject to perform during training based, at least in part, on measured activities of one or more regions of interest in response to the performance of one or more earlier behaviors. In a variation, the selection is based on a combination of the measured activity and the identity of the one or more earlier behaviors. It is noted that the computer executable logic may optionally compute activity metrics from the measured activity for the one or more earlier behaviors and base the selection on the activity metrics. Optionally, the computed activity metrics are based on a comparison with a rest state.

In another embodiment, a method is provided for selecting a stimulus for causing activation of one or more regions of interest of a subject, the method comprising: employing computer executable logic to select in substantially real time a next stimulus to communicate to a subject during training based, at least in part, on activity measurements made at the time the selection is made.

In another embodiment, a method is provided for selecting a stimulus for causing activation of one or more regions of interest of a subject, the method comprising: employing computer executable logic to select a next stimulus to communicate to a subject during training based, at least in part, on one or more stimuli previously communicated during training. In a variation, the selection is based on a combination of the one or more stimuli previously communicated and the activity measurements associated with the stimuli.

In another embodiment, a method is provided for selecting a stimulus for causing activation of one or more regions of interest of a subject, the method comprising: employing computer executable logic to select a next stimulus to communicate to a subject during training based, at least in part, on measured activities of one or more regions of interest in response to the communication of one or more earlier stimuli. In a variation, the selection is based on a combination of the measured activity and the identity of the one or more earlier stimuli. It is also noted that the computer executable logic may optionally compute activity metrics from the measured activity for the one or more earlier stimuli and base the selection on the activity metrics. Optionally, the computed activity metrics are based on a comparison with a rest state.

In regard to the above embodiments, it is noted that the next behavior or stimulus that is selected may be the same or different than the one or more earlier behaviors or stimuli.

In another embodiment, a computer assisted method is provided for guiding brain activity training comprising: measuring activity of one or more regions of interest of a subject; employing computer executable logic to select a behavior or stimulus for activating the one or more regions of interest based, at least in part, on the measured brain activity; and employing computer executable logic to communicate the selected behavior or stimulus to the subject. In one variation, the method further comprises communicating information to the subject regarding the measured brain activity.

In another embodiment, software is provided for guiding brain activity training, the software comprising: computer executable logic for selecting a behavior or stimulus for activating one or more regions of interest of a subject based, at least in part, on a measured brain activity; and logic for communicating the selected behavior or stimulus to the subject. In one variation, the software further comprises logic that communicates information to the subject regarding the measured brain activity.

In another embodiment, a computer assisted method is provided for guiding brain activity training comprising: having a subject perform a first behavior or be exposed to a first stimulus; measuring activity of one or more regions of interest of the subject in response to the first behavior or first stimulus; and employing computer executable logic to select a second behavior or a second stimulus for activating the one or more regions of interest based, at least in part, on the measured brain activity; and having the subject perform the second behavior or be exposed to the second stimulus. Optionally, the method further comprises employing computer executable logic to communicate to the subject the selected second behavior or second stimulus.

In another embodiment, a computer assisted method is provided for guiding brain activity training comprising: instructing a subject to perform a first behavior or communicating a first stimulus to the subject; measuring activity of one or more regions of interest of the subject in response to the first behavior or first stimulus; and employing computer executable logic to select a second behavior or a second stimulus for activating the one or more regions of interest based, at least in part, on the measured brain activity; and instructing the subject to perform the second behavior or communicating the second stimulus to the subject.

Computer executable software is provided for guiding brain activity training, the software comprising: logic for communicating instructions to a subject to perform a first behavior and/or a first stimulus to the subject; logic for taking activity measurements of one or more regions of interest of the subject in response to the first behavior or first stimulus and selecting a second behavior or a second stimulus for activating the one or more regions of interest based, at least in part, on the measured brain activity; and logic for communicating instructions to the subject to perform the second behavior and/or the second stimulus to the subject.

In another embodiment, computer executable software is provided for guiding brain activity training, the software comprising: logic for measuring activity of one or more regions of interest of the subject in response to a first behavior or first stimulus; logic for selecting a second behavior or a second stimulus for activating the one or more regions of interest based, at least in part, on a measured brain activity; logic for communicating to the subject the selected second behavior or second stimulus.

In another embodiment, a method is provided for directing training of one or more regions of interest of a subject, the method comprising: continuously measuring activity in the one or more regions of interest of the subject; and employing computer executable logic to determine when to communicate information to the subject based, at least in part, on the measured activities. It is noted that the computer executable logic may optionally compute activity metrics from the measured activity and base the selection on the activity metrics. The computer executable logic may determine when to communicate information based on when the computed activity metric satisfies a predetermined condition, such as a target activity metric. It is noted that the information may be instructions, stimuli, physiological measurement related information, and/or subject performance related information. In one variation, the instructions are instructions to perform a behavior.

In another embodiment, a method is provided for directing training of one or more regions of interest of a subject, the method comprising: measuring activity in the one or more regions of interest of the subject; determining one or more activity metrics for the measured activity; determining when the one or more activity metrics satisfy a predetermined condition; and communicating information to the subject; wherein these steps are repeatedly performed in substantially real time.

In another embodiment, software is provided for directing training of one or more regions of interest of a subject, the software comprising: logic for taking measurements of activity of the one or more regions of interest of the subject and determining one or more activity metrics for the measured activity; logic for determining when the one or more activity metrics satisfy a predetermined condition; and logic for causing information to be communicated to the subject; wherein the software is able to determine the activity metrics from the activity measurements and cause information to be communicated in substantially real time.

In another embodiment, a method is provided for directing training, the method comprising: measuring activities of one or more regions of interest; determining when the measured activities have reached a desired state; and communicating information to a subject regarding when to perform a next behavior when the measured activities have reached the desired state.

In another embodiment, a method is provided for directing training, the method comprising: measuring activities of one or more regions of interest; determining when the measured activities have reached a desired state; and communicating a stimulus to a subject when the measured activities have reached the desired state.

In another embodiment, computer executable software is provided, the software comprising: logic for taking activities of one or more regions of interest and determining when the measured activities have reached a desired state; and logic for causing information to be communicated to a subject regarding when to perform a next behavior when the measured activities have reached the desired state.

In another embodiment, computer executable software is provided, the software comprising: logic for taking measuring activities of one or more regions of interest and determining when the measured activities have reached a desired state; and logic for causing a stimulus to be communicated to a subject when the measured activities have reached the desired state.

In another embodiment, a method is provided for directing training of one or more regions of interest of a subject, the method comprising: measuring activity in the one or more regions of interest of the subject; determining one or more activity metrics for the measured activity; determining when the one or more activity metrics satisfy a predetermined condition; and communicating a performance reward to the subject; wherein these steps are repeatedly performed in substantially real time. In one variation, the activity metrics measure a similarity between the spatial pattern of activity within the region of interest and a target spatial pattern of activity.

In another embodiment, software is provided for directing training of one or more regions of interest of a subject, the software comprising: logic for taking measurements of activity of the one or more regions of interest of the subject and determining one or more activity metrics for the measured activity; logic for determining when the one or more activity metrics satisfy a predetermined condition; and logic for causing a performance reward to be communicated to the subject; wherein the software is able to determine the activity metrics from the activity measurements and cause information to be communicated in substantially real time.

In another embodiment, a method is provided for directing training of one or more regions of interest of a subject, the method comprising: measuring activity in the one or more regions of interest of the subject; determining what information is to be communicated to the subject based, at least in part, on the measured activity; wherein these steps are repeatedly performed in substantially real time. In one variation, the communicated information is a representation of the measured activity. In another variation, the communicated information is an instruction to the subject.

In another embodiment, a method is provided for directing training of one or more regions of interest of a subject, the method comprising: measuring activity in the one or more regions of interest of the subject; determining one or more activity metrics for the measured activity; determining when the one or more activity metrics satisfy a predetermined condition; and selecting information to be communicated to the subject based on the satisfaction of the predetermined condition. In a preferred embodiment, these steps are continuously performed. In one variation, the communicated information is a representation of the measured activity. In another variation, the communicated information is an instruction to the subject.

In another embodiment, software is provided for directing training of one or more regions of interest of a subject, the software comprising: logic taking measurements of activity of the one or more regions of interest of the subject and determining what information is to be communicated to the subject based, at least in part, on the measured activity; wherein the software is capable of taking the measurements of activity and determining what information is to be communicated in substantially real time. In one variation, the communicated information is a representation of the measured activity. In another variation, the communicated information is an instruction to the subject.

In another embodiment, software is provided for directing training of one or more regions of interest of a subject, the software comprising: logic taking measurements of activity of the one or more regions of interest of the subject and determining one or more activity metrics for the measured activity; logic for determining when the one or more activity metrics satisfy a predetermined condition; and logic for selecting information to be communicated to the subject based on the satisfaction of the predetermined condition. In a preferred embodiment, the software is capable of taking the measurements of activity and selecting the information to be communicated in substantially real time.

In another embodiment, a computer assisted method is provided for guiding brain activity training comprising: measuring activity of one or more regions of interest of a subject; employing computer executable software to determine information to communicate to the subject based, at least in part, on the measured brain activity; and employing computer executable software to communicate the information to the subject.

In another embodiment, a computer assisted method is provided for guiding brain activity training, the method comprising: measuring activity of one or more regions of interest of a subject; employing computer executable software to determine instructions based, at least in part, on the measured brain activity; and employing computer executable software to communicate the instructions to the subject. In one variation, measuring activity comprises recording activity data from a scanner, converting the recorded activity data to image data, and preprocessing the image data; and communicating the information comprises displaying images derived from the preprocessing image data.

In another embodiment, a method is provided for directing training of one or more regions of interest of a subject, the method comprising: measuring activity in the one or more regions of interest of the subject; determining how to communicate information to the subject based, at least in part, on the measured activity; wherein these steps are repeatedly performed in substantially real time.

In another embodiment, software is provided for directing training of one or more regions of interest of a subject, the software comprising: logic taking measurements of activity of the one or more regions of interest of the subject and determining how information is to be communicated to the subject based, at least in part, on the measured activity; wherein the software is capable of taking the measurements of activity and determining how information is to be communicated in substantially real time.

In another embodiment, a method is provided for selectively activating one or more regions of interest, the method comprising: (a) communicating one or more stimuli to a subject and/or having the subject perform one or more behaviors that are directed toward activating the one or more regions of interest without measuring activation of the one or more regions of interest; and (b) communicating the same one or more stimuli to the subject and/or having the subject perform the same behaviors as in step (a) in combination with measuring brain activity in the one or more regions of interest as the subject is exposed to stimuli and/or performs the behaviors. In one variation, information is displayed to the subject in step (a) that simulates the information that is displayed to the subject during step (b).

In another embodiment, software is provided for use in training, the software comprising logic for communicating information to guide a subject in the performance of a training exercise during which activation is not measured; and logic for communicating information to guide a subject in the performance of a training exercise during which activation of one or more regions of interest is measured; wherein information is displayed to the subject when activity is not measured that simulates activity measurements that are displayed when activity is measured.

In another embodiment, a method is provided for selectively activating one or more regions of interest, the method comprising: communicating information to a subject that instructs a subject to perform a sequence of behaviors or have a series of perceptions that are adapted to cause the selective activation of one or more regions of interest.

In another embodiment, a method is provided for selectively activating one or more regions of interest, the method comprising: identifying information that instructs a subject to perform a sequence of behaviors or have a series of perceptions that selectively causes activation of one or more brain regions in a subject; communicating the identified information to a same or different subject; and measuring activation of one or more regions of interest in response to the communicated information.

In another embodiment, software is provided for use in training, the software comprising logic for communicating information to guide a subject in the performance of a training exercise during which activation of one or more regions of interest is not measured, the logic displaying information that simulates activity measurements of the one or more regions of interest.

In another embodiment, software and information is provided for use in training, the software comprising logic for communicating information to guide a subject in the performance of a training exercise during which activation is not measured, and the information comprising stimuli, instructions, and/or measured information having been determined based in part upon activity in a region of interest during a training period when activity was measured and communicated to the same or a different subject in substantially real time.

In another embodiment, a method is provided for selecting how to achieve activation of one or more regions of interest, the method comprising: (a) having a subject perform a set of behaviors; (b) measuring how well each of the behaviors in the set activate the one or more regions of interest; (c) selecting a subset of the behaviors from the set found to be effective in activating the one or more regions of interest; and (d) after step (c) and in the absence of measuring activation, determining what information to communicate to the same or a different subject based, at least in part, on the activity measurements of step (b). In one variation, evaluating the set of behaviors comprises calculating and comparing activation metrics computed for each behavior based on measured activities for the different behaviors. In another variation, the behaviors evaluated are overt behaviors involving a physical motion of the body of the subject. In another variation, the behaviors are covert behaviors only cognitive processes which do not lead to a physical motion of the body of the subject. In the case when the subject in step (a) is different than the subject in step (d), the subject in step (d) may have a commonality with the subject of step (a) in relation to the one or more regions of interest upon which the behaviors were selected.

In another embodiment, computer executable logic is provided for selecting how to achieve activation during training of one or more regions of interest of a subject, the software comprising: logic for calculating activation metrics for activity measured for one or more regions of interest in a first subject; logic for comparing a set of calculated activation metrics and selecting a subset of the activation metrics having a superior activation of the one or more regions of interest in that first subject; logic that takes the measured brain from the first subject and determines for a second subject one or more members of the group consisting of: a) what next stimulus to communicate to the second subject, b) what next behavior to instruct the second subject to perform, c) when the second subject is to be exposed to a next stimulus, d) when the second subject is to perform a next behavior, e) one or more activity metrics computed from the measured activity in the first subject, f) a spatial pattern computed from the measured activity in the first subject, g) a location of a region of interest computed from the measured activity of the first subject, h) performance targets that the second subject is to achieve computed from the measured activity in the first subject, i) a performance measure the second subject's success computed from the measured activity in the first subject; and logic for communicating information based on the determinations to the second subject. In one variation, the information communicated to the second subject is communicated during a process of training. In another variation, the information communicated to the second subject is a set of instructions and/or stimuli to be used by the second subject in performing training trials. In another variation, the information communicated to the second subject is a set of instructions and/or stimuli to be used by the second subject in performing training trials for the activation of a brain region of interest in the second subject.

In another embodiment, computer executable logic is provided for selecting how to achieve activation during training of one or more regions of interest of a subject, the software comprising: logic for calculating activation metrics for activity measured for one or more regions of interest during each of several behaviors in a first subject; logic for comparing a set of calculated activation metrics corresponding to the set of behaviors and selecting a subset of the activation metrics and their corresponding behaviors having a superior activation of the one or more regions of interest in that first subject; logic that takes the measured brain activity from the first subject and determines information to communicate to a second subject; and logic for communicating the determined information to the second subject. In one variation, the logic communicates the determined information to the first subject in substantially real time relative to when the activity is measured.

In another embodiment, a method is provided for selecting how to achieve activation during training of one or more regions of interest of a subject, the method comprising: calculating activation metrics for activity measured for one or more regions of interest during each of several behaviors in a first subject; and comparing a set of calculated activation metrics corresponding to the set of behaviors and selecting a first subset of the activation metrics and their corresponding behaviors having a superior activation of the one or more regions of interest in that first subject; at a later time: (a) having a second subject perform a behavior adapted to selectively activate one or more regions of interest in the first subject; and (b) optionally communicating information to the second subject based on the measured brain activity in the first subject; wherein steps (a)-(b) are repeated multiple times, the second subject using the communicated information to guide the second subject in the subsequent performance of the behavior. In one variation, computer executable logic is employed to select the information communicated to the subject. In another variation, computer executable logic is employed to cause the information to be communicated to the second subject. In one variation, the first subject and the second subject are the same subject. In another variation, the first subject and the second subject are different subjects. In the case when the first and the second subject are different subjects, the second subject may additionally have been selected based upon having a condition likely to benefit from similar training as that received by first subject.

In another embodiment, a computer assisted method is provided for guiding brain activity training comprising: measuring activity of one or more internal voxels of a brain; employing computer executable logic that takes the measured brain activity and determines one or more members of the group consisting of: a) what next stimulus to communicate to the subject, b) what next behavior to instruct the subject to perform, c) when a subject is to be exposed to a next stimulus, d) when the subject is to perform a next behavior, e) one or more activity metrics computed from the measured activity, f) a spatial pattern computed from the measured activity, g) a location of a region of interest computed from the measured activity, h) performance targets that a subject is to achieve computed from the measured activity, i) a performance measure of a subject's success computed from the measured activity, j) a subject's position relative to an activity measurement instrument; and communicating information based on the determinations to the subject in substantially real time relative to when the activity is measured.

Computer executable software for guiding brain activity training is also provided that comprises: logic which takes data corresponding to activity measurements of one or more internal voxels of a brain and determines one or more members of the group consisting of: a) what next stimulus to communicate to the subject, b) what next behavior to instruct the subject to perform, c) when a subject is to be exposed to a next stimulus, d) when the subject is to perform a next behavior, e) one or more activity metrics computed from the measured activity, f) a spatial pattern computed from the measured activity, g) a location of a region of interest computed from the measured activity, h) performance targets that a subject is to achieve computed from the measured activity, i) a performance measure of a subject's success computed from the measured activity, j) a subject's position relative to an activity measurement instrument; and logic for communicating information based on the determinations to the subject in substantially real time relative to when the activity is measured.

Computer executable software is also provided for guiding brain activity training that comprises logic which takes a measurement of brain activity in one or more regions of interest of a subject while the subject has one or more perceptions and/or performs one or more behaviors that are directed toward activating the one or more regions of interest and determines one or more members of the group consisting of a) what next stimulus to expose the subject to, b) what next behavior to have the subject perform, c) what information to communicate to the subject, d) when a subject is exposed to the next stimulus, e) when the subject is to perform the next behavior, f) when new information is to be communicated to the subject, g) how a subject is exposed to the next stimulus, h) how the subject is to perform the next behavior, and i) how new information is to be communicated to the subject. In one variation, the software performs the determinations in substantially real time relative to when the brain activity measurement is taken. In another variation, the determined information is communicated to the subject.

In another embodiment, a method for guiding brain activity training is provided that comprises: having a subject perform a behavior or be exposed to a stimulus; measuring activity of the one or more regions of interest as the behavior is performed or the subject is exposed to the stimulus; and communicating information to the subject based on the measured brain activity in substantially real time relative to when the behavior is performed or the subject is exposed to the stimulus.

In another embodiment, computer executable software is provided for guiding brain activity training, the software comprising: logic for instructing a subject to perform a behavior; logic for taking activity measurements of one or more regions of interest as the behavior is performed and communicating information to the subject based on the measured brain activity in substantially real time relative to when the behavior is performed.

In another embodiment, a method is provided for guiding brain activity training, the method comprising: (a) having a subject perform a behavior adapted to selectively activate one or more regions of interest; (b) measuring activity of the one or more regions of interest as the behavior is performed; and (c) communicating information to the subject based on the measured brain activity in substantially real time relative to when the behavior is performed; wherein steps (a)-(c) are repeated multiple times, the subject using the communicated information to guide the subject in the subsequent performance of the behavior. In one variation, computer executable logic is employed to select the information communicated to the subject. In another variation, computer executable logic is employed to cause the information to be communicated to the subject.

In another embodiment, computer executable software is provided for guiding brain activity training, the software comprising: logic for taking activity measurements of one or more regions of interest as a behavior is performed; and logic for communicating information to the subject based on the measured brain activity in substantially real time relative to when the behavior is performed; wherein the logic takes new activity measurements as they are received and communicates new information based on the new activity measurements. In one variation, the software is able to take the activity measurements and cause the information to be communicated in substantially real time. In another variation, the software further includes logic for selecting what information is to be communicated.

In another embodiment, a method is provided for diagnosing a condition of a subject associated with particular activation in one or more regions of interest, the method comprising: having the subject perform a behavior or have a perception adapted to selectively activate one or more regions of interest associated with the condition; measuring activity of the one or more regions of interest as the behavior is performed or the subject has the perception; and diagnosing a condition associated with the one or more regions of interest based on the activity in response to the behavior or perception.

In another embodiment, a computer assisted method is provided for diagnosing a condition of a subject associated with particular activation in one or more regions of interest, the method comprising: having computer executable logic cause instructions to perform a behavior and/or a stimulus be communicated to the subject, the behavior and/or stimulus being adapted to selectively activate one or more regions of interest associated with the condition; having computer executable logic take activity measurements of the one or more regions of interest in response to the behavior and/or stimulus and diagnose whether the condition is present based on the activity response to the behavior and/or stimulus.

In another embodiment, a method is provided for designing a treatment for a condition of a subject, the method comprising: identifying a behavior or stimulus adapted to selectively activate one or more regions of interest associated with a condition to be treated; having the subject perform the selected behavior or exposing the subject to the selected stimulus; measuring activity of the one or more regions of interest as the behavior is performed or the subject is exposed to the stimulus in order to evaluate the effectiveness of the treatment. In one variation, the method further comprises identifying the one or more regions of interest of a subject associated with the condition to be treated.

In another embodiment, computer executable software is provided for designing a treatment for a condition of a subject, the software comprising: logic for identifying a behavior or stimulus adapted to selectively activate one or more regions of interest associated with a condition to be treated; logic for instructing the subject to perform the selected behavior and/or communicating the selected stimulus to the subject; and logic for taking activity measurements of the one or more regions of interest as the behavior is performed or the subject is exposed to the stimulus and evaluating the effectiveness of the treatment. In one variation, the software further comprises logic for identifying the one or more regions of interest of a subject associated with the condition to be treated.

In another embodiment, a method is provided for treating one or more regions of interest of a brain of a subject, the method comprising: having a subject perform a behavior or have a perception adapted to activate one or more regions of interest where the resulting activity of the one or more regions of interest is measured as the behavior is performed or the subject is exposed to the stimulus. In one variation, information selected from the group consisting of instructions, stimuli, physiological measurement related information, and subject performance related information is communicated to the subject as the behavior is performed or the perceptions are being made. In another variation, information selected from the group consisting of instructions, stimuli, physiological measurement related information, and subject performance related information is communicated to the subject as the behavior is performed or the perceptions are being made, the information communicated to the subject is selected based, at least in part, on the measured activity. In one variation, the one or more regions of interest selected are implicated in the etiology of a condition that the subject has. In another variation, the one or more regions of interest selected are related to a disease state. In another variation, the one or more regions of interest selected have an abnormality related to a disease state. In another variation, the one or more regions of interest are adjacent to a region of the brain that has been injured.

In another variation, a method is provided for selecting a brain region of interest, the method comprising: having a subject perform a behavior or have a perception adapted to activate one or more localized regions of the brain; measuring activity of the localized regions of the brain of the subject as the behavior is performed or the perception is made; and identifying one or more localized regions of the brain of the subject whose activation changes in response to the behavior or perception. In one variation, the method further comprises storing a location of the identified one or more regions of interest to memory. In one variation, identifying the one or more localized regions of the brain is performed less than 10, 5, 1, 0.1 minutes after the behavior is performed or the perception is had.

In another variation, computer executable software is provided for selecting a brain region of interest, the software comprising: logic for instructing a subject perform a behavior adapted to activate one or more localized regions of the brain; logic for taking activity measurements of the regions of interest of the subject as the behavior is performed and identifying one or more regions of interest of the subject whose activation changes in response to the behavior or perception. In one variation, the software further comprises logic for selecting coordinates corresponding to the identified one or more regions of interest. In another variation, the software further comprises logic for selecting coordinates corresponding to the identified one or more regions of interest and storing the selected coordinates to memory.

In another embodiment, a method is provided for selecting a brain region of interest, the method comprising: having a subject perform a behavior or have a perception; measuring activity of the regions of interest of the subject as the behavior is performed or the perception is made; and identifying one or more regions of interest of the subject whose activation changes in response to the behavior or perception.

In another embodiment, a computer assisted method is provided for evaluating an effectiveness of brain activity training comprising: selecting a target level of activation for one or more regions of interest of a subject; having the subject perform a behavior or have a perception; measuring activity of one or more regions of interest of a subject; employing computer executable software to compare the measured activity to the target level of activity. In one variation, the target level of activity is communicated to the subject. In another variation, the target level of activity is displayed to the subject as the subject performs the behavior or has the perception. In yet another variation, the comparison between the measured activity and the target level of activity is communicated to the subject. In yet another variation, the comparison between the measured activity and the target level of activity is displayed to the subject. In yet another variation, the computer executable software selects information to be communicated to the subject based on the comparison between the measured and target levels of activity. In yet another variation, the software selects instructions to be communicated to the subject based on the comparison between the measured and target levels of activity. In yet another variation, the software selects a behavior to be performed or a stimulus to expose the subject to based on the comparison between the measured and target levels of activity. In yet another variation, comparing comprises computing one or more members of the group consisting of a vector difference, a vector distance, and a dot product between two vectorized spatial patterns of physiological activity.

In another embodiment, computer executable software is provided for evaluating an effectiveness of brain activity training, the software comprising: logic for selecting a target level of activation for one or more regions of interest of a subject; logic for communicating instructions to the subject to perform a behavior and/or communicate a stimulus to the subject; logic for taking activity measurements of one or more regions of interest of a subject and comparing the measured activity to the target level of activity. In one variation, the software comprises logic for communicating the target level of activity to the subject. In another variation, the software comprises logic for causing the target level of activity to be displayed to the subject as the subject performs the behavior or as the stimulus is communicated. In yet another variation, the software comprises logic that communicates the comparison between the measured activity and the target level of activity to the subject. In yet another variation, the software comprises logic for displaying the comparison between the measured activity and the target level of activity to the subject. In yet another variation, the software comprises logic for selecting information to be communicated to the subject based on the comparison between the measured and target levels of activity. In yet another variation, the software comprises logic for selecting instructions to be communicated to the subject based on the comparison between the measured and target levels of activity. In yet another variation, the software comprises logic for selecting a behavior to be performed or a stimulus to communicate to the subject based on the comparison between the measured and target levels of activity. In yet another variation, the logic for comparing comprises logic for computing one or more members of the group consisting of a vector difference, a vector distance, and a dot product between two vectorized spatial patterns of physiological activity.

In another embodiment, a training method is provided that comprises: having a subject perform a behavior or be exposed to a stimulus; measuring activity of the one or more regions of interest as the behavior is performed or the subject is exposed to the stimulus; and having the subject estimate the measured activity. In one variation, no behavior or stimulus may be used. In another variation, the behavior used is the cognitive process of forming an estimate of measured activity. In one variation, the method further comprises communicating information to the subject regarding how well the subject estimated the measured activity. In another variation, the subject inputs his or her estimate into a system. In another variation, the method further comprises recording to memory how well the subject estimated the measured activity. In another variation, an activity metric is calculated based on the measured activity and the subject estimates the activity metric. It is noted that the subject's estimate of the measured activity can be a qualitative estimate (e.g., higher than a value, lower than a value) or quantitative (e.g., a numerical estimate).

In another embodiment, computer executable software is provided that comprises: logic for taking activity measurements for one or more regions of interest; and logic for receiving a subject's estimate of activation of one or more regions of interest in response to a behavior or perception and comparing that estimate to the measured activation for one or more regions of interest. In one variation, the software further comprises logic for creating a displayable image illustrating the comparison of the subject's estimate. In another variation, the software further comprises logic for communicating information to the subject regarding how well the subject estimated the measured activation. In another variation, the logic stores the estimate and activation measurements to memory. In another variation, the logic calculates an activity metric based on the measured activation. In another variation, the subject's estimate is an estimated activity metric and the logic compares an activity metric based on the measured activation to the subject's estimated activity metric. It is noted that the subject's estimate of the measured activity can be a qualitative estimate (e.g., higher than a value, lower than a value) or quantitative (e.g., a numerical estimate).

Also according to any of the above embodiments, the behavior may optionally be selected from the group consisting of sensory perceptions, detection or discrimination, motor activities, cognitive processes, emotional tasks, and verbal tasks.

Also according to any of the above embodiments, the methods are optionally performed with the measurement apparatus remaining about the subject during the method.

According to any of the above embodiments, in one variation, measuring activation is performed by fMRI.

According to any of the above embodiments, in one variation, the activity measurements are made using an apparatus capable of taking measurements from one or more internal voxels without substantial contamination of the measurements by activity from regions intervening between the internal voxels being measured and where the measurement apparatus collects the data.

Also according to any of the above embodiments, pretraining is optionally performed as part of the method.

Also according to any of the above embodiments, in one variation, at least one of the regions of interest is an internal region of the brain.

Also according to any of the above embodiments, in one variation, the one or more localized regions are all internal relative to a surface of the brain.

Also according to any of the above embodiments, in one variation, the one or more regions of interest comprise a voxel.

Also according to any of the above embodiments, in one variation, the one or more regions of interest comprise a plurality of different voxels.

According to any of the above embodiments, in one variation, the one or voxels measured has a two dimensional area. The two dimensional area optionally has a diameter of 50, 30, 20, 15, 10, 5, 4, 3, 2, 1, 0.5, 0.1 mm or less.

According to any of the above embodiments, in one variation, the one or more voxels measured has a three dimensional volume. The three dimensional volume optionally has a volume of 22×22×12 cm, 11×11×6 cm, 6×6×6 cm, 3×3×3 cm, 1×1×1 cm, 0.5×0.5×0.5 cm, 1×1×1 mm, 100×100×100 microns or less.

Also according to any of the above embodiments, in one variation, measurements are made from at least 100 separate internal voxels, and these measurements are made at a rate of at least once every five seconds.

Also according to any of the above embodiments, in one variation, measurements are made from a set of separate internal voxels corresponding to a scan volume including the entire brain.

According to any of the above embodiments, the one or more regions of interest optionally include one or members of the group consisting of neuromodulatory centers or plasticity centers.

Also according to any of the above embodiments, the methods may be performed in combination with the administration of an agent for enhancing measurement sensitivity of the one or more regions of interest. For example, in one variation, the method is performed in combination with the administration of a fMRI contrast agent. In another variation, the method is performed in combination with the administration of an agent that enhances activity in the one or more regions of interest.

According to any of the above embodiments, measuring brain activity is optionally performed continuously as the subject performs a behavior, has a perception and/or is exposed to a stimulus. For example, measuring brain activity is optionally performed at least every 10, 5, 4, 3, 2, or 1, 0.1, 0.01 seconds or less as the subject performs a behavior, has a perception and/or is exposed to a stimulus.

According to any of the above embodiments, the subjects performs one or more behaviors during measurement that constitute training to activate one or more brain region of interest.

According to any of the above embodiments, the method is used to guide brain activity training by instructing a subject to modulate a brain region of interest.

According to any of the above embodiments, an action is performed in response to a brain activity measurement in substantially real time. For example, an action is optionally performed in response to a brain activity measurement at least every 10, 5, 4, 3, 2, or 1, 0.1, 0.01 seconds or less.

Also according to any of the above embodiments, the behavior is optionally a cognitive task the subject is to perform based on an image displayed to the subject.

Also according to any of the above embodiments, in one variation, communicating information to the subject (for example: instructions, stimuli, physiological measurement related information, and subject performance related information) is performed by one or more of the members selected from the group consisting of providing audio to the subject, providing a smell to the subject, displaying an image to the subject.

Also according to any of the above embodiments, a desired activity metric to be achieved optionally is determined and/or communicated.

Also according to any of the above embodiments, whether a desired activity metric is achieved optionally is determined and/or communicated.

Also according to any of the above embodiments, an activity metric is optionally determined and/or communicated from measured activity. In one variation, the activity metric is modified relative to a baseline level of activation. In another variation, the activity metric is normalized relative to a baseline level of activation. In another variation, a comparison between an activity metric and a reference activity metric is performed.

Also according to any of the above embodiments, a measured activity metric may optionally be determined and/or communicated. In one variation, the activity metric is modified relative to a baseline level of activation. In another variation, the activity metric is normalized relative to a baseline level of activation. In another variation, a comparison between an activity metric and a reference activity metric is performed.

Also according to any of the above embodiments, a measured activation image or volume may optionally be determined and/or communicated. In one variation, the activation image or volume is modified relative to a baseline level of activation. In another variation, the activation image or volume is normalized relative to a baseline level of activation. In another variation, a comparison between an activation image or volume and a reference activation image or volume is performed.

Also according to any of the above embodiments, in one variation, the subject performs a behavior, has a perception and/or is exposed to a stimulus repeatedly for a period of at least 1, 5, 10, 20, 30, 60 or more minutes. Also according to any of the above embodiments, in one variation, the subject performs a behavior, has a perception and/or is exposed to a stimulus repeatedly at least 2, 3, 4, 5, 10, 20, 100 or more minutes.

Also according to any of the above embodiments, in one variation, activity measurements are recorded to memory during the method. Optionally, activity measurements and the behaviors and/or stimuli used are recorded to memory during the method. Optionally, any information communicated to the subject is also recorded to memory.

Also according to any of the above embodiments, in one variation, activity measurements may be communicated to a remote location. Optionally, activity measurements and the behaviors and/or stimuli used communicated to a remote location during the method. Optionally, any information communicated to the subject is also communicated to a remote location. In one example, this communication to a remote location takes place via internet communication. In another example, this communication to a remote location takes place via wireless communication.

According to any of the above embodiments where information is communicated, in one variation, the information is communicated by a manner selected from the group consisting of providing audio to the subject, providing tactile stimuli to the subject, providing a smell to the subject, displaying an image to the subject.

According to any of the above embodiments wherein information is determined, in one variation, the information is determined while the instrument used for measurement remains positioned about the subject Also according to any of the above embodiments wherein information is communicated, in one variation, the information communicated is an instruction to the subject.

Also according to any of the above embodiments wherein information is communicated, in one variation, the instruction is a text or iconic indication denoting an action that a subject is to perform.

Also according to any of the above embodiments wherein information is communicated, in one variation, the instruction identifies a task to be performed by the subject.

Also according to any of the above embodiments wherein information is communicated, in one variation, some of the information communicated to the subject is material to be learned.

Also according to any of the above embodiments wherein an instruction is determined, in one variation, the instruction is determined by computer executable logic.

Also according to any of the above embodiments wherein an instruction is communicated, in one variation, the instruction communicated is selected from a set of instructions stored in memory, the selection being based upon the brain activity measured.

Also according to any of the above embodiments, the subject may optionally input information to the system while brain activity measurements are being taken or while the subject is in a position where brain activity measurements may be taken.

Also according to any of the above embodiments, in one variation, the method further comprises selecting one or more of the internal voxels to correspond to a region of interest for a particular subject and using the selected internal voxels of the region of interest to make the one or more determinations.

Also according to any of the above embodiments, in one variation, the region of interest is selected from the group consisting of one of the regions listed in FIG. 14, including the substantia nigra, subthalamic nucleus, nucleus accumbens, locus coeruleus, periaqueductal gray matter, nucleus raphe dorsalis, nucleus basalis of Meynert, dorsolateral prefrontal cortex.

Also according to any of the above embodiments, in one variation, the region of interest has a primary function of releasing a neuromodulatory substance, where the neuromodulatory substance is selected from the group consisting of: dopamine, acetyl choline, noradrenaline, serotonin, an endogenous opiate.

Also according to any of the above embodiments, in one variation, the subject has one or more of the following conditions: Parkinson's disease, Alzheimer's disease, attention & attention deficit disorder, depression, substance abuse & addiction, schizophrenia.

These and other embodiments and variations of the methods, software and systems of the present invention are described herein.

BRIEF DESCRIPTION OF THE DRAWINGS

FIG. 2 is a table of brain regions.

FIG. 3 is a table of neurological, psychological and other conditions.

FIG. 14 shows a table of brain regions that may be used as regions of interest.

DEFINITIONS

Figure 1:
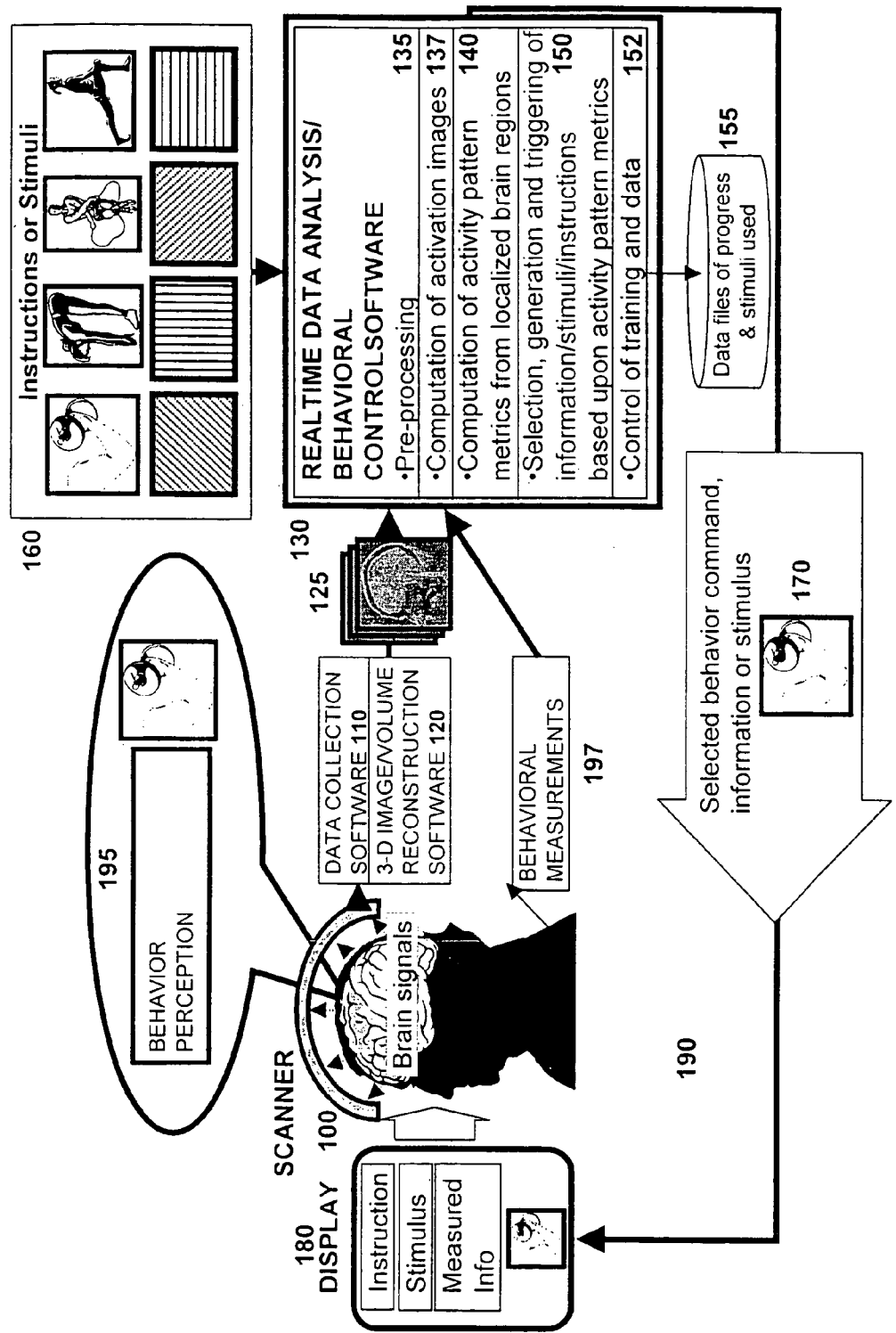
FIG. 1 is an overview diagram of methods, components and processes of this invention.

Activity, as used herein, refers to physiological activity associated with one or more voxels of the brain whose physiological activity may be monitored. Examples of types of physiological activity include, but are not limited to, neuronal activity, blood flow, blood oxygenation, electrical activity, chemical activity, tissue perfusion, the level of a nutrient or trophic factor, the production or distribution of a trophic factor, the production, release, or reuptake of a neurotransmitter or neuromodulator, the growth of tissue such as neurons or parts of neurons, neural plasticity, and other physiological processes. Other examples are provided herein.

Activation, as used herein, refers to a change in activity in one or more voxels of the brain whose physiological activity may be monitored. This change may include an increase or decrease. It is noted that this change may also include a change where some voxels increase in activation at the same time that other voxels decrease in activation.

Activity metric, as used herein, refers to any computed measure of activity of one or more regions of interest of the brain.

Altering activity, as used herein, refers to an alteration in activity levels in one or more regions of interest of the brain. It is noted that altering activity can be an increase and/or a decrease in activation. When a plurality of voxels of the brain are involved, all or only some may have increased activity and all or only some may have decreased activity. It should be recognized that some voxels may have increased activity while other voxels have decreased activity.

Anti-nociceptive regions, as used herein, refers to areas of the brain which, when active, may produce a decrease or modulation in the sensation of experienced severity of pain.

Behavioral training, as used herein, refers to training a subject to generate an overt action in response to a form of information that is communicated to the subject. It is noted that behavioral training may take place in combination with training a subject to alter activity in one or more regions of interest.

Behavior, as used herein, refers to a physical or mental task or exercise engaged in by a subject, which may be in order to activate one or more regions of interest of the brain. Examples of different types of behaviors include, but are not limited to sensory perception, detection or discrimination, motor activities, cognitive processes such as mental imagery or mental manipulation of an imagined object, reading, emotional tasks such as attempting to create a particular affect or mood, verbal tasks such as listening to, comprehending, or producing speech. Other examples of behaviors are provided herein.

BOLD, as used herein refers to Blood Oxygen Level Dependent signal. This signal is typically measured using a functional magnetic resonance imaging device.

Condition, as used herein, refers to any physiological, psychological or health condition that may be treated according to the present invention by changing a level of activity in one or more regions of interest associated with that condition. Numerous examples of conditions that may be treated according to the present invention are provided herein. It is noted that a condition may additionally refer to a normal state of a subject that one may desire to alter, such as the condition of a subject's mood.

Device operator, as used herein, refers to an individual who controls the functioning of apparatus or software associated with this invention. It is to be noted that the device operator may be a person other than the subject, may be the subject, or may be a remotely located party using appropriate communication technology such as an internet connection.

Endopharmacology or endomedication, as used herein, refers to the activation or modulation of a brain region that releases endogenous neuromodulatory substances or neurotransmitters onto one or more target regions, and thereby regulates neuronal function.

Event related, as used herein, refers to an event that is related to a physiological activity which is caused by a known event, or takes place immediately preceding or subsequent to that event. In a typical example, a stimulus or behavior event is repeated many times, and the average event related activity is the average activity level at a set of defined times relative to the onset time of the event. This may be computed using a PETH.

Exemplar, as used herein, refers to an instance that serves as a member of a set. Exemplar stimuli are stimuli taken as instances from a set, such as a set of stimuli, the perception of which are thought to engage a particular region of interest. Exemplar behaviors are behaviors taken as instances from a set, such as a set of behaviors, the performance of which are thought to engage a particular region of interest.

Exercise, as used herein, refers to repeated training, such as training designed to activate a brain region.

Existing MRI/fMRI/PET data processing packages, as used herein refers to the following packages, their documentation, websites, and cited literature references contained in their documentation and websites: SPM99 (and the SPM99 manual written by Dick Veltman and Chloe Hutton, May 2001), Brain Voyager from Brian Innovation, AIR by Roger Woods, MRICro by Chris Rorden, AFNI by R W Cox, and other packages that may be developed to perform related functions.

Information, as used herein, refers to anything communicated to the subject, whether by sight, sound, smell, contact with the subject, etc., relating to the performance of the various methods of the present invention. Examples of various types of information that may be communicated to the subject include, but are not limited to, instructions, physiological measurement related information, subject performance related information, and stimulus information that causes the subject to have a perception. Examples of ways of communicating information include, but are not limited to displaying information to the subject, playing audio for the subject, providing an agent for the subject to smell, applying a physical force to the subject (e.g., a pressure or vibration or proprioceptive stimulus), and causing a physical sensation for the subject (e.g., cold, hot, pain, electrical charge, etc.). Specific examples of information include, but are not limited to images of the subject's brain activity pattern, charts of the timecourse of physiological activity in a region of interest, or an activity metric from a region of interest, instructions to perform a task or how to perform a task, movies, or stereoscopic virtual reality stimuli viewed through stereo viewers and designed to simulate certain circumstances or experiences. Further examples include games played by the subject, such as computer games.

Instructions, as used herein, refers to any instruction to perform a physical or mental action that is communicated to a subject or an operator assisting a subject. Examples of instructions include, but are not limited to instructions to a subject to perform a behavior; instructions to a subject to rest; instructions to a subject to move; instructions to a subject to make a computer input; instructions to a subject to activate a brain region, such as to a designated level. Further examples of instructions are provided herein.

Localized region, as used herein refers to any region of the brain with a defined spatial extent. In one variation, a localized region measured by this invention may be internal relative to a surface of the brain.

Measurement information, as used herein, refers to any information that communicates a measurement to a subject. Examples of types of measurements include, but are not limited to anatomical measurements, physiological measurements, activity measurements, activity metrics computed from activity measurements, and activation images.

Measurement of activity, as used herein, refers to the detection of activity in one or more voxels of the brain. Once measured, activity metrics may be computed from these measurements. Activity measurements may be performed by any measurement technology that is capable of measuring activity in one or more voxels of the brain, or by combinations of such technologies with other forms of measurement. Various suitable measurement technologies are described herein.

Neuromoanatomical texts, as used herein refers to any of a variety of texts describing the structures of the brain, including but not limited to Fundamental Neuroanatomy by Nauta and Feirtag, and in the Co-Planar Steriotaxic Atlas of the Human Brain by Jean Talairach and Pierre Tournoux, Magnetic Resonance Imaging of the Brain and Spine (2 Volume Set) by Scott W., Md. Atlas.

Neuromodulator or neuromodulatory substance, as used herein, refers to compounds which can alter activity or responsiveness in one or more localized regions of the brain. Examples of neuromodulators include, but are not limited to: opioids, neuropeptides, acetylcholine, dopamine, norepinephrine, serotonin and other biologic amines, and others. Many pharmacologic agents such as morphine, caffeine and prozac are exogenous mimics of these neuromodulatory substances.

Neuromodulatory centers, as used herein, refers to regions of the brain or nervous system that serve to regulate or alter responsiveness in other parts of the nervous system. Examples include regions that contain neurons that release neuromodulatory transmitters such as catecholamines, acetylcholine, other biologic amines, neuropeptides, serotonin, norepinephrine, dopamine, adrenaline. These centers and the actions produced through their modulation are described in neuroanatomy texts and The Biochemical Basis of Neuropharmacology, Cooper, Bloom and Roth. Examples include but are not limited to the nucleus raphe magnus, substantia nigra (pars compacta and reticulata), nucleus accumbens, periaqueductal gray, locus coeruleus, nucleus basalis, red nucleus, nucleus accumbens.

PETH, as used herein, refers to a peri-event time histogram. This is a measure of the average value of an activity pattern metric based upon multiple trials, for each of a set of fixed time intervals after a conditioning event such as a stimulus or the onset of a behavior.

Perception, as used herein, refers to a cognitive response by a subject that may result in the activation of one or more localized regions of the brain. In some instances, the perception is in response to stimulus information that is communicated to the subject. However, the perception may also be independent of stimulus being communicated to the subject.

Performance target, as used herein, refers to an activity metric that a subject may be instructed to achieve. The performance target may be communicated to the subject in some manner before, during or after a trial.

Pharmacological treatment, as used herein, refers to the administration of any type of drug, remedy, or medication.

Region of interest or ROI or volume of interest, as used herein, refers to a particular one or more voxels of the brain of a subject. An ROI may occasionally be referred to as an area or volume of interest since the region of interest may be two dimensional (area) or three dimensional (volume). Frequently, it is an object of the methods of the present invention to monitor, control and/or alter brain activity in the region of interest. For example, the one or regions of interest of the brain associated with a given condition may be identified as the region of interest for that condition. In one variation, the regions of interest targeted by this invention are internal relative to a surface of the brain.

Regulation or modulation, as used herein, refers to a subject performing a behavior or having a perception that controls activity in a region of interest. Regulation may cause the activity to increase or decrease relative to a desired level, or to change spatial pattern. Regulation may be monitored using one or more activity metric, for example by monitoring for an increase, decrease, or maintenance in the activity metric. Preferably, regulation provides control over activity for at least a selected period of time (e.g. seconds, minutes, days, or longer).

Reward centers or pleasure centers, as used herein, refers to areas of the brain which, when active, produce pleasurable or rewarding experiences or sensations. These include, but are not limited to certain limbic structures, the nucleus accumbens, locus coeruleus, septal nuclei, and others. These may also include areas that have been associated with addictive behaviors.

Reward, as used herein, refers to information, incentives, or objects given or promised to subjects to encourage their positive performance in a task. These include numerical values of performance level such as percent correct, encouragement, enjoyable activities, or monetary or other enticements toward correct performance.

Scan volume, as used herein, refers to a three dimensional volume within which brain activity is measured. This volume may be divided into an array of voxels. For example, in the case of fMRI, a scanning volume may correspond to a 3-D cube (e.g., 22×22×12 cm) that comprises the volume of the head of a subject. This volume may be divided into a 64×64×17 array of subvolumes (voxels).

Single point, as used herein, refers to an individual geometric locus or small area of volume, such as a single small geometric volume from which a physiological measurement will be made, with the volume being 0.1, 0.5, 1, 2, 3, 4, 5, 10, 15, 20, 30, 50, 100 mm in diameter. A device making a measurement from a single point is contrasted with a device making scanned measurements from an entire volume comprised of many single points.

Spatial array, as used herein, refers to a contiguous or non-contiguous set of location points, areas or volumes in space. The spatial array may be two dimensional in which case elements of the array are areas or three dimensional in which case elements of the array are volumes.

Spatial pattern, or spatial activity pattern, or vectorized spatial pattern, as used herein, refers to the measured activities of the set of voxels forming a two dimensional or three dimensional spatial array such as a scan volume or portion of a scan volume. A vector comprising a rational or real value for each voxel in a three dimensional spatial array is one example of a spatial pattern. Since activity associated with each voxel is represented, a spatial pattern contains much more information than a single activity metric for the entire localized region. It is noted that a spatial pattern may be defined either in geometric space as physically measured, or may be defined in a transformed space or standard coordinate space intended to allow the geometric points in the brain of one subject to be aligned with anatomically or physiologically corresponding points in another subject or group of subjects.

Stimulus information, as used herein, refers to any information which when communicated to a subject may cause the subject to have a perception, and/or to alter activity in one or more regions of interest of the subject's brain. Examples of stimulus information include but are not limited to: displays of static or moving images, sounds, and tactile sensations. It should be recognized that certain types of information may perform a dual function of being stimulus information and also communicating another type of information.

Stimulus set or behavior set, as used herein, refers to a defined set of stimuli or behaviors that are to be used to activate one or more particular regions of interest of a subject's brain. The exemplars forming the set may constitute either a set of discrete exemplars (such as a set of digitized photographic images of faces, instructions, or words), or a continuum from which particular exemplars can be drawn (such as the sound frequencies from 2000-8000 Hz or visual gratings with spatial frequency from 0.01-10 cycles/degree of arc). As will be described herein, a set of exemplars may be used to identify a subset that are found to more effectively activate the particular one or more particular regions of interest.

Subject, as used herein, refers to a person whose brain activity is to be measured in conjunction with performing the methods of the present invention. It is noted that the subject is the person who has the condition being treated by the methods of the present invention.

Subject performance related information, as used herein, refers to any information relating to how effectively a subject is altering activity in one or more regions of interest of the subject's brain being targeted, for example, in response to the subject performing a behavior or having a perception that is directed toward altering activity in one or more particular regions of interest.

Substantially real time, as used herein, refers to a short period of time between process steps. Preferably, something occurs in substantially real time if it occurs within a time period of less than 10 seconds, more preferably less than 5, 4, 2, 1, 0.5, 0.2, 0.1, 0.01 seconds or less. In one particular embodiment, computing an activity metric is performed in substantially real time relative to when the brain activity measurement used to compute the activity metric was taken. In another particular embodiment, communicating information based on measured activity is performed in substantially real time relative to when the brain activity measurement was taken. Because activity metrics and information communication may be performed in substantially real time relative to when brain activity measurements are taken, it is thus possible for these actions to be taken while the subject is still in position to have his or her brain activity measured.

Task, as used herein, refers to a perceptual, cognitive, behavioral, emotional, or other activity undertaken by a subject, typically repetitively as part of a trial.

Treatment, as used herein, refers to the application of this invention to a subject with the intent of improving a condition of the subject.

Trial, as used herein, refers to a period of time that may include one or more rest periods and one or more instances or attempts to perceive a stimulus or perform a behavior. Trials may be typically repeated in blocks, and blocks may be repeated in sessions.

Training, as used herein, refers to the process of a subject perceiving a stimulus or performing a behavior in combination with having activity be measured of a region of interest to be activated by the perception or behavior.

Vectorized brain states, as used herein, refers to a measured state of the brain where the activity in each voxel of the brain may be separately measured, as in a spatial activity pattern.

Voxel, as used herein, refers to a point or three dimensional volume from which one or more measurements are made. A voxel may be a single measurement point, or may be part of a larger three dimensional grid array that covers a volume.

DETAILED DESCRIPTION OF THE INVENTION

The brain is the seat of psychological, cognitive, emotional, sensory and motoric activities. By its control, each of these elements may be controlled as well. Many psychological and neurological conditions arise because of inadequate levels of activity or inadequate control over discretely localized regions within the brain. The regulatory or neuromodulatory brain regions provide control over other brain regions. These regulatory or neuromodulatory brain regions cause many disease states when they fail to produce their intended regulation, and exogenous drugs often seek to re-apply this missing internal regulation.

The present invention provides methods, software, and systems that may be used to provide and enhance the activation and control of one or more regions of interest, particularly through training and exercising those regions of interest. An overview diagram depicting the components and process of the invention is presented in FIG. 1. As illustrated, a scanner and associated control software 100 initiates scanning pulse sequences, makes resulting measurements, and communicates electronic signals associated with data collection software 110 that produces raw scan data from the electronic signals. The raw scan data is then converted to image data corresponding to images and volumes of the brain by the 3-D image/volume reconstruction software 120. The resultant images or volume 125 is passed to the data analysis/behavioral control software 130. The data analysis/behavioral control software performs computations on the image data to produce activity metrics that are measures of physiological activity in brain regions of interest. These computations include pre-processing 135, computation of activation image/volumes 137, computation of activity metrics from brain regions of interest 140, and selection, generation, and triggering of information such as measurement information, stimuli or instructions based upon activity metrics 150, as well as the control of training and data 152, using the activity metrics and instructions or stimuli 160 as inputs. The results and other information and ongoing collected data may be stored to data files of progress and a record of the stimuli used 155. The selected instruction, measured information, or stimulus 170, is then presented via a display means 180 to a subject 190. This encourages the subject to engage in imagined or performed behaviors or exercises 195 or to perceive stimuli. If the subject undertakes overt behaviors, such as responding to questions, the responses and other behavioral measurements 197 are fed to the data analysis/behavioral control software 130.

Through the use of the present invention, a subject is able to be trained to control the activation of a region of interest of that subject's brain, and then exercise the use of that region to further increase the strength and control of its activation. This training and exercise can have beneficial effects for the subject. In the case of regions that release endogenous neuromodulatory agents, this control can serve a role similar to that of externally applied drugs.

The exercise of regions of interest according to the present invention is analogous to the exercise provided by specialized training equipment for weight lifting that isolates the activation of a particular set of muscles in order to build strength and control in those muscles.

In addition to training and exercise, knowledge of the activation pattern in discrete brain regions can be used to enhance certain aspects of a subject's behavioral performance, such as the subject's abilities at perception, learning and memory, and motoric skills. This enhancement takes place by cuing a subject to perform a behavior at a point when a measured pattern of brain activation is in a state correlated with enhanced performance. Alternatively, the behavior that the subject will undertake or the stimulus that the subject will perceive can be selected based upon the measured pattern of neural activation.

Methods have been described previously in the literature that correspond to measuring a physiological property, and presenting the measured result to the subject so that the subject can engage in biofeedback. The present invention differs substantially from those methods. As described above, biofeedback has been employed in conjunction with certain brain recording methodologies, namely EEG (U.S. Pat. Nos. 4,919,143, 4,919,143, 5,406,957, 5,899,867 and 6,097,981) and light (U.S. Pat. No. 5,995,857) to try to treat select brain disorders by allowing a subject to monitor his or her own brain functions (e.g., blood flow or blood oxygenation or tissue metabolism) as the subject attempts to alter a level of globalized brain function in response. These methods have typically been directed to monitoring of overall brain activity of the entire brain or large areas of the brain using signals such as EEG brainwaves, and thereby allowing the subject to view their own globalized activity level to try to learn relaxation, better attention, or control over another global process.

The present invention is substantially different from the prior art, focusing upon using the discretely localized measurements emanating from brain regions with very specific functions to control the stimuli and instructions presented to a subject. This control can be used in training and exercise methods directed specifically to the functions controlled by the regions of interest being measured.

As will be explained herein, any brain measurement methodology may be used in conjunction with the present invention so long as the physiological activity of one or more discretely localized regions of the brain can be effectively monitored in substantially real time.

In one particularly important embodiment that will be described in greater detail, the brain scanning methodology used is functional magnetic resonance imaging (fMRI).

In one variation, the regions of interest targeted by this invention are internal relative to a surface of the brain. By using brain scanning technology, such as MRI/fMRI that is able to make measurements from internally localized regions of the brain, the present invention is able to treat those internal localized regions of the brain. Some other technologies are limited because their measurements are made from surface points based upon current or voltage recorded at the brain or scalp surface, or based upon radiation emitted from the brain or scalp surface. A single signal emitted from any one localized brain region internal to the brain will propagate through the brain according to its conductivity to many points on the brain surface. This signal will be mixed with the signals from all other active brain regions as it propagates. Once mixed, this large number of competing signals cannot be completely separated based upon a finite number of surface measurements. Some analysis methods have attempted 'source separation approximations' to attempt to infer what point generated a given signal in the presence of many other signals, but none can completely and definitively determine the signal from a particular discretely localized brain region due to the underlying physics of the problem. This is based upon a limitation of the measurement technique: the electrical or radiation signal used to make the measurements is contaminated by the tissue through which the signal must pass to enter and exit the brain between the transmitter and the receiver, and by adjacent tissue.

A major advance in measuring the activity in discretely localized brain regions was the advent of brain scanning technologies, such as fMRI, PET, and SPECT. These technologies overcome the obstacle of measuring the activity in localized regions internal to the brain without substantial contamination from surrounding and intervening tissue. For example, an MRI/fMRI scanner uses a different magnetic field strength at each point in space, which corresponds to a different RF center frequency for measurement. MRI/fMRI is therefore able to make measurements from only a single point (based upon field strength) by recording RF at the relevant center frequency. This measurement is not significantly contaminated by activity from surrounding regions, or be regions between the point being measured and the surface of the brain.

By using brain scanning technology that can accurately measure internal localized regions of the brain, the present invention is able to monitor and treat internal, localized brain regions. This is an important distinction from merely controlling activity in the brain as a whole, or in a large brain region as a whole. The brain is a structure with hundreds of individual regions, some extremely small, and each with its own function. In order to control the brain's actions in a meaningful way, it is important to spatially localize which regions are measured, which regions are activated, and which regions are de-activated. This invention allows the control of small, discretely localized brain regions. This invention also allows the control of the pattern of activity within a brain region to create a 2-D or 3-D pattern of activation that can include sub-regions of increased activation and sub-regions of neutral or decreased activation.

This invention can employ measurements made using a scanning methodology that records data from each point in a predefined volume. In another variation, the localized brain region that is monitoried is as small as a single voxel. Taking measurements from a single point or small volume allows data collection to be concentrated on the single volume of measurement, rather than being divided across multiple measurement points across a larger volume. This also can obviate the need for elements of the technology that enable scanning of the measurement point.

The present invention may be applied to any disease or condition involving inappropriate activity in one or more discretely localized brain region. For example, the present invention can be used to address a decrease in activation of the substantia nigra that leads to a decrease in the release of the endogenous neuromodulator dopamine in Parkinson's disease with resulting changes in activation in target areas, the decrease in activation in the nucleus basalis of Meynert that leads to a decrease in the release of the endogenous neuromodulator acetylcholine to regulate the cerebral cortex in Alzheimer's disease, or the decrease in frontal cortical activity in Major Depression that can be positively impacted by increased release of the endogenous neuromodulator serotonin from serotonergic nuclei.

The present invention can also be applied to subject-specific conditions involving a decrease in activity within a particular discretely localized region, such as the decrease in activity in the still-living tissue adjacent to tissue destroyed by ischemic brain injury (CVA/stroke).

Examples of regions of interest of the brain which may be targeted according to the present invention include, but are not limited to those listed in FIG. 2.

The present invention is particularly well-suited for the treatment of conditions that have a cause directly related to an inappropriate level or pattern of neural activation within a discretely localized brain region. This is because the invention utilizes technology that allows these discretely localized brain regions to be directly spatially targeted, controlled, trained, and exercised.

The present invention is also particularly well-suited for the treatment of conditions positively impacted by endogenous neuromodulatory compounds emanating from localized brain regions. This is because this invention allows the regions that produce or respond to these compounds to be directly spatially targeted, controlled, trained, and exercised.

A feature of the methods, software and systems of the present invention is the communication to a subject through visual, auditory or other information, including measured information, instructions, or stimuli that are based upon the measured activity of discretely localized regions of his or her brain. This measurement can be based upon substantially real time brain scanning technologies such as functional magnetic resonance imaging (fMRI) or other physiological measurement methods. By measuring physiological activity levels of discretely localized regions of the brain and communicating instructions or stimuli that are based upon those activity levels to the subject in substantially real time, the subject is able to regulate, train, and exercise the physiological activity levels of those discretely localized regions of the brain.

A further feature of the methods, software and systems of the present invention is the identification of certain training exercises that the subject can use to regulate the physiological activity levels of those discretely localized regions of the brain. By first identifying what training exercises are most effective for a selected localized portion of a given subject's brain, the localized activation provided by the present invention is enhanced. Furthermore, by then performing the selected training exercise where the subject's effectiveness in activating the selected localized portion of the subject's brain is monitored and communicated to the subject, the effectiveness of the training exercise is maintained and improved upon.

By performing the methods of the present invention, desired levels and patterns of physiological activation can be achieved within regions of interest. Achievement of these levels and patterns can be used to achieve a variety of highly desirable results including, but not limited to, the treatment of a number of conditions or psychiatric or neurologically-based diseases, improvement in performance or learning, and improvement of mood or affect. For example, the methods allow monitoring and control over many aspects of neurological and psychological disease, as well as improvements in mental performance and improvement of psychological and emotional states and learning. A partial list of diseases or conditions which may be addressed by the present invention include, but are not limited to Parkinson's disease, Alzheimer's disease, depression, psychosis, epilepsy, dementia, migraine, others described in FIG. 3, and those described in:

Adams & Victor's Principles Of Neurology by Maurice Victor, Allan H. Ropper, Raymond D. Adams.

Different aspects of the present invention, including more specific methods, software, and systems are provided herein. The following paragraphs provide an overview of an embodiment of training and exercise according to the invention. Further embodiments and details are provided in the sections that follow.

One step toward providing treatment using this invention is to determine the primary region(s) of interest that mediates the condition to be treated so that treatment can be focused upon this region of interest. An initial set of stimuli or instructions for behaviors may be selected that will selectively engage the brain region of interest, and that may be used in training and exercise. It is also important to localize the region of interest within the brain of the subject using anatomical and physiological scanning methods. Once the region of interest is localized for the subject, particular stimuli or instructions for behaviors may be selected from the initially defined set to be used for training the subject. The stimuli or instructions for behaviors are typically selected that produce the highest level of activation of the brain region of interest during the particular stimulus or behavior.

At this point, training of the subject begins using the optimized stimulus set. The subject takes part in multiple training trials in training blocks. The training blocks take place within repeated or daily training sessions. The goal of the training is for the subject to gain increased control over the region of interest, and to exercise that region to achieve greater activation. The exemplar stimuli/behaviors isolate activation of particular brain regions, and the subject is given information about the progress of their training.

For a particular training trial, while inside the scanning apparatus the subject is given the instruction to observe a particular stimulus or engage in a particular behavior. For example, the subject receives the instruction to make a particular movement of the hand. The resultant activity level in the region of interest is measured by the scanning apparatus. This is analogous to an athlete lifting the weights on a particular weight-lifting machine using an isolated set of muscles. The subject is then given information about the activation that they were able to achieve, analogous to an athlete observing how much weight they were able to lift. Over training, the subject practices and exercises and gradually builds greater control and higher activation in the region of interest. Training typically takes place over a number of sessions on separate days. This training can be supplemented with additional training outside of the scanner (when the subject would not receive the information about their performance level) using the selected stimuli. The training can also be provided as an adjunct to additional therapies such as pharmaceuticals or physical therapy.

Additional embodiments are described in the examples section.

The detailed discussion that follows through section 6 describes aspects of an embodiment of this invention that allows training and exercise of a subject for the purpose of treatment of a condition through the regulation of certain brain regions.

1. Determining a Treatment Method for a Given Condition

This section describes a process by which treatment methods for different conditions may be developed. It is noted that the subjects referred to in this section are not necessarily subjects that are being treated according to the present invention. Instead, the subjects referred to in this section are people who are used to evaluate how well given stimuli, instructions for behaviors activate certain brain regions. Developing treatment methods for different conditions may be performed by evaluating a likely effectiveness of treating a given condition by understanding whether there is an association between a given condition and a particular brain region; determining the one or more regions of interest to be trained for the given condition; determining one or more classes of exercises likely to engage those brain regions; determining a set of exemplar exercises from the one or more classes for use in training; and testing the subject to ensure that the set of exemplar exercises are effective in activating the regions of interest.

A. Evaluating A likely Effectiveness of Treating a Given Condition

Numerous different conditions may benefit from training according to the present invention. For example, Parkinson's disease is caused largely by insufficient activity of the brain's substantia nigra, and resultant patterns of activity in its neural target zones. The activity in the substantia nigra and its target zones can be increased through training and exercise of this region of interest. In the case of stroke, regions adjacent to the zone destroyed by ischemia can be trained to achieve improvements in neural activation and regulation. Many other examples of conditions that may benefit from training according to the present invention are described in the Examples section herein.

The likelihood of success for a given condition to be treated according to the present invention can be evaluated from knowledge of the etiology and variety of causal factors contributing to the condition as understood at the time of treatment. More specifically, when considering whether treatment will be effective for a given condition, attention should be given to whether the condition is related to brain activity. If there is a correlation between the presence of the condition and a level or pattern of brain activity in one or more regions of interest, then, the methods of the present invention are likely capable of improving that condition by altering the level or pattern of brain activity in the one or more particular brain regions.

B. Determining One or More Regions of Interest to be Trained for the Given Condition As noted above, the brain comprises thousands of individual regions, each with its own function. Thus, in order to treat a given condition, it is important to identify the one or more regions of interest associated with the condition. It should be noted that the precise location of these regions can vary subject to subject. Hence, it is also important to identify the one or more regions of interest to be treated for a given subject. This ultimately makes the treatment methods of the present invention highly individualized.

Determining the one or more discretely localized brain regions to be trained for a given condition may be performed through a combination of general knowledge about what regions are associated with the given condition and thus need to be exercised, and information about the particular subject.

For a given condition, the scientific and clinical literature will typically have information regarding which localized brain regions are associated with the given condition. For example, the literature may have information associated with a given condition regarding human and animal neural lesion data, pathology, histochemistry, pharmacology, brain stimulation studies, neural recording studies, and functional and anatomical imaging studies. Using this information, one is able to take a subject with a given condition, and determine which brain areas are most relevant.

Once brain regions associated with a given condition are identified in the abstract, it is important to then identify these regions in a given subject's brain. It is noted that treatment will be performed over a period of several days, weeks, month or even years. Therefore, it is advantageous to store information regarding the location of the relevant brain regions for a given once they are identified so that less time and effort is needed to relocate them for subsequent treatments.

In the case of fMRI scans, the regions of interest can either lie within a single plane of section, or they can form contiguous or non-contiguous volumes consisting of regions on multiple planes of a section. Software allows the definition of standard-sized regions of interest, centered on a location selected by the device operator or based upon anatomical boundaries or measured physiological activation patterns. Once particular regions of the brain are identified for a given subject, the regions may be saved numerically to some form of memory (e.g., a computer disk) so they can be recalled for separate scanning runs, or for scans conducted in different sessions at later dates.

C. Determining One or More Classes of Instructions or Stimuli Likely to Engage the Brain Regions of Interest Different regions of the brain are associated with different functions, and may thereby be engaged and exercised by particular types of stimuli, or by particular behaviors associated with those functions. Hence, by understanding what function a given region of the brain performs, exercises can be designed which activate those brain regions. Through trial and error, exercises can be varied and thereby fine tuned both with regard to their effectiveness in activating a given region in general, and with regard to their effectiveness in activating a given region for a given subject.

Numerous physiological studies on many different brain regions have been performed and have yielded a wealth of information regarding the different kinds of stimuli or behaviors that can be used to engage different specific brain regions. Many areas of the brain have already been 'mapped' in their functionality, in that particular zones are activated by particular types of stimuli or behaviors, with adjacent zones activated by similar stimuli or behaviors. These types of studies have allowed for the determination of what classes of stimulus or behavior are likely to activate particular brain regions by selecting the stimulus or behavior that are appropriate to the type of map and the point on the map being considered.

For example, countless detailed studies have determined frontal cortical regions that subserve movements, the motor cortex. Thus, a lesion that partially inactivates the cortical hand representation will destroy tissue engaged in hand movements. Adjacent tissue will be involved with the other hand, wrist, and arm movements. Therefore, in order to treat the lesion, exercises to employ will include exercises that engage the brain region where the lesion is located as well as adjacent regions. In this instance, such exercises will likely encompass movements of the relevant extremity, whether physically or mental thoughts of their movement.

D. Determining a Set of Exemplar Instructions or Stimuli from the One or More Classes of Examples Once a general class of exercises has been determined for a given region of the brain, actual instances of specific stimuli or behaviors are created that are able to exercise the brain region of interest.

The stimuli or instructions for behaviors to be used may be created from within the class of stimuli or instructions for behaviors that will engage the brain region of interest. The exemplars created may be real stimuli that will be presented to subjects, or real instructions that will lead the subject to engage in behaviors. These stimuli and instructions may be created via computer to be presented digitally. Visual stimuli may be presented on a monitor viewed by the subject, auditory stimuli may be presented via speakers controlled by a computer, and tactile or other sensory stimuli may be presented via computer-controlled sensory stimulation devices as needed. For example, in order to engage certain regions of the temporal lobe involved in the processing of faces, a set of digitized photographic images of faces is used. In order to engage the primary motor cortical representation of the hand, a set of digitized images or movies depicting particular hand movements is uses. Typically, the stimuli to be presented can be based on stimuli that have previously been demonstrated to be successful in activating the brain region of interest.

Instructions can include text instructions that will inform the subject of what to do and be presented either on the monitor, or they can include verbal instructions presented via digital audio, or the instructions can include icons or movies presented to the subject.

E. Testing Subjects to Ensure that the Set of Exemplar Instructions or Stimuli are Effective In many instances, the process of creating stimuli or instructions for behaviors is iterative, with the initial stimuli or instructions for behaviors created needing to be fine-tuned. This may be performed by first determining the appropriateness of the stimuli or instructions for behaviors by testing them against subjects. It is noted that this is an objective evaluation of the effectiveness of the behavioral instructions or stimuli. This evaluation can be used for the subject(s) with which it was determined, or for other subject(s).

Typically, the stimuli or instructions for behaviors are presented in the context of a psychophysically controlled task or measurement or an operant conditioning task. The subject is asked to detect the stimuli or make discriminations among them when they are presented using computer-controlled software, or asked to perform the behaviors. This allows the stimuli or instructions for behaviors to be optimized to be close to the subject's behavioral ability threshold, or ability to detect or make discriminations among them. Stimuli are often selected that are slightly harder to detect or discriminate than the subject can achieve, similar to what the subject can achieve, and easier than what the subject can achieve. Suprathreshold stimuli can be used as well to ensure the subject's success in detection or discrimination. Similarly with movements, cognitive, or other behaviors, behaviors are selected based upon a subject's ability to perform them up to a certain level of speed, accuracy, or performance ability.

The physiological responses for the stimuli selected can also be evaluated using pre-testing. In this case, the stimuli or instructions for behaviors are presented to subjects while the subjects are in a scanning apparatus, and tested for their efficacy in engaging the regions of interest. As will be described below for individual stimuli and instructions for behaviors, it is possible to determine which are most effective and then 'fine-tune' to generate classes with the best characteristics in terms of their ability to activate a given brain region. As an example, flashed or reversing visual grating stimulus classes can be optimized to have spacings between the gratings and flash rates that drive the largest physiological responses.

2. Pre-Training a Subject

Once a treatment method has been determined for a particular condition, as described in the preceding section, subjects with that condition may be treated. Prior to treatment, it is advantageous to first evaluate whether a particular subject is suitable for treatment based upon defined selection criteria; explain the training process in detail to the subject; and then pre-train the subject using a simulated training environment.

A. Defining Subject Selection Criteria and Screening Subjects

It is desirable for the treatments of the present invention to have a high frequency of success. It is therefore desirable to select subjects based upon the likelihood of their treatment being successful.

Examples of selection criteria that may be used include but are not limited to:

1) Whether the subject has the condition for which treatment is intended, based upon standard diagnostic criteria.
2) Whether the subject has other, preferable treatment options available.
3) Whether the subject has sufficient cognitive ability to participate in training.
4) Whether the subject has any contraindication for brain scanning, such as phobias relating to being inside a scanner, or in-dwelling metal objects such as a pacemaker, or movement disorders that would hinder the ability to make prolonged, stationary brain scans.
5) Any indicators predictive of treatment success, such as previous success of the method with subjects that are similar based upon diagnostic group or other signs and symptoms.

Each potential subject may be screened based upon some or all of these selection criteria to determine their suitability for treatment.

B. Subject Pretraining

It is advantageous to explain the training process to the subject before training takes place in combination with a brain scanner to measure brain activity. Optionally, the subject is pre-trained using a device that simulates the experiences that the subject will experience when actual training is performed. This may include providing the subject with the same or similar visual and auditory experiences that will later be provided. For example, when graphical interfaces are to be employed, it may be desirable to pretrain a subject using those graphical interfaces, or at least show the subject the graphical interfaces he or she will see and explain their components.

The details and purpose of the training are explained to the subject to allow him or her to be intimately familiar with what he or she will be doing. A number of issues may be explained including: that the goal of training is for them to be able to increase the control over a particular brain region and then exercise the activation of that region; the importance of being still during the scanning session; the importance of behaving in a similar way each trial and avoiding excessive physiological activity such as deep sighs so that measurements are consistent; the types of exercises that are likely to succeed in activating the brain region of interest.

A subject may also be given detailed descriptions and explanations of the functioning of the brain regions of interest; of the measurement technology being used; of the time-course of physiological activity changes; of how to communicate with the controller; and so on.

A subject may also be trained regarding how to determine what mental, perceptual or physical activities produce the greatest response in the brain region(s) of interest by observing the information that he or she will receive regarding their activity metrics, and how to generate mental, perceptual or physical activities that are likely to produce the desired modulation.

The direction provided to a subject is important in the sense that the subject is not asked to attempt to figure out how to increase the level of physiological activity using any means he or she devises. Rather, it may be explained to the subject that their mental activities lead to very specific patterns of brain activation, and that the goal is to find the activities that lead to the greatest pattern of activation in the region of interest, and then increase this level of activation through successive practice. It may also be explained to the subject that merely trying to increase the level of activity in a particular brain region in a general way is unlikely to succeed, or will likely succeed very slowly. Instead, it is by the activation of specific localized regions of the brain by carefully tailored exercises that the results achievable by the present invention are provided.

It is also explained to the subject that neural responses are highly variable, so it is important for them to repeat a given behavior a number of times and observe a number of the resultant responses to get an accurate sense of the response derived from that behavior. In addition, physiological responses may take some significant latency to be measured after the subject initiates a behavior, such as up to 5-10 seconds for some blood-flow-based measurements. Therefore, it is explained to subjects that the relevant signal corresponding to a given perception of a stimulus or performance of a behavior will only become apparent after a delay.

In regions where a clear behavioral strategy for controlling a brain region is not be determined in advance, but to be determined during the course of training, a subject should be instructed on how to go through a clear process of determining what behavioral strategy works, and then refining it. This strategy is analogous to defining the tuning curve or optimal stimulus for a brain region, and involves repeatedly measuring the resultant activity from a broad range of stimuli or behaviors in order to determine which ones lead to the largest activation on average with some latency.

A subject is preferably pre-trained using exercises that closely mimic the exercises that will be performed when the brain activity is being measured. This allows the subject to become familiar with and practiced on the exercises that he or she will be completing. In addition to ensuring that the subject has a clear understanding of what he or she is to do, this allows any habituation of neural responses to the training activities or other early learning effects to approach steady-state.

A subject may also be trained using a simulation device that mimics the user interface and training schedule and uses the same selected stimuli that a subject would encounter during training in the scanning apparatus. This interface and its functioning will be described in detail below.

In pre-training simulation, because brain activity is typically not being measured, the subject being trained to perform mental exercises and observe stimuli is not given information regarding his or her patterns of neural activation that will otherwise be given during actual training, as described below. Optionally, however, the subject may be given simulated patterns of neural activation, such as those derived from past training sessions with the same or different subject, or using a random noise source or some other model of actual neural activity. The subject may also receive behavioral feedback alone, in the absence of simulated neural feedback.

Overall, pre-training is typically preferably designed to generate an experience as close as possible to the real training that the subject will undergo. Therefore, the training tasks that the subject is asked to perform, the percent correct achieved, the displays that are provided, stimuli that the subject experiences, and actions that the subject undertakes are all preferably similar to those the subject will observe when actual training is performed.

3. Initial Brain Scanning Setup and Performing Scanning

Before beginning training using this invention, a number of aspects of the invention must be prepared for use. These include preparing the graphical user interface, preparing the subject within the scanning apparatus, and setting up for anatomical and physiological scanning. Section 3 lays out many of the aspects of what the invention does in general, while describing the setup of the various components. In particular, it describes all of the computations that we can make, and the displays that we can generate. Later sections then tell us what we actually DO in training, and give detailed examples of the computations and displays.]

A. Preparation for Brain Scanning

Once a subject has been trained, the subject may be introduced into a scanning apparatus where measurements of brain activity are taken and the location of targeted localized regions of the brain are identified. This section describes this process in regard to a magnetic resonance imaging scanner, such as a GE 3.0 T Signa MRI scanner. How to perform analogous scanning using other instruments would be understood by one of ordinary skill in the art.

i. Preparation of Subject within the Scanning Equipment

In order to take measurements of localized region of the brain, the subject of course has to be properly positioned relative to the scanner. Placement is made to ensure standard positioning, to help ensure that the subject has a positive and comfortable experience, and to ensure that the subject has access to visual and other stimuli as well as output devices. The subject is 'landmarked' by measuring the position of the nasion (bridge of the nose) using the scanner and setting this to a standard zero position, from which measurements will be taken. The subject's head is placed within a coil, such as a dedicated head coil. The coil is selected to give the best signal from the region of interest. The subject is given earplugs or sound cancelling headphones to decrease noise within the scanner. Communication equipment may also be setup between the subject and the device operator or other healthcare professionals in attendance.

ii. Head Motion Stabilization and Physiological Gating

As would be expected, it is desirable that the subject's head remain perfectly stationary. In order to decrease head motion, the subject may be placed within an adjustable or custom-made head motion stabilizer that is secured to the scanner. If additional motion stabilization is required, motion stabilization software, may be used to correct data volumes collected for movements of the subject within the scanner. An example of this software is described in C C Lee, et al. Real-time adaptive motion correction in functional MRI. Magn Reson Med 1996; 36:536-444. In instances where a structure is being measured that is subject to significant physiological motion, the timing of initiation of successive measurements may also be triggered to correspond with a particular phase of the cardiac or respiratory cycle according to standard methods described in the literature.

iii. Brain Volume Registration

In order for the position of the head and the related measurements to be comparable from session to session, images and volumes should be registered, allowing precise correspondence of voxels across days. This volume registration can have a manual component and an automated component. In the manual component, the subject is positioned within the scanner in a stereotyped way to try to achieve similar placement on successive occasions using a bitebar and fixed points of reference within the scanning apparatus. Additionally, the zero point for scanning may set to the nasion of the subject (bridge of the nose) using a standard light beam approach built into the scanner. Finally, scanning sections are prescribed relative to fixed anatomical landmarks within the subject, including but not restricted to the anterior commissure, the posterior commissure, the mid-saggital line, the central sulcus, the temporal pole, the calcarine fissure and pole, and the topmost point on the cerebral cortex. If sections are prescribed in three dimensions based upon the accurate positions of at least three anatomical landmarks on the subject, then the positions of brain regions can be reliably reproduced on successive sessions. Scanning sections can also be prescribed relative to fiducial marks placed on the subject using material opaque to a scanning instrument. If these marks are placed on known locations on the subject, then they can serve as landmarks for scanning.

B. Anatomical Scanning

Anatomical scans of the subject may be made using an imaging apparatus to visualize internal brain structures. In one embodiment, detailed anatomical images are collected using an MRI scanner. In one particular example, whole-brain imaging data are acquired on a 3 Tesla MRI Signa LX Horizon Echospeed scanner (General Electric Medical Systems, 8.2.5 system revisions) as described in the operating instructions for that instrument. For example, T1 and/or T2 weighted anatomical image data are collected from axial slices through the head which will be in substantial register with physiological data collected later. An embodiment collects 17 axial slices of 7 mm slice thickness, with each slice having a 256×256 voxel resolution over a 22 cm×22 cm area, producing 256×256×17 voxel brain volume data. Higher resolution data may be collected as well to allow more detailed anatomical localization by changing the number of voxels in each of the three dimensions. MRI anatomical scanning methods are described in detail in neuroanatomical texts.

C. Physiological Scanning

An aspect of the present invention relates to the performance of brain scanning such that the physiological activity of regions of interest of the brain can be measured and monitored. It is noted that such measurements and monitoring is preferably performed in substantially real time so that computations can be performed and resultant information including measured information, stimuli, and instructions can be frequently relayed to the subject in a timely fashion to influence how the subject performs training exercises.

i. Measurements

Physiological activity measurement may take one or more of several forms, including fMRI BOLD signals, fMRI EPI signals, PET or SPECT signals, or event-related signals conditioned on sensory events/motor behaviors, or other physiological measurements. These measurements may be made using a variety of physiological recording apparatus. Examples of measurement apparati that may be used alone or in combination include, but are not limited to functional magnetic resonance imaging (fMRI), PET, SPECT, EEG (electroencephalogram) recordings or event-related electrical potentials, MEG recordings (magnetoencephalogram), electrode-based electrophysiological recording methods including single-unit, multi-unit, field potential or evoked potential recording, infrared or ultrasound based imaging methods, or other means of measuring physiological states and processes.

Functional magnetic resonance imaging (fMRI) is a particular example of a brain scanning technology that is capable of measuring and monitoring brain activity in substantially real time. fMRI is based upon changes in Blood Oxygen Level Dependent (BOLD) contrast and provides spatially and temporally resolved visualization of the hemodynamic response evoked by neuronal activation. fMRI scanning can be performed according to widely published procedures. This technique has been described in detail elsewhere including for example in Annu. Rev. Biomed. Eng. (2000) 2:633-660, the references included therein, and An Introduction to Functional Magnetic Resonance Imaging: Principles and Techniques by Richard B. Buxton (Hardcover—November 2001).

In one particular example, whole-brain imaging data may be acquired on a 3 Tesla MRI Signa LX Horizon Echospeed scanner (General Electric Medical Systems, 8.2.5 system revisions) as described in the operating instructions for that instrument. Functional images may be acquired in the same slices as previously collected anatomical images (see above) using T2*-sensitive gradient echo spiral pulse sequence (30 ms TE; 1000 ms TR; 70 degree flip angle; 22-cm FOV; 64×64 acquisition matrix or similar parameters). See for example: Neuroimaging at 1.5 T and 3.0 T: comparison of oxygenation-sensitive magnetic resonance imaging. G. Kreger A. Kastrup G. H. Glover, Magn Reson Med. April, 2001; 45(4):595-604; Three-dimensional spiral fMRI technique: a comparison with 2D spiral acquisition. S. Lai G. H. Glover, Magn Reson Med. January, 1998; 39(1):68-78. The physiological images collected are registered with previously acquired anatomical images by lining the images up voxel-for-voxel. A more thorough fMRI scanning protocol is provided in Section 7 in the Examples.

It is noted that although many of the more detailed descriptions provided herein are directed to fMRI, it should be understood that the present invention may be used with any brain activity measurement technology that is capable of detecting activity in discretely localized brain regions. Over time, it is anticipated that new techniques will be developed with the ability to detect activity in discretely localized brain regions. Furthermore existing measurement technologies may be adapted for detecting activity in discretely localized brain regions. All such measurement technologies, and their combinations, are intended to be employable in conjunction with the present invention.

Once the scanning equipment is setup, physiological activation of the brain is measured. Generally, the process may comprise collecting scan data repeatedly (e.g. continuous collection at one scan per second), reconstructing the raw physiological data into image data in substantially real time, and performing computations on the resultant images as depicted in FIG. 1.

Activity patterns may be measured within regions of interest or for the whole brain, either at a point in time or continuously. This is achieved by scanning the imaging technology sequentially over a number of voxels with some sampling rate, taking measurements from each one. This gives indications of the level of physiological activity at each location at each point in time.

The number of different points that may be monitored will typically decrease as the sampling rate is increased once the operational limits of the equipment is reached. Therefore, it is frequently necessary to specify the locations and sizes (in three dimensions) of the regions of interest to be monitored, as well as the rate at which these regions of interest are to be sampled. These regions of interest may form either a large and contiguous array (such as a cube containing a large number of contiguous voxels), or a number of discrete locations that are one or more voxel in size. The measured values used for the regions of interest can involve time or spatial averaging or other mathematical smoothing of data over a range of samples. In this way, a vector of data may be acquired at each time point, and a larger vector consisting of a time series of data may be collected.

In order to collect scan data, the functional scanning parameters are input. Preferably, the parameters are pre-set, for example using control software incorporated into the instrument. Aside from inputting the functional scanning parameter, other things to check prior to initiating scanning include: informing the subject that the scan is about to begin, insuring that there is adequate data storage space available, and checking that all computer linkages are active.

ii. Scan Voxels, Scan Volumes, and Regions of Interest

As described in the definitions, a voxel refers to a point or three dimensional volume from which one or more measurements are made. Using a suitable scanning methodology, measurements may be collected from a large number of voxels. For example, measurements may be made from each component of a square grid volume of voxels corresponding to a scan volume. This scan volume may be positioned to include some or all of the brain of a subject. In this way, measurements may be made that span the entire brain, or a portion of the brain. Measurements may be made for each voxel in the scan volume at every measurement time. Measurements may be repeated, such as once per second or at other sampling rates. This may produce a full volume image of the activity level of each point in the brain each second.

In many instances, analyses according to present invention are based on a particular subset of volumes from among the entire scan volume. The particular subset of volumes may be the region of interest for that analysis.

A region of interest may include a selected one or more of the voxels or measurement points. A region of interest may have a spatial shape and extent defined by the voxels that it includes within the entire scan volume. A typical region of interest may be a 5×5 voxel square array, or a 5×5×5 voxel cubic volume, centered on a selected voxel. A process for selecting a region of interest is described in section 4. Since a region of interest may be comprised of multiple voxels from which independent activity measures are made, it may be possible to measure either an aggregate average level of activity from the entire region of interest, or a spatial pattern of activity comprising the activity at each voxel within the region of interest.

Measurement data may also be collected from a single voxel. In the case of collection of data from a single voxel, the one voxel may correspond to the region of interest.

D. Processing of Scan Data into Images and Metrics in Substantially Real Time

FIG. 1 illustrates the process flow diagram for taking raw scan data and producing information that may be communicated to the subject. As illustrated in FIG. 1, raw scan data is converted to image/volume data 125 corresponding to images and volumes of the brain by 3-D image/volume reconstruction software 120. These are referred to as image/volume data, or as images/volumes, to connote the fact that either a single planar image may be used, or a 3-D volume may be used. One of the simplest types of vector representation of physiological activation for the images is a planar section of fMRI activity, taken with some temporal resolution, and some spatial resolution. This provides a single slice image of the state of activation of the brain at a particular instant.

The resulting image/volume data 125 can then be used by the data analysis/behavioral control software 130, which is described in more detail herein. The data analysis/behavioral control software 130 generates information and selects stimuli or instructions to communicate to a subject 190 to influence how the subject performs training exercises. This takes place via three steps, each serving to generate the input to the next: 1) pre-processing of data, 2) computation of activation image/volumes, 3) computation of activity metrics, 4) generation of information for the subject such as measured information and selection of stimuli or instructions.

All of the computed values, such as those described in this section, may be stored to computer memory or a computer storage device for later retrieval. This storage may take place each time computations for a given measurement time point are completed, or it may take place at the end of a trial, or at the end of a training block or session. In addition, all of the computed values may be transmitted via the internet or other communication means at the time of computation, or at a later time.

The process illustrated in FIG. 1 will now be described in relation to processing fMRI data. It is noted that analogous data processing may be performed for other data from other types of instrumentation. Detailed examples of processing that may be performed are provided in Examples section 1.

i. Scanner Software

Commercial data collection software 110 is available and typically included with an MRI/fMRI scanner to control the process of initiating scanning pulse sequences, collecting measurements, communicating electronic signals associated with a scan, and producing raw scan data from the electronic signals. The raw data may be in the form of a k-space representation that can be accessed either from computer memory or from a disk file. This representation must be reconstructed to produce a spatial representation of the signal, such as a scan image or volume.

ii. Reconstruction Software

Once the output raw data is formed from the data collection software 110, this data serves as the input to the 3-D image/volume reconstruction software 120. The 3-D image/volume reconstruction software 120 performs computations upon this input that result in the output of 2-D scan images or 3-D scan volumes.

Converting the data to 2-D and 3-D scan images in substantially real time may be performed using reconstruction software. The reconstruction software may be conceptually similar to the software that performs offline k-space to volume reconstruction, with the distinction that it may run more efficiently and thus may be able to perform the necessary calculations in substantially real time.

The reconstruction software 120 can take several forms, which are publicly described and available. There is a substantially real time data analysis package produced and commercially available from Brain Innovation, Inc. Maastricht, The Netherlands. There are many instances of substantially real time reconstruction software described in the literature, for example: Functional magnetic resonance imaging in real time (FIRE): sliding-window correlation analysis and reference-vector optimization. D. Gembris J. G. Taylor S. Schor W. Frings D. Suter S. Posse. Magn Reson Med. February, 2000; 43(2):259-68; Goddard, N. H., Hood G., Cohen, J. D., Eddy, W. F., Genovese, C. R., Noll, D. C. and Nystrom, L. E., "Functional MRI Datasets Analyzed Online", in *Parallel Computing for Industrial Applications*, ed. A. Koniges (Morgan Kaufmann: in press)., Real-time image reconstruction for spiral MRI using fixed-point calculation. J. R. Liao IEEE Trans Med Imaging. July, 2000; 19(7):690-8. Real-time interactive MR imaging system: sequence optimization, and basic and clinical evaluations. S. Naganawa T. Ishiguchi T. Ishigaki K. Sato T. Katagiri H. Kishimoto T. Mimura O. Takizawa C. Imura, Radiat Med. January, 2000; 18(1):71-9. Real-time 3D image registration for functional MRI. R. W. Cox A. Jesmanowicz. Magn Reson Med. December, 1999; 42(6):1014-8. Fast "real time" imaging with different k-space update strategies for interventional procedures. M. Busch A. Bornstedt M. Wendt J. L. Duerk J. S. Lewin D. Gronemeyer J Magn Reson Imaging. January, 1998; 8(4):944-54.

In one embodiment, the process of taking the data and converting it to 2-D and 3-D scan images is performed one or more times every 10 seconds, optionally at least every 5, 4, 2, 1, 0.5, 0.2, 0.1, 0.01 seconds which is referred to herein as "substantially real time." This allows the scan images and/or information garnered from the scan images to be processed, with the results communicated to the subject to influence how the subject performs training exercises. It is noted that as processor speed continues to improve, and more efficient software is developed, faster and faster turn around times will be made possible and may be performed by the present invention.

In one embodiment, the resulting output image files from the transformations are flat, header-less files containing 64×64×17 2 byte integers corresponding to values for the voxels for each scan volume. The output image/volume data from the reconstruction software is then passed as one input to the analysis and control software.

iii. Pre-Processing of Image/Volume Data

One function that the data analysis/behavioral control software 130 may perform is to pre-process 135 the input data. It is noted that the software may optionally process the input data without preprocessing.

Once optionally pre-processed, the data may be used to compute activity metrics from image or volume data. These activity metrics may then be used to generate information to present to the subject, and make selections of stimuli or instructions.

The output images generated by the 3-D image/volume reconstruction software 120 are typically transferred to a separate computer that contains the data analysis/behavioral control software 130. Because it is desirable to relay information to the subject as soon after brain scan measurements are taken, this transfer preferably takes place by reading the stored data files containing individual scan volumes from the reconstruction computer using an NFS protocol. The format of these data are transformed if necessary to allow compatibility between computers, and they are read into memory by the data analysis/behavioral control software 130 on the substantially real time control computer in substantially real time. This process can also take place on a single computer if it has sufficient processing power.

Many types of pre-processing of image/volume data are available, and examples are described in detail in Examples section 1.A. As one example embodiment, the images may be simply spatially smoothed by convolving each image with a 2-D gaussian filter with a 1 pixel half width. The output of the pre-processing step is an image or volume of pre-processed data at every data collection time. This is similar in form to the input to this step, but transformed by the pre-processing computations.

iv. Computation of Activation Images/Volumes

Taking the images/volumes as input, optionally after they have been pre-processed, the next step is to compute activation images/volumes. This is typically performed by the data analysis/behavioral control software 130. Many types of activation images/volumes can be computed, and examples are described in detail in Examples section 1.B. below. These activation images/volumes can be used first to determine the location of a region of interest for a particular subject, and later as the input for making measurements from this region of interest.

An example activation volume that may be computed for the purpose of determining the location of the region of interest in a subject is a % BOLD difference image, computed taking preprocessed scan volumes as input by taking the value at each voxel from scan data at the current time and subtracting the value for an early slice, for example the 5th scan volume collected. This result is then divided by the value at the early slice, for example the 5th scan volume, and multiplied by 100%. The result is a % BOLD difference image that indicates the level of activation relative to the early scan volume.

v. Computation of Activity Metrics

Once activation images/volumes have been computed, it is possible to use these as inputs to the computation of activity metrics. This process involves computations of values from a defined region on the activation images/volumes that have been measured. Many types of activity metrics can be computed, and examples are described in detail in Examples section 1.C. below. For example, an average value of the activation for all of the voxels within a region of interest may be computed. In this case, the activation volume data for each voxel in a defined region of interest at each time point are used as input, and an average value of the activation is calculated for each time point for the group of voxels. This average may then be displayed to the subject or device operator using a graphical user interface described in the next sections.

E. Setup of Graphical User Interface

An important aspect of the present invention relates to employing measured brain activity to provide measured information, stimuli, or instructions to subjects that may be used to influence how the subject performs training exercises. This influence may be provided by having the subject interact with devices designed to be used in combination with this invention. A variety of interaction mechanisms are envisioned, some of which are described in detail in the examples section. Others will be appreciated by one of ordinary skill.

One primary type of display that may be presented to a subject or device operator in substantially real time include measures of physiological activity such as activation maps of the subject's brain activity, activity metrics from localized brain regions. Another primary type of display is stimuli that the subject will perceive that may be useful in activating certain brain regions and performing training. Another type of display may be instructions to the subject. The setup of the user interface and its potential components are described in the following sections.

i. Presenting an Overall User Interface to the Subject and Device Operator

Figure 4:
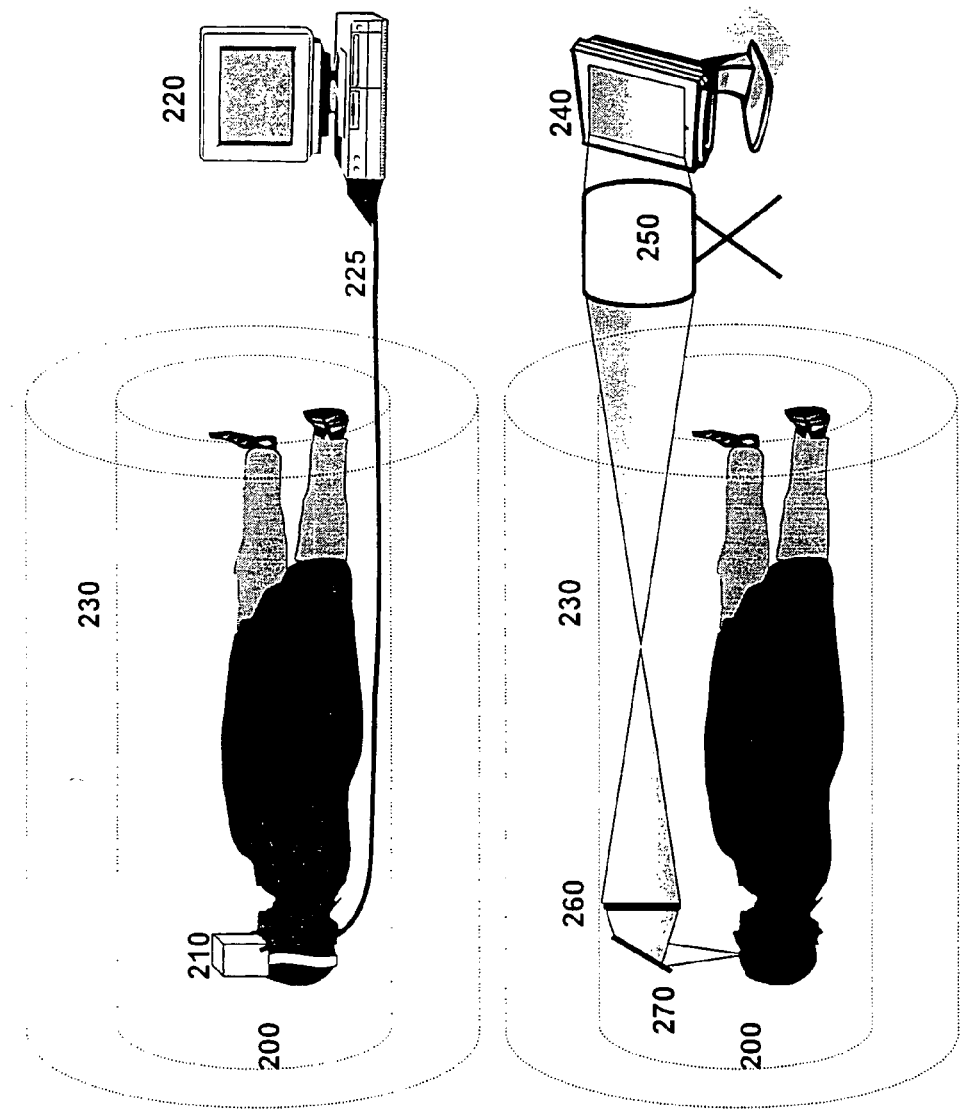
FIG. 4 is a diagram of methods and apparatus for displaying information to a subject in a measurement apparatus.

In one embodiment, as shown in FIG. 4, a subject 200 views information such as measured information, stimuli, or instructions using viewing goggles 210, such as virtual reality goggles, controlled by a computer 220 connected by a cable 225, while the subject is inside the bore of a scanning apparatus 230. Viewing goggles for the purpose are manufactured by Resonance Technology, Inc, California. The device operator may view a similar screen on a second display. In addition, a remote participant may view a similar display on a remote display screen. Information for remote displaying may be conveyed electronically, for example using a wire, wireless, or internet connection. The display presented for the device operator may be separately configurable to contain a different set of panels than that displayed to the subject.

In another embodiment, the subject 200, views and image displayed on a display 240 and projected through a lens 250 onto a reverse-projection screen 260. The subject views the screen through a mirror 270.

Using some form of display, the subject views instructions of what the subject is to do, information indicating the physiological activation of the subject's brain in substantially real time, indicators of the subject's success and progress in training, and/or other forms of information such as the number of trials remaining in a training session.

A variety of types of information and display screens can be presented. For example, visual stimuli may be presented to the subject via some form of display. FIG. 4 illustrates one such display system. When the subject sees the stimuli, associated changes in the brain of the subject will be observed. The many types of information that may be displayed are described below after the information that they will contain has been described. Auditory stimuli may also be presented to the subject, such as digitized speech, tones, music, or other types of sounds. Auditory stimuli may be presented to the subject via some form of speaker system, optionally worn by the subject. Tactile stimuli may be presented using a tactile stimulation apparatus such as a Chubbock stimulator or other tactile stimulator as described in: A tactile air stimulator for humans. E. W. Wineman, Psychophysiology. November, 1971; 8(6):787-9. Temperature stimuli may be presented using skin heating or cooling probes. Olfactory stimuli may be communicated using a device designed to present gaseous odors to the subject in the scanner, as for example described in: Time course of odorant-induced activation in the human primary olfactory cortex. N. Sobel V. Prabhakaran Z. Zhao J. E. Desmond G. H. Glover E. V. Sullivan J. D. Gabrieli J Neurophysiol. January, 2000; 83(1):537-51. When the subject receives any of these stimuli, associated changes in the brain of the subject may be observed. These changes may then be measured as has been described.

ii. User Interface Screens

Figure 5:
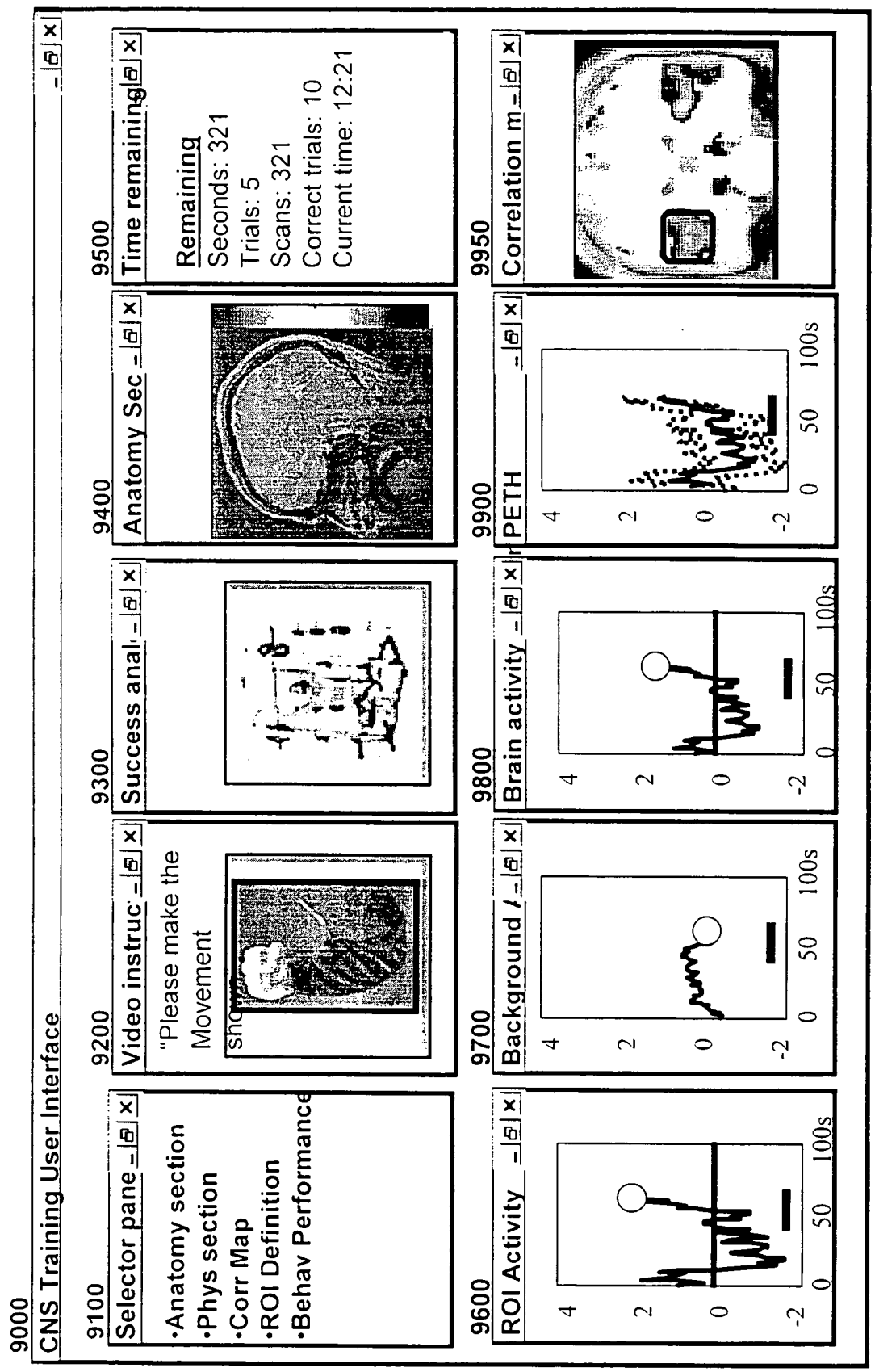
FIG. 5 is a table of functional MRI scanning parameters.

The subject and device operator may view a display a screen 9000 depicted in FIG. 5. This screen may contain a large variety of elements that can be selected for display, or hidden from view, and may each be appropriately sized to be visible in adequate detail. The screen may contain a sector panel 9100 that contains a list or set of graphical icons representing the other panels that may be displayed. Both the device operator and the subject are able to make selections from this selector panel 9100 using a pointing device such as a mouse. When a panel has been selected, it becomes visible on the screen, and the subject or device operator can use the pointing device to select the position and size of the panel on the screen. The user may select one or more of each type of panel to display. In some cases, the same type of panel may be displayed more than once for different purposes, such as the use of two anatomy panels, one to show a coronal section, and one an axial section.

iii. Presenting Images and Information

Data obtained and processed from an fMRI or another physiological activity measurement apparatus may be presented in substantially real time either to the subject of whom the fMRI scan is being taken, to the device operator, and/or another professional that is present, such as a doctor, nurse, technician.

The information displayed can include anatomical brain images, as well as physiological activation images/volumes, and activity metrics. The results of all of the computations described in section 3.D. above may be used as input to present image and metric data to the subject or device operator. One skilled in the art will recognize possible modes of display for each of the types of computed information described.

FIG. 5 shows several examples of the presentation of image and metric data, such as several activity metrics from the region of interest 9600, an alternate region of interest 9700 and the difference 9800, a PETH from the ROI averaged over several trials 9900, and a physiological correlation map 9950 indicating the brain areas activated by a trial and showing the region of interest.

These display may all be used to inform a subject of their physiological activation. This information can be used by subject while they are still in the measurement device to guide their performance or training. As subjects view the level of activation caused by particular strategies, stimuli, or behaviors, they can select how to behavior during the current trial or on forthcoming trials to improve their performance.

Further detailed examples of the types of information that may be presented and their uses are described in Examples sections 1, 2 and 3.

iv. Displaying Information and Instructions

In order to influence a subject's performance of trials and training, information may also be presented via a display, such as measured information, stimuli, or instructions. This information may include indications of the subjects success in training or performance targets. This display may also include instructions for the subject, such as to undertake a particular type of trial, or achieve a particular performance target. FIG. 5 illustrates a video instruction for a subject to make an indicated movement 9200, and a success analogy indicating to the subject the level of activation achieved in a brain area being exercised in the form of a visual analogy.

Again, detailed examples of the types of information that may be presented are described in Examples sections 1, 2 and 3.

4. Localizing Brain Regions of Interest in a Subject

In order to select the area on which measurements may be focuses, different methods may be used to localize a region of interest. These methods include anatomical methods for localizing structures, and physiological methods for determining volume activated by a given stimulus or behavior. A region of interest normally corresponds to a subset of the full scan volume that may be collected at each measurement time point. These voxels are selected because of their importance in measurement or training. The voxels within a region of interest may be defined in a number of ways. They may be defined to be within the anatomical boundaries of one or more brain regions as determined through anatomical scans. They may be defined by the fact that they are activated in correlation with a stimulus, behavior or task. They may be defined arbitrarily by the device operator using a selection screen that allows the device operator to select individual voxels or regions of interest. They may be defined stereotaxically or by adjusting the position of the patient within the measurement apparatus in such a way that the apparatus measures activation from a defined point or area within the subject. The primary region of interest is normally the area that is being trained, and that the subject is attempting to modulate activation within. Comparison regions of interest are other defined regions that may be compared with the primary region of interest, such as other parts of the brain that are not intended to be activated by the task. A region of interest or volume of interest need not be spatially contiguous. For instance, a region of interest might constitute the substantia nigra and sub-thalamic nucleus on both sides of the brain, four non-spatially-contiguous volumes.

A. Anatomical Localization of Brain Regions of Interest

Once anatomical data has been collected for a subject, anatomically defined brain regions may be localized for the subject with reference to the collected anatomical information using either reference to a standard anatomical atlas, or using a manual search. In either case, positions are measured relative to brain landmarks such as the anterior and posterior commissures, and/or fiducial marks placed on defined locations on the subject using scanner-opaque materials.

To use manual search for a structure, the operator can view sections through the 3-D voxel data and search for known brain anatomical structures using radiological knowledge to locate the desired brain regions. The operator can then select combinations of individual voxels using a pointing device, or areas using a bounding line or shape. These selected voxels can be saved in computer memory, as well as saved to disk memory and recalled on later occasions.

Preferably, the software used in combination with the brain imaging device converts the anatomical data to a form that may be displayed or otherwise communicated to the subject or device operator in substantially real time, preferably while the subject is within the scanner. This allows the subject or device operator to use this information to select regions of interest for training, or to influence how the subject is performing his or her training exercises.

In one variation, software is employed that makes a 3-D transformation from standard space to the space of the subject's brain, and back, in substantially real time. For example, the software may take as input a set of 3-D Talairach coordinates or an anatomical volume directly from a computer-generated brain atlas and spatially transform the coordinates according to a 3-D spatial mapping to yield the corresponding locations within the anatomical volume measured for the subject.

Another example of defining a region of interest anatomically is to use a defined anatomical region from a reference brain such as in Talairach or MNI (Montreal Neurological Institute) coordinates. In this case, the anatomical region is defined in the standard coordinates, and then spatially transformed to localize the voxels corresponding to the anatomical structure in the subject's brain. This process is described in further detail at Section 23D in the Examples.

B. Physiological Localization of Brain Regions of Interest

The one or more discretely localized regions of the brain that will define the region of interest that may be used for training may be defined physiologically through finding the voxels that are modulated by one or more stimulus or behavior in comparison with a background condition. In order to do this, an important aspect of the present invention is its ability to monitor physiological activity in substantially real time after the stimulus or instruction for a behavior is provided so that the effect that the stimulus or behavior had on activity can be accurately determined. In addition, the brain region of interest may be determined within a short period of time after the collection of the physiological data. This short period of time may be less than 10, 5, 2, 1, 0.5, 0.25, 0.01 or less minutes.

Defining the region of interest may be performed by having the subject take part in a set of physiological ROI localization trials. During these trials, the subject engages in behaviors or experiences stimuli that are intended to activate one or more region(s) of interest. By monitoring resultant physiological activity, the location of these one or more region(s) are identified for that subject. The region of interest is normally defined after the completion of these trials based upon the voxels that are modulated. However, it is also possible to define the region of interest before all of the trials are complete, and then iteratively redefine the region of interest as additional substantially real time based measurements are taken.

Regions or volumes of interest may be defined that are modulated by the stimulus or behavior condition, and this determination can be made while the subject is inside the scanning apparatus. Regions of interest may either be defined on a voxel-by-voxel basis, or by defining a circumscribed area or volume such as a rectangle, circle, cube, or spheroid. The defining characteristic for whether each voxel will be within a region of interest may be based upon the value of an activation image/volume at the corresponding voxel. If the voxel is above a defined threshold in the activation image/volume, then the voxel is included in the region of interest. This process can take place either manually, or in a fully or partially automated fashion as described in the following two sections.

i. Example of Presentation of Physiological Localization Trials

The following example illustrates how a physiological localization trial may be performed. It should be noted that the particular physiological localization trial to be used will vary with the subject, the condition to be addressed, and hence the regions of the brain implicated.

In this example, in order to measure the modulation, a stimulus or behavior condition is presented to the subject following a rest or background period to constitute a physiological localization trial. These trials may be repeated one or more times. Measurements are made of the resultant physiological activation patterns in the brain scan volume at multiple time points throughout the localization trials. In order to localize the primary motor cortical representation of the hand, a subject may be asked to alternate between 30 second periods of rest with 30 second periods of moving, or imagining moving, the index finger of the right hand while scanning of the T2* weighted activation level is measured at every voxel within a brain scan volume every second.

ii. Manual Physiological Definition of Region of Interest

Once data has been collected, a region of interest may be determined from physiological localization trials, one or more regions within the brain that are selectively activated during one portion of the trials may be determined. For example, if the trials contain a rest period and a task period, a region may be determined which is activated selectively during the task period compared to the rest period. This process may take place using a principally manual method whereby the subject or device operator selects groups of voxels with strong modulation, any may view data corresponding to the time course of activation of these selected groups of voxels. Alternatively, this process may be partially or fully automated, with software selecting a set of voxels that meet certain criteria, such as a threshold level of modulation.

Figure 6:
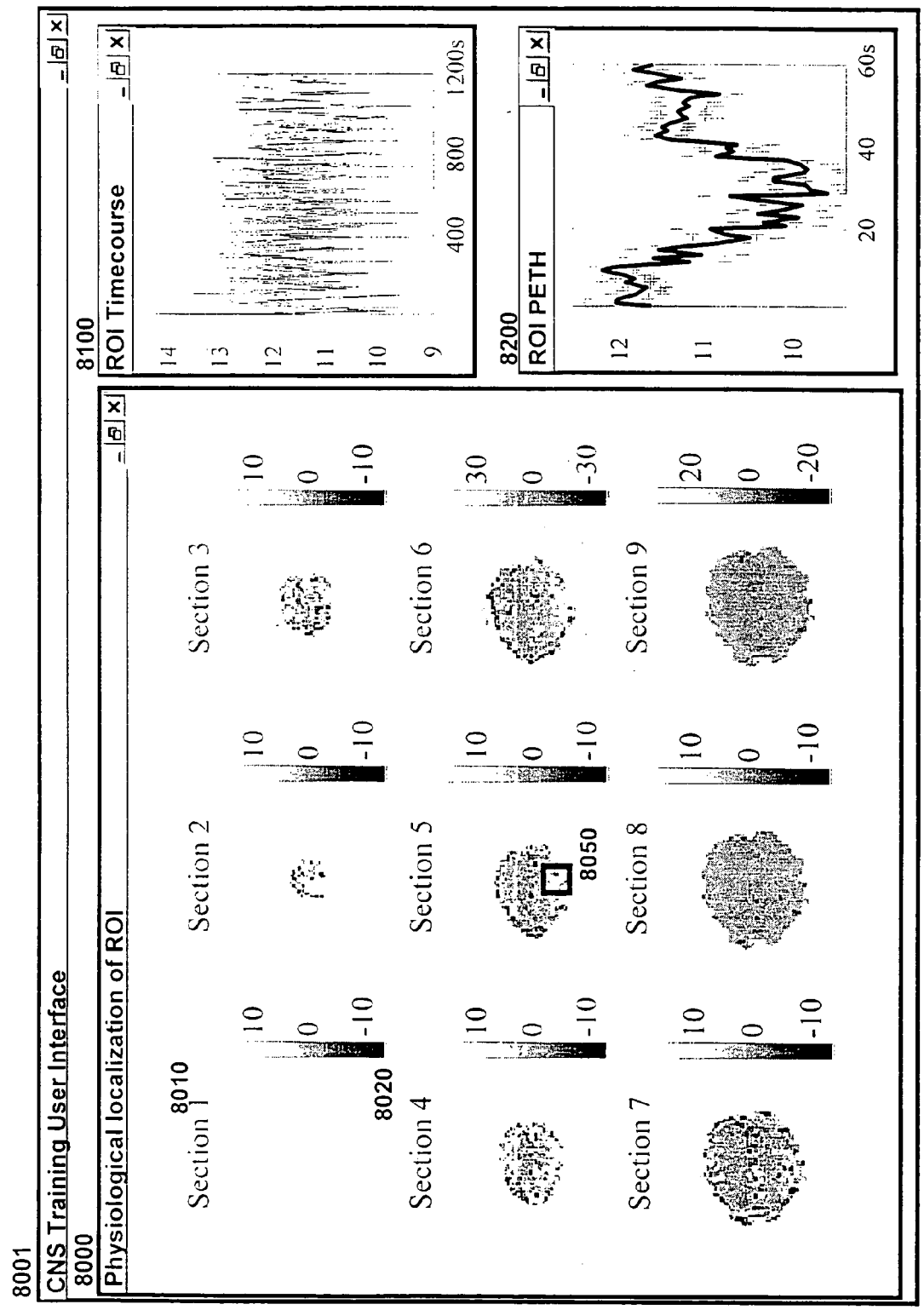
FIG. 6 is an example display screen that may be presented.
Figure 7:
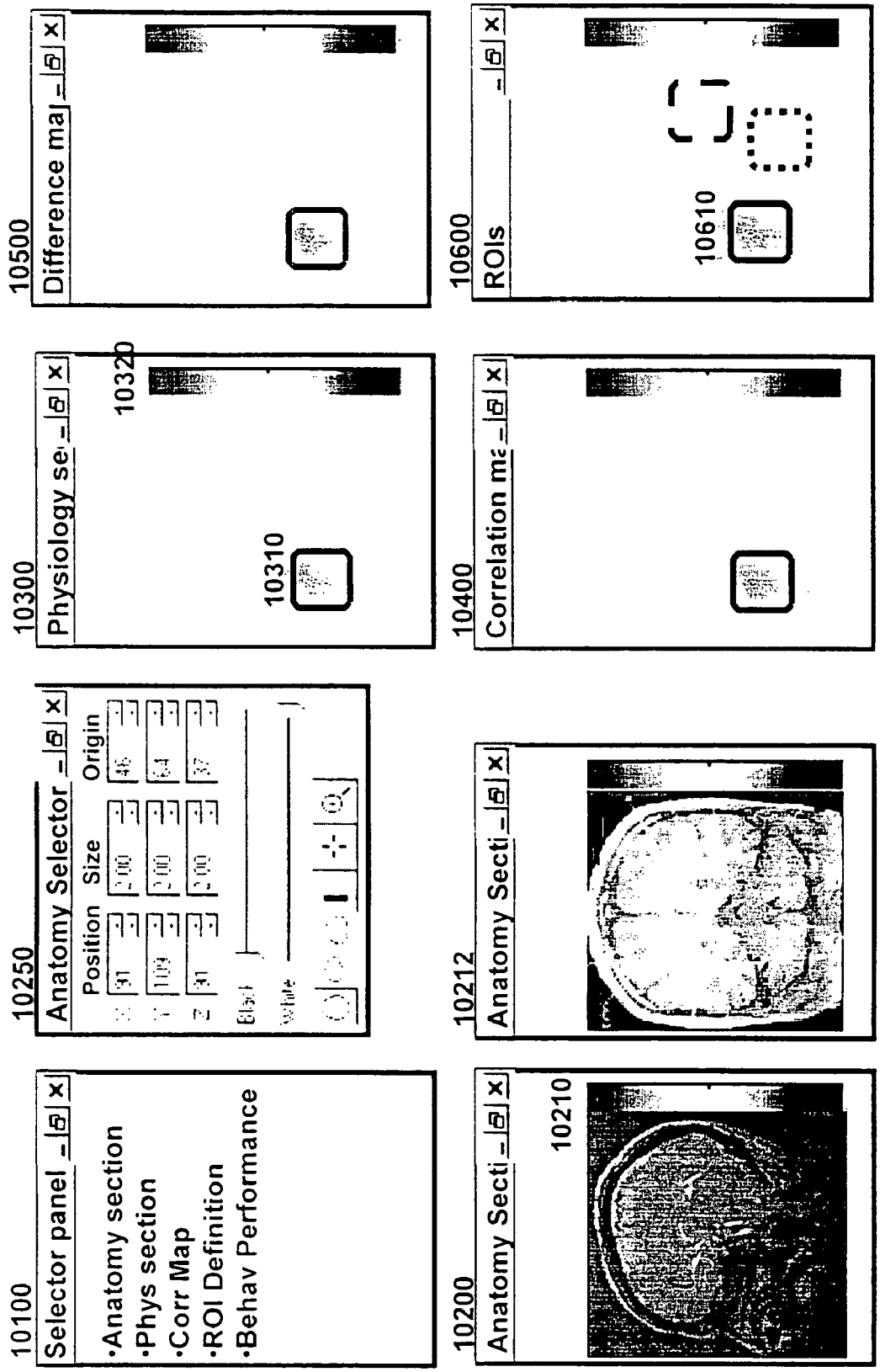
FIG. 7 is an example of a display screen that may be used for localizing a region of interest.
Figure 8:
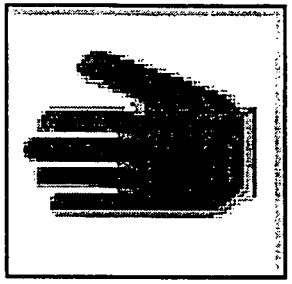
FIG. 8 shows examples of display panels that may be presented.

A wide variety of different physiological activation maps may be computed, as described in section 3.D. In one example, these physiological activation maps may then be used to compute regions of interest through a manual process of selecting the voxels that are activated by a portion of a trial using a provided display screen. For example, the average value during the stimulus or behavior condition minus the average value during the background or rest condition may be computed for each voxel in a scan volume. A montage for the physiological localization of an ROI 8000 using color coded activation maps may be presented to the subject as depicted in FIG. 6 on the user interface 8001. This figure represents actual data collected from a subject in substantially real time, collected using a task involving mental rehearsal of an imagined motion of the second digit of the right hand. This data could be used to select a region of interest while the subject is in the scanner. In addition, each panel of the display may contain a scale 8020, and a numerical index for the scale 8030 that may include measurement units. The subject or device operator may view each planar section within the scan volume in any plane of section, showing the level of the activation map. The corresponding anatomical section may be presented as well. The subject or device operator may use a pointing device such as a mouse to indicate the position of a region of interest 8050 based upon the area(s) that show activation on one or more of the sections shown. The subject or device operator may also zoom in or out on any section to more accurately localize are area of activation.

At this point, activity metrics are computed for this selected area or volume, and results may be displayed substantially immediately. This process may take place in a limited period of time. This period of time may be within 10, 5, 2, 1, 0.5, 0.25, 0.1, 0.01 or less seconds from the time of collection of the data. This process may take place while the subject is still in the measurement apparatus, such as the scanner. This process may take place prior to training of the subject. The timecourse of the average activity for this bounded area is computed and displayed 8100, as well as the PETH for this area triggered on the beginning of each 30 second rest period 8200. Each of these may be displayed with their corresponding timescale and magnitude scale, and may additionally include standard error or standard deviation measures, with an example shown for the PETH. The operator can then accept the selected area of the given section as the region of interest, or repeat the process until he or she is satisfied with the region of interest that has been selected.

iii. Automated Physiological Definition of Region of Interest

Regions of interest can be defined automatically using numerical criteria based upon the voxels of a scan volume, or a sub-region of a scan volume. These automatically defined regions of interest can then be presented to the subject or device operator for acceptance or alteration. This process may take place in substantially real time, and may take place while the subject is still in the measurement apparatus Numerical criteria based upon the computed activation images/volumes can be used to determine whether individual voxels are to be included within a region of interest. In one embodiment, the process involves performing a number of physiological localization trials, and processing the resulting scan volume data into activation maps.

The scan volumes may be pre-processed, and activation images/volumes may be defined. These activation images/volumes may be thresholded to select relevant voxels to be included in the region of interest. Additionally, spatial grouping may be employed, such as to reject voxels that are not adjacent to other selected voxels.

In one example, the 30 second rest, 30 second index finger movement task is used. Pre-processing uses a 1 pixel gaussian spatial filter using methods as described in Examples section 1. % BOLD difference activation volumes may be computed that correspond to: 100%×(the average computed for each voxel for all scan volumes from periods starting within 5 seconds after the start of behavior until the end of behavior, minus the average computed for each voxel for all scan volumes from periods starting within 5 seconds after the start of rest until the end of rest) divided by the average computed for each voxel for all scan volumes from periods starting within 5 seconds after the start of rest until the end of rest. This leads to a % difference map. The voxels with large values may be the voxels that are positively activated by this task, and may include the motor cortical regions that subserve this task. A region of interest may then be defined using a difference criterion such as all voxels with a difference value above a certain criterion, such as 0.5%. Voxels may be further selected by disregarding all voxels further than a criterion distance, for example one voxel, from a criterion number of other voxels above the threshold, such as one voxel.

One criterion used for automated physiological definition of a region of interest is a difference criterion, such as the average difference in % BOLD activation level between the stimulus or behavior condition and background, as just described. Another criterion used for automated physiological definition of a region of interest is a t-statistic criterion, such as a t-test statistical contrast comparing voxel values during a stimulus and a rest condition. Another criterion used for automated physiological definition of a region of interest is a statistical criterion, such as a an F-test statistical contrast comparing voxel values during a stimulus and a rest condition. Another criterion used for automated physiological definition of a region of interest is a correlation, such as the correlation of the activation of a voxel with the stimulus or behavior condition across repeated trials. Another criterion used for automated physiological definition of a region of interest is an additional statistical measure, such as the general liner model, non-parametric statistics, and corrections for repeated measures and spatial features as described in the documentation of existing MRI/fMRI/PET data processing packages. Another criterion used for automated physiological definition of a region of interest may be any of those described for the computation of activation maps or activity metrics in Examples section 1.

Once an ROI has been automatically determine, it can be analyzed just as with a described for a manually determined ROI in section ii above. The timecourse of the average activity for this bounded area may be computed and displayed, as well as the PETH for this area triggered on the beginning of each 30 second rest period. The operator may then accept the selected area, modify it by adding or removing voxels or areas, or repeat the process until he or she is satisfied with the region of interest that has been selected. This allows the user to select regions until the region that is most strongly activated by the stimulus has been determined.

5. Determining a Set of Effective Stimuli or Behaviors for a Particular Subject

Once the region of interest has been identified, stimuli or behaviors may be evaluated while monitoring the physiological activity response in the region of interest in order to determine stimuli or behaviors that are effective and relatively more effective in altering the physiological activity of the region of interest.

It is important to note that stimuli or behaviors that are effective for altering the physiological activity of a given region of interest for a first subject may not also be effective for a second, different subject. Hence, the present invention contemplates that the stimuli or behaviors used to alter the physiological activity of the region of interest should be individualized for a given subject. Described herein is an evaluation of the stimuli or instructions for behavior for an individual subject in order to select the most effective stimuli or instructions for behavior for that subject. It should be noted that the step described in section 5 of selecting the most effective stimuli or instructions for behavior for that subject is optional, and may also not be carried out, instead using the effective stimulus set described in section 1.E.

Determining effective and more effective stimuli or behaviors may be performed by presenting a series of different stimuli or instructions for behavior from a set of exemplars one or more times, determining an activity measure or index for each different stimulus or behavior from one or more brain regions of interest, comparing the effect each different stimulus or behavior had, and selecting the one or more stimuli or instructions for behavior that had the most desired affect on activity. By performing this selection process, the most effective stimuli or instructions for behavior may be identified for a given region of interest for a given subject.

Described below is an example of a process that may be used to determine a set of effective stimuli or instructions for behavior.

The subject may be in an fMRI scanner as described, and physiological measurements may be conducted repeatedly throughout to measure scan volumes. A series of trials may be conducted, each trial consisting of a 30 second rest or background period, followed by a 30 second period of activation by a behavior.

For each trial, first the subject is initially allowed to rest for 30 seconds. A stimulus or instruction for behavior is then selected. This selection may be a random selection. Additional selection methods are described in Examples section 3 below. The selected stimulus or instruction for behavior condition is then employed. Optionally, this includes presenting the stimulus or instruction to the subject using a subject user interface, such as a display that can be viewed by the subject. The activation for the selected stimulus or behavior may then measured as the % BOLD difference in average activity within a region of interest during the stimulus or behavior compared with during the rest period.

This process is repeated for different stimuli or instructions for behavior until all the stimuli or instructions for behavior to be evaluated have been presented, or until stimuli or instructions for behavior have been identified that provide a desired level of activation. The stopping point can optionally be defined by a selected number of repetitions of each condition, or a variance-based measure of certainty regarding the response to each stimulus or instruction for behavior, such as the certainty of a maximum likelihood measure of the most effective stimulus or instruction for behavior.

Based upon the activation patterns observed for each stimulus or instruction for behavior, certain stimuli or instructions for behavior are selected to be used in training. This selection is typically made by selecting a small number of stimuli or instructions for behavior from the complete set that elicit the largest activation in the region of interest. The more effective stimuli or instructions for behaviors are then used as the training exercises for the subject.

6. Training of a Subject

The invention disclosed may be used for training subjects, such as the training of subjects to modulate selected brain regions. Once a brain region of interest has been localized and effective stimuli or instructions for behavior have been selected based upon their ability to modulate the brain regions of interest, these stimuli or instructions for behavior may be used to train the subject.

Training may comprise performing trials comprised of alternating periods of rest, followed by exercise. These trials may be designed to engage the regions of interest of the brain using the selected set of effective stimuli or instructions for behavior. These alternating periods of rest and performing a task are typically formed together into training blocks that last at least 1, 5, 10, 20, 30 or more minutes, with physiological scanning beginning at the start of a training block, and taking place during each training block. Training blocks may be periodically repeated, with 1-10 training blocks taking place in one training session, and multiple training sessions taking place on the same day or on different days. The progress and physiology of the subject may be measured frequently and preferably in substantially real time during the training block.

As discussed, measurements of physiological activity, computations of results, and display of information are preferably performed in substantially real time. This display of information may be used by the subject to guide their performance and/or training strategy. For example, the subject may use the display to determine which performance strategies are most effective, and continue to use these strategies in favor of others. This display of information may be used by the device operator to make selections of how training should proceed, such as selecting stimuli for training.

In some 'control' trials the subject may not be provided with information about his or her brain activity, or may be provided with sham information based on random fluctuations or information from a different brain region or a previous time. These trials allow an estimate of the performance that the subject can achieve within the presence of the scanning information. These trials will be described separately in section 6.G. below.

Data from subject training is preferably recorded and stored. This allows the progress of the subject to be monitored and relayed to the operator and/or the subject. For example, a common type of information that may be relayed is an average level of the activity metric for the region of interest that the subject was able to achieve during each training trial, training block, and training session. This information may also be recorded to a more permanent recording medium, such as a computer disk storage device. Any and all raw data and computed measures may be stored for later recall.

A. Conducting Trials

During training, subjects may participate in a series of training trials, and physiological measurements may be made repeatedly at fixed intervals throughout. Training may also take place in the absence of physiological measurement as described in section 6.J. During a trial, the subject may first be allowed to rest for a period of time, a stimulus or behavior may be selected to activate the particular region of interest, and the subject may then be asked to attempt to activate a region of interest using the stimulus or behavior selected. The measurements taken during rest provide a baseline so that the effect the stimulus or behavior has can be better measured. It is noted that the rest measurement can precede or follow the measurement associated with the stimulus or behavior.

As an example, a behavioral trial within an fMRI scanner may consist of the subject first resting, and then attempting to activate a selected region of interest by observing stimuli and engaging in behaviors that will activate that region, such as imagining the motion of the right hand. The trial may begin with the presentation of an instruction for the subject to rest for a period of time. The stimulus or behavior that will be used in the trial may then be selected by the analysis and control software and then presented to the subject, such as an instruction to imagine moving the second digit of the right hand. This instruction may lead the subject to begin an exercise using any stimuli necessary to conduct the exercise. The subject may then perform the exercise, typically for a 30 second or 1 minute period of time. In this example, the subject may imagine making a hand movement in order to activate a motor cortical region. In training designed to activate a different brain region, the subject might be instructed to view or imagine a particular face to activate a face-selective brain region, or engage in a sensory discrimination test to activate a sensory region. After performing the exercise, the subject is again allowed to rest. After the rest, the subject may be asked to respond to a question in some cases, such as selecting whether a stimulus presented in the trial contained a particular feature. The training trial may then be repeated multiple times during the training block.

Some aspects of this process are explained in further detail in the following sections.

B. Measuring and Displaying of Physiological Activity

Substantially throughout the process of training, the physiology of the subject may be measured in the scanner. This information may be presented to the subject and the device operator, and may also be used for additional computations such as the computation of metrics from a region of interest. This process takes place at a regular repetition rate, such as one set of measurements per second in one example, or at an alternate sampling rate.

i. Physiological Measurement

While the subject engages in training, data are acquired and processed about the resultant brain activation. This process has been described above in sections 3.D. and 3.E. and FIG. 1. In summary, this process may comprise:

- collecting raw data as described in section 3.D.i
- reconstructing the result into images/volumes as described in section 3.D.ii.
- pre-processing the result as described in section 3.D.iii.
- computing activation images/volumes from the result as described in section 3.D.iv.
- computation of activity metrics from the result for defined region(s) of interest as described in section 3.D.v.

ii. Displaying Physiological Activation Maps

Many varieties of measurements may be made, and resultant computations performed and results displayed. Once activation images/volumes and activity metrics have been computed, they may be displayed to the subject and/or the device operator, or to remote parties. As shown in FIG. 1, the data analysis/behavioral control software 130 can provide information, such as measured information, stimuli, or instructions of various types on the display 180 viewed by the subject 190. This display can include physiological images of the subject's brain, matched anatomical images at the same level of section, 3-D reconstructions of either anatomy or physiological activation patterns, and both difference activity level images and statistical maps. The device operator and subject can therefore observe the pattern of activation as it evolves on pseudo-colored images. This section describes one example of information displayed. Further detailed examples of displays are described in examples sections 1 and 2.

In one example, the T2* weighted activation is measured in a 64×64×17 voxel scan volume corresponding to a 22×22×12 cm volume of a subject's brain. The subject engages in training involving a repeated task of 30 s rest and then 30 s imagined finger motion. Data are converted into scan volumes once per second in a process requiring less than one second. In this example, no pre-processing is used of the scan volumes generated. Scan volumes may be turned into % BOLD difference activation volumes by taking each successive volume, subtracting the 5th volume recorded, dividing the result by the 5th volume, and multiplying by 100% to yield an activation volume. The 5th volume is used as by 5 seconds into recording, subject magnetization has approached steady state.

A section from this % BOLD difference activation volume may be displayed to the subject and the device operator that includes the area selected as the region of interest as described in section 4 above. An example of how this might be presented is shown in 9950. Viewing this activation map may allow the device operator to continuously assess the activity in the brain region of interest during training, and potentially to stop training, relay information to the subject, or change the selected region of interest.

iii. Displaying Activity Metrics

From the % BOLD difference activation map, activity metrics may be computed corresponding to the physiological activity in a region of interest. A first activity metric may be the average activity in the selected region of interest, for example an area including the primary motor cortex. This activity metric may also be displayed to the subject and the device operator, for example as shown in FIG. 5, ROI activity 9600. This display may take the form of a scrolling line chart.

This provides nearly-instant information to the subject regarding the activity level metric achieved in the region of interest.

Viewing this chart may allow the subject to make ongoing assessments of the level of activation of the selected region of interest. These assessments of the level of activation may aid the subject in better performance of the task that they are undertaking to activate the brain region depicted, or in better performance of concurrent behavioral trials such as making a sensory discrimination. These assessments of the level of activation may aid the subject in determining which strategies for producing brain activation patterns are most effective, or in selecting which strategies to employ in the future. These assessments of the level of activation may aid the subject in learning how to best activate a localized brain region. These assessments of the level of activation may also aid the device operator in controlling the progress of training. These assessments of the level of activation may aid the device operator in determining whether to end training, in determining which stimuli or behaviors to employ, or in providing instructions to the subject.

Activity metrics may also be measured for comparing regions of interest, such as regions that are not undergoing training. It may be useful to measure activity metrics for comparison regions of interest to serve as a negative control for the primary region of interest, indicating that training has a selective effect on the primary region of interest rather than on broader areas of the brain. This information may also be presented to the subject or device operator as shown in example panel 9700. The activity seen in these metrics are frequently an indication of the overall arousal state of the subject. Using information from these metrics may help the subject to gain greater selectivity in controlling the region undergoing the training process rather than other regions. Information is also computed about the difference in activation between the primary region of interest and a secondary region of interest, which provides a selective measure of the increase in activity pattern within the region of interest less any overall changes affecting the brain more broadly.

iv. Displaying Movement Metrics

Another type of metric typically computed during training may be a set of movement metrics. The data collected may be used to derive information on the position of the subject within the scanner, and this in turn may be used to determine an ongoing measure of the subjects translational movement in 3-D, as well as roll, pitch, and yaw. This information may be provided to the subject to help them in maintaining a stationary position within the scanner, as for example shown in 11000. If movement parameters deviate outside define limits, the subject may be provided with warnings to maintain stillness within the scanner. Movement metrics may also be provided to the device operator to allow them to assess the movement of the subject, and abort training or provide information to the subject if movement is excessive. Movement information may also be fed into computations that allow for substantially real time movement correction of the scan volumes collected. Examples of the computation of movement metrics is described in Examples section 1.D.v.

C. Influencing Subject Behavior

As has been noted previously, a feature of the present invention is the performance of training exercises where information, stimuli or instructions for behavior are communicated to the subject through visual, auditory or other signaling. Preferably, what information, stimuli or instructions for behavior are used, and when and how the information, stimuli or instructions for behavior are used are at least partially based upon previously measured activities. In some instances, the previously measured activities may be from immediately preceding measured activities. This is made possible by measuring activities in substantially real time. In other instances, the previously measured activities may be activities associated with different earlier stimuli or instructions for behavior that were used.

i. Selecting the Next Stimulus/Behavior

A stimulus or instruction may be given to a subject representing something to perceive, or a suggestion for what the subject should do, such as an instruction to attempt to increase the level of activity in a target brain region, observe a presented stimulus, or engage in an action or cognitive activity. It is noted that the analysis and control software may take as an input previously measured activities and use that data to control what, when and how information, stimuli or instructions for behavior are communicated to the subject. The software may select what stimulus or behavior the subject will be engaged with for a trial. When the subject begins to perceive this stimulus, or engage in this behavior, this will cause a set of related changes in the brain of the subject. These changes may also be measured. In some cases, the subject may provide an overt response to the selected stimuli or instructions as well, as would be the case if the subject were completing a sensory discrimination task.

The stimulus or behavior used in a trial may be selected from the effective stimuli or instructions for behavior set. This selection may be a random selection from the effective stimuli or instructions for behavior set, may be based upon the measured activities of one or more preceding trials, may be selected based upon behavioral performance, or may be guided by the subject themselves or by the device operator. For the purpose of training a subject, the object of a trial may typically be to maximally activate one or more discretely localized brain regions. In such instances, selection of the stimulus/behavior to be used for the next trial may be based on measured information such that stimulus/behavior is able to effectively activate the one or more discretely localized brain regions being trained, or to help the subject to activation those discretely localized brain regions. If the activation created by different stimuli or instructions for behavior has been measured, then stimuli can be selected that lead to the greatest activation level. This can be useful for driving an increase in activation level when the object of training is to increase the activation of a target brain region, as might be the case for a condition involving a deficiency in this brain region.

As an example of stimulus selection, if there are 5 stimuli to choose between in the effective set, the software may compute an average of the % BOLD difference measured during presentation of each of these five stimuli. The software may then select for the next training stimulus the stimulus with the highest % BOLD difference, in order to drive a high level of activation. Alternatively, the software may select the stimulus with the lowest % BOLD difference in order to instruct the subject to increase his or her ability to drive a larger % BOLD difference for that stimulus.

As another example, the software may use adaptive tracking by selecting stimuli that drive lower activity when the subject has had some number of high activity trials, and stimuli that drive higher activity when the subject has had some number of low activity trials.

As another example, stimuli can be selected that drive the highest levels of a pattern of activity as determined by a pattern metric in the region of interest (see examples 1.D.). This can be used in cases where such a pattern is the target of training, as might be the case for a condition involving a two brain regions where a deficiency in activity in one area leads to a hyper-activity in a second area that the first area normally regulates or inhibits. In this case, stimuli might be selected that tend to lead the subject to activate the area with the deficiency, while inactivating the hyper-active area. A number of other example methods for triggering the timing and selection of stimuli or instructions for behavior is described below in section 1 and 3 of the Examples.

ii. Selecting when to Initiate a Trial or Part of a Trial

It is often desirable for a subject to begin a particular trial or part of a trial at a moment that is determined based upon the measured physiological activity up to that point, such receiving a stimulus or engaging in a particular action or training exercise when an activation metric reaches a threshold level. The data analysis/behavioral control software 130 can function to select time points for initiation of a trial when a particular activity metric is at a determined high or low value, or crosses a threshold value. Subjects can perform tasks more effectively, learn and remember more effectively, and undergo more effective and more rapid learning and training when trials are begun at times when the observed value of the activity metric for a relevant region of interest is above a threshold value.

One example of identifying when to begin a trial is beginning a trial when an activity metric measured from a region of interest has reached a criterion level, such as a criterion activation level. If, for the purpose of training it is desirable for a subject to achieve high levels of activation in a particular region of interest, then training trials can be begun at time points when the activation level for that region of interest is already above a defined threshold level. In this way, all trials are guaranteed to begin at times when the activity level is in a target zone, and the subject is trained to maintain the activity at this high level.

A simple example of selecting when to initiate trials uses a fixed trial duration. In this instance, it is sufficient for training to begin trials on a regular interval, for example each 60 second trial beginning at the end of the preceding trial, and begin the training portion of the trial at a fixed time, for example after a 30 second rest period. Further examples of selecting when to initiate a trial are presented in Examples section 3.

iii. Displaying an Instruction to a Subject

When the time has been selected as just described, an instruction may be presented to the subject using a display such as that shown in FIG. 5, or other display elements as described in section 3 or in the examples. The instruction may be to engage in a period of exercise by observing a presented stimulus or to engage in a behavior or action. An instruction may represent an instruction for what the subject should do, such as attempting to increase the level of activity in a target brain region, observing a presented stimulus, or engaging in an action or cognitive activity. For example, the subject may receive the text instruction "activate the region of interest above the performance target beginning now, observing the presented stimulus." In some cases, the task may require the subject to provide a response, as would be the case if the subject were completing a sensory discrimination task.

iv. Displaying Stimulus to Subject

A stimulus may be presented to the subject for the subject to experience. The timing of presentation and content of the stimulus given may be based upon a preceding activity metric measured from the subject in substantially real time, as has just been described. Visual stimuli may be presented on one of the display panels viewed by the subject or the device operator, for example as described in FIG. 5, or other display elements as described in section 3 or in the examples. For example, the subject may be presented with a visual image of a body part that the subject should imagine moving. When the subject begins to experience the stimulus this leads to changes in the brain of the subject resulting from sensory stimulation and cognitive processing. These changes may also be measured. Stimuli may also be presented to subjects using additional stimulation devices providing for stimulation other than visual stimulation, such as using auditory, tactile, proprioceptive, odorant, temperature, gustatory or other stimuli.

D. Analysis of Subject's Activation Performance

Once a trial has been performed and one or more activity metrics have been computed for a region of interest, the subject's performance at modulating the activity metric(s) can be assessed, and the subject and device operator can be provided with the resulting information. A number of measures can be computed of the subject's performance. These in turn can be used to set performance targets.

i. Activation Performance for a Trial

The subject's activation performance may be monitored throughout each trial, and the resultant information may be presented to the subject and to the device operator both during the trial and at the end of the trial. The activation performance that is monitored may include one or more activity metric being measured from a region of interest. This activation performance may also be a comparison of the activity metric with a performance target set for the subject. These may be presented on one of the display panels viewed by the subject or the device operator, for example as described in FIG. 5, or other display elements as described in section 3 or in the examples, such as an ROI activity panel 11600 with a corresponding performance target 11640 indicating the level that the subject is supposed to reach.

Typically activation performance may compare an activity level metric between a rest period and an exercise period of a trial such as the period when the subject is engaging in a task, perceiving a stimulus, or attempting to modulate the level of an activity metric. One type of activation performance measure may be the difference between the average of the activity metric during the stimulus/behavior period and during the background period. Another type of activation performance measure may be the average of the activity metric during the stimulus/behavior period alone. Another type of activation performance measure may be the average of the activity metric during the background period alone. Another type of activation performance measure may be a measure of whether the average of the activity metric during the stimulus/behavior period was above a performance target set for the subject. Another type of activation performance measure may be the percentage of the stimulus/behavior period during which the activity metric was above the performance target set for the subject. Another type of activation performance measure may be the amount by which the activity metric was above the performance target set for the subject. These types of information can all be presented to the subject or device operator to allow ongoing information about the subject's performance on the most recent trial or over a number of trials. This information may be presented, for example, using display panels 11300 and 11600. This is useful in aiding the subject's motivation, in helping to select strategies, and is helpful to training.

Once the activation performance has been measured, it is possible to designate whether a trial has been successful based upon the activation performance. Correct or successful trials may be defined as trials when a subject maintained an activation performance level on average above a performance target for the period of activation, stimulus, or behavior.

Based upon the subject's achieved activity level metric on the trial relative to the target level, the subject can be given rewards for their positive performance, or punishment for poor performance. It may be sufficient reward or negative reinforcement to indicate to the subject whether they have succeeded and give them a 'score' based upon their achieved level of activation and number of successful trials. Subjects can also be given additional rewards to achieve better motivation as described in the examples section.

The subject can also be given additional information, instructions, or suggestions to try to improve their performance on future trials. This can come straight from the device operator who may provide this information, or it may be generated by the analysis and control software. These may be presented on text instruction panels such as shown in 10900. Example information/suggestions that can be derived from the observed patterns of activity:

Activity metric for the preceding trial was high in the stimulus period relative to the background: 1) "Great job, keep up the good work and use similar strategies". Activity metric for the preceding trial was low in the stimulus period relative to the background: 2) "That trial was less successful, perhaps you can try a different strategy or increase effort". Movement metric for the preceding trial was high: 3) "Try to remain as motionless as possible within the scanner". Activity metric for the preceding trial rose slowing or late following an instruction to initiate activation: 4) "Try to time your activation pattern so that it starts promptly at the beginning of the trial". Activity metric for the preceding trial fell before the prescribed activation period had ended: 5) "Try to maintain your activation throughout the length of the trial".

ii. Activation Performance for Multiple Trials

Once activation performance and trial success computations have been computed for individual trials, they then may be combined to analyze the subject's performance across trials. For instance, the percent of successful trials may be computed, using the percent of trials when the subject maintained the activity metric above the performance target on average during the stimulus/behavior period. The percent of correct trials may be computed and displayed for different trial types or periods of time, for example as shown in 11500.

The level of difference in activation between the stimulus/behavior condition and the background condition may also be computed and displayed for different trial types or periods of time, for example as shown in 12050.

iii. Setting Performance Targets

Activation performance results and success results may be used to compute performance targets which may be displayed to the subject. A performance target may be set initially, and continually adjusted throughout training in order to ensure that training is constantly challenging, but achievable for the subject. This performance target may be presented to the subject before or during each trial as an indication of the level of an activity metric that the subject is intended to achieve. For example, when the subject views a graph of the on-going level of activation in a region of interest, a bar may be displayed on the chart indicating the level of the activity metric that the subject is intended to achieve during the stimulus or behavior periods of the trial. This is particularly effective when high-pass filtering is used in the activity metric to remove baseline drift. This target performance level constitutes an instruction to the subject to achieve a certain performance level during the trial.

One method of setting and continuously adjusting performance targets is to use adaptive tracking. In this methodology, an initial performance target may be set to a value that it is anticipated that the subject will be able to achieve, such as one standard deviation above the mean of an activity metric. Using adaptive tracking the performance target may be made more challenging when the subject achieves some number of successful trials in a row, such as three. The performance target may be made less challenging when the subject fails to achieve success on some number of trials in a row, such as one. Other methods of adaptive tracking are familiar to one skilled in the art. When the performance target is made more challenging, the subject can be alerted that they have moved up to a more challenging level, and when it is made easier they can be alerted that they have been moved down to a less challenging level. The subject's goal, of course, is to achieve the higher levels. The performance target may be increased or decreased by a fixed amount, such as one half of its current value, or by an amount based upon the activity metric, such as some fraction of a standard deviation of the activity metric.

Before or during each trial, the subject may be presented with a target level of the activity level metric that they are intended to reach or exceed on average throughout the trial. In one example, this performance target is presented on an ROI activity metric chart 11600 at the time that the subject is supposed to exceed this performance target level. Following the trial, the measured activity level metric is compared with the target to determine whether the subject succeeded in achieving the target activity level metric during the trial stimulus/behavior period. The change in the activity level metric from primary region of interest minus the change in an activity level metric from comparison regions of interest are also computed and presented to the subject and device operator. Performance target tracking information and the current difficulty level may be conveyed to the subject either as text, via digitized speech, or through a graphical representation such as a performance target line on the user interface indicating the target level of the activity metric.

E. Analysis of Subject's Behavioral Performance

If subjects are performing a behavioral task and therefore making overt behavioral responses during the trial period, then their performance at this task is analyzed to assess their behavioral performance. For instance, if a subjects is performing a visual stimulus discrimination task designed to activate visual sensory areas during training, then performance on this task may be computed for each trial. For each trial, the subject provides a response (e.g. a button-press indicating which of two alternative areas contained a visual stimulus). This response may be selected on a panel similar to 13500. The analysis and control software records these responses and makes computations of the subjects performance level. These computations correspond to typically measured psychophyisical parameters (see Green, D. M. and Swets, J. A. *Signal detection theory and psychophysics*. New York: Wiley, 1966). For instance, if sensory discrimination is being made on a number of stimuli along a continuum from easy to hard, the percent correct for each stimulus type is computed in order to generate a performance curve and determine a 50% correct threshold. Percent correct measures may be made in the same fashion for motor or cognitive tasks. These allow the computation of psychophysical parameters such as d' and beta according to standard methods familiar to one skilled in the art. The subject may be informed on each trial whether their response was correct or incorrect.

In one example, subjects may be trained to assess the level of an activity metric, such as the level of activation of a particular brain region, without being able to see information about that metric. In this instance, subjects may be cued to respond with an estimate of the activity metric at a given time, and may then present that response. For example, they may respond that the metric is either high or low, or they may make an estimate on a scale. In this case, their behavioral performance may be presented to them as an indication of how accurate their estimate was. This is useful in training subjects to be able to assess the level of physiological activity in a localized brain region of interest in the absence of externally provided information about this level.

F. Repeating Trials and Training Blocks

Behavioral trials as described thus far in section 6 may be repeated throughout a training block, typically lasting 10-30 minutes with substantially continuous physiological measurement throughout. Training blocks then may be repeated as well, with 1-10 training blocks taking place in one training session, and multiple training sessions taking place on the same day or different days.

G. Blind Trials

In some trials the subject may not be provided with information about their brain activity, or may be provided with sham information based on random fluctuations or information from a different brain region of interest or a previous time. These trials allow an estimate of the performance that the subject can achieve without the presence of the scanning information, or in the presence of false or random information.

H. Recording Progress of Exercise and Treatment

The subject's progress over each training session is monitored, and subjects and device operators are provided with information of the progress. A principle type of information may be the average level of the activity metric for the region of interest that the subject was able to achieve during each training trial, training block, and training session.

It should not be lost that training may be directed toward improving a particular condition that is to be treated. Accordingly, it is important that the progress of the subject also be measured in terms of signs and symptoms of the condition being treated, as well as behavioral performance. This information may also be presented to the subject and device operator.

I. Subject's Decreasing Need for Measurement Information

In general, the changes in brain activation that subjects are trained on through the use of this invention may be enduring outside of the context of brain physiology measurement. Increases in the strength of activation of neural areas can be thought of as being analogous to the increase in muscle strength achieve through weight lifting, which persists outside of the context of the weight-training facility. It is desirable for subjects to be able to modulate brain activation in the absence of a measurement device, and this process of transfer of brain activation patterns to contexts outside of the measurement of brain physiology can be facilitated. Subjects may be 'weaned' from the need for information about activity metrics to successfully modulate brain regions. This may take place by continuing to measure the subject's level of activity, but increasing the duration of time when the subject is not given access to information about the indicator during trials. Eventually, the subject may come to be able to control the physiological state without access to the indicator at all. It may also be possible to continue to give access to the indicator, but with increasingly diminishing levels of information being present in the indicator. For example, the indicator can increasingly be diminished in amplitude until it is difficult to assess its value. Ultimately, it may be possible through training with spatially-localized physiological indicators to teach subjects to control spatially-localized patterns of physiological activity even in the absence of the indicators that were initially used in training.

J. Performing Training Exercises in the Absence of Scanning

An aspect of this invention relates to a subject performing training that is effective in regulating physiological activity in one or more regions of interest of that subject's brain in the absence of information regarding the subject's brain states. Once optimal stimuli have been selected using physiological measurement, and/or a subject has been trained in controlling an activity metric in a region of interest with the presence of information about this activity metric, the subjects may be trained to continue to achieve this control and exercise of the corresponding brain regions in the absence of substantially real time information regarding the activity metric. This training can take place using training software largely analogous to that used inside the training apparatus, but run on a different computer. This computer does not have to be connected to physiological measurement apparatus. In place of real brain measurement information, the software can either use simulated information, such as random information, or it can use information from the same subject collected during scanning, or it can use no information at all and omit presentation of activity metrics.

In this method, stimuli or instructions for behaviors are selected based upon their observed ability to modulate a measured activity metric. This selection of stimuli is described in Examples section 3. Stimuli used may also have been derived as described in section 3, omitting the process described in section 5. For example, a subject may be trained at the modulation of a region including the motor cortex. The subject may use imagined movements as a behavior. The imagined movements that lead to the greatest pattern of activation may be determined by having the subject imagine those movements and other movements, and determine which ones lead to the highest level of activation in the region of interest. Then, in the absence of the measurement apparatus, the subject may use software that instructs the subject to engage in training using the same selected set of behaviors. This software can be the same software that the subject used while in the measurement apparatus, or different software. These stimuli that have been demonstrated to be effective can be used for the training of other subjects to activate similar brain regions.

K. Prescribing Ongoing or Follow-On Treatments as Needed

The exercise described in this invention can be combined with additional forms of therapy, such as pharmaceutical or rehabilitative medicine treatment. Accordingly, a medical professional monitoring the progress of the subject in regard to the subject's condition may prescribe additional training, change the training schedule, or discontinuing training as the need arises. The medical professional may also wish to prescribe or recommend training outside of the scanner using training simulation software. In other cases, the subject may be required to undergo follow-up in the scanner training or other activities and check ups periodically following initial training.

EXAMPLES

The brain is highly segmented, with localized regions of the brain performing entirely different functions. Hence, in order to have an impact upon a given brain disorder, it is necessary to be able to regulate a specific region of the brain. As described above, the present invention allows a subject to first identify what training exercises are effective for that subject in order to regulate a given region of interest, and then allows the subject train and exercise the region, and to evaluate how effectively the subject is applying the training exercise in substantially real time so that more effective application of the exercises can be achieved by the subject. Now that such selective activation of regions of interest of the brain can be achieved, a myriad of valuable applications are made possible. Described herein is a non-comprehensive list of different applications of the methods of the present invention. Also described are more detailed examples of the types of information that may be provided to subjects and of the types of computations used to generate these displays.

1. Performing Computations on Images Using Analysis and Control Software

The data analysis/behavioral control software 130 may be used to take in raw image data and perform a series of computations, including pre-processing 135, computation of activation image/volumes 137, computation of activity metrics 140, and selection, generation and triggering of information such as measured information, stimuli, or instructions 150. A single example of these steps were presented in sections 3-6 above. The following sections provide more detailed examples and explanations. The results of the computations described here are presented to the subject of the experiment or used to control its progress. It is noted that the examples provided herein relate to fMRI data processing. However, analogous methods may also be developed for other types of physiological data. The examples presented here can be performed using the functions developed in Matlab version 6.1 provided by the Mathworks, Inc., and its associated toolboxes such as the statistics, image processing, and digital signal processing toolboxes.

A. Data Pre-Processing

Physiological data received by the analysis and control software are in the form of raw T2* weighted 2-D or 3-D scan images/volumes 125. These data can be pre-processed using a variety of methods. One type of pre-processing that may be performed on the input image/volume data may be to pass the input image/volume data as output through to the next step of computing activation images/volumes without any further pre-processing. The resultant output is a set of 2-D or 3-D scan images/volumes that have undergone computations as described. Each of the methods described in this section can take the raw image/volume data 125 as its input, or can take the output of one of the other methods described in this section as its input. Further detail on each of these methods is provided in user manuals for Matlab ver 6.1, as well as in the user manuals and documentation for existing MRI/fMRI/PET data processing packages.

i. Spatial Smoothing

One type of pre-processing that may be performed on the input image/volume data may be spatial smoothing according to standard methods to produce smoothed image/volume output data. This is useful because it removes noise in the data, improves statistical properties by making the data variance more gaussian, and produces an image that is easier to interpret visually. This is accomplished by convolving the data with a 2-D or 3-D gaussian filter function with a defined half-width.

ii. Temporal Filtering

Another type of pre-processing that may be performed on the input image/volume data may be temporal filtering including lowpass, highpass, bandpass filtering and convolving with a function such as a hemodynamic response function. This is useful because it removes temporal noise in the data, matches the signal power in the data to that corresponding to the trials being conducted, and improves later data processing and statistical measures. This is accomplished by convolving the data with a temporal filter. This convolution will normally be with a causal filter as the data is being collected in substantially real time. The filter can be a highpass filter, such as a highpass filter with the cutoff of 10, 30, 60, 120, 240, 300 s, or the lowest relevant frequency component of the behavioral trials being conducted, or a drift rate that reflects the slowest relevant physiological change expected in the signal. The filter can be a lowpass filter, such as a lowpass filter or gaussian function with the cutoff of 0.25, 5, 1, 2, 4, 5, 10 s. The filter can be a lowpass filter designed to match the shape of a hemodynamic response function modeled as an alpha function. The filter can be a bandpass filter that accommodates a combination of highpass and lowpass characteristics. These filters can be designed using standard digital filter design techniques.

iii. Slice Time Correction

Another type of pre-processing that may be performed on the input image/volume data may be slice time correction to correct for the time of collection of each slice by interpolation. This is useful because it approximates the case where each slice in a scan volume was collected simultaneously. In order to perform this computation, the relative times of collection for each slice in a scan volume are known. The first image in each volume is taken as the reference image. The output values for each successive image in the volume are computed as the interpolated value between the measured value for each voxel in the image and the measured value for the same voxel in the previous image or succeeding. The interpolation yields the value corresponding to the estimated value for the voxel at the time point actually measured for the reference image. This standard method is described in the literature and in manuals for existing MRI/fMRI/PET data processing packages.

iv. Transformation into Standard Coordinates

Another type of pre-processing that may be performed on the input image/volume data may be a transformation into standard coordinates by applying a transformation vector that yields the corresponding value at each voxel in a standard coordinate space. This matrix is predetermined as described in Examples section 6. This has the advantage that all subsequent processing and display of data is in a standard coordinate space such as Talairach space or MNI space that can be directly compared with reference data.

v. Resampling of Data

Another type of pre-processing that may be performed on the input image/volume data may be resampling to increase or decrease the temporal and spatial resolution of the data, using band-limited filtering if needed. Resampling can produce a more detailed or less detailed view of the collected data. It can also be used to match the sampling of the data to that used in data set to which it will be compared, such as anatomical data collected for the subject, or data from a standard subject. Resampling can be performed using standard methods.

vi. Motion Correction of Data

Another type of pre-processing that may be performed on the input image/volume data may be motion correction to adjust for the motion that takes place between subsequent scans. This is useful because each section of each volume is in substantially the same position as in the first or reference scan of a scanning session. This can take place by applying using a transform created for each scan volume to that scan volume. The transform is designed to create the best fit in the least-squared error sense between the data of the current scan and the reference scan, including translation, rotation, and scaling if needed. An example of this software is described in: C C Lee, et al. Real-time adaptive motion correction in functional MRI. Magn Reson Med 1996; 36:536-444 and in manuals and literature associated with existing MRI/fMRI/PET data processing packages. Each of these steps, which can take place individually or in combination and in any order, will be familiar to one skilled in the art. These pre-processing steps may be applied to one or more reference scan, typically an early scan from the scanning session that will be used as a basis of comparison for computing activation images/volumes. These pre-processing steps may also be applied to each successive scan collected. The pre-processing for the reference scan(s) need not be the same as for subsequent scans. These pre-processing steps lead to pre-processed scan volumes for each sampled time point, which are then used for further computation and processing. The use of motion correction software may be used to allow motion of the subject relative to the measurement apparatus while measurements are collected and/or training is conducted, those measurements being corrected so that voxels correspond to the appropriate locations within the brain of the subject.

vii. Regression Filtering

Another type of pre-processing that may be performed on the input image/volume data may be regression filtering to remove noise components associated with exogenous events. For example, the activity level in each voxel may be correlated with an event not directly related to training, such as the phase of the cardiac or respiratory cycle. The data from each voxel may be corrected by regressing out this noise source. This method is described in the literature, for example in J. T. Voyvodic, NeuroImage 10, 91-106 (1999).

viii. Selection of Voxels Corresponding to Brain

Another type of pre-processing that may be performed on the input image/volume data may be the selection of voxels corresponding to the brain. This process may include the masking off of voxels determined to be outside of the region corresponding to the brain, such as voxels corresponding to the skull and regions outside of the head. This process may also include the masking on of voxels determined to be inside the region corresponding to the brain. This process may take place automatically under software control. Algorithms for this process are described in the literature and is known to one skilled in the art.

B. Computation of Activation Images/Volumes

Activation image/volumes may be computed taking as input a set of the pre-processed scan images/volumes, normally the entire set generated since a scanning session began. The activation image/volumes that are generated as output indicate the level of physiological activation at each voxel on the map. These maps may represent various measures of the second-by-second blood oxygenation level in the subject's brain regions that is an indicator of blood flow, and of brain metabolism and neural activation. These activation images/volumes, in turn, may be used as input to generate additional activation images/volumes, or to compute activity metrics from localized brain regions. These activation images/volumes may also be used as inputs to the displays that will be presented to the subject or the device operator.

i. Raw T2* Weighted MRI Signal

One type of activation image/volume that may be computed is the raw T2* weighted MRI is. This is the pre-processed output from the previous step. In this case, no further processing is performed at this step. This is useful primarily as a display of the raw signal, for example to appreciate any potential problems with data acquisition.

ii. Difference Images Including BOLD Difference Images/Volumes

Another type of activation image/volume that may be computed is the difference image, including BOLD difference images. One primary type of difference image is the measured difference in level between two time points. A single T2* weighted image by itself gives little information about the activity level at each voxel position, because the values measured primarily reflect the anatomical composition of the underlying tissue with a small contribution (e.g. 1%) from the physiological signal. By comparing images measured during different conditions, the anatomical portion of the signal will be essentially unchanged, but the portion of the signal corresponding to the physiological activation will be different. This is useful because it provides a measure of the change in physiological activation between two time points. Thus, the difference in T2* signal intensity between two time points is an indicator of the difference in physiological activation between those two time points. There are a variety of choices of what difference to compute, for example how many time points to average over before computing a difference.

Normally, a reference scan image or volume may be selected, which may then be subtracted from subsequent images or volumes. This reference volume can be the first scan of a session, or one of the early scans of a session because the first scan may be unrepresentative due to tissue magnetization not having reached steady-state.

One difference image/volume can be computed by subtracting the value at each voxel in the reference scan from the value in the currently measured scan. Another difference image/volume can be computed by subtracting the average value over a defined time period before the current scan from the value in the currently measured scan, useful if the steady-state level measured is drifting over time. Another difference image/volume can be computed by subtracting the time-filtered and/or spatially smoothed value from a time period before the current scan from the value of the currently measured scan, also useful to reduce noise and correct for baseline drift. Another difference image/volume can be computed by subtracting the average value from a series of reference scans collected during one or more background or rest conditions, useful when an average background level is the most appropriate for taking a difference. Another difference image/volume can be computed by subtracting the average value from a series of reference scans collected during one or more behavior or stimulus conditions, useful when an average activated level is the most appropriate for taking a difference.

iii. % Difference Images/Volumes

Another type of activation image/volume that may be computed is the percent difference image/volume, computed by normalizing the measured difference image/volume in order to produce an image/volume in units of fractional difference, or percent difference. For example, a % BOLD difference image/volume is computed by taking a single difference image/volume and dividing it by a reference image/volume. At each voxel, the resultant % BOLD signal equals, for example 100%×(signal at time point−signal at reference time point)/(signal at reference time point). % difference signal images/volumes can be computed by taking any of the above difference signal images/volumes, and dividing them by their corresponding reference or average reference images/volumes.

iv. Variance Images/Volumes

Another type of activation image/volume that may be computed is a variance image/volume. The variance of any pixel or group of pixels over a period of time can be computed, and these values can be formed into a variance image/volume. These images can be useful in located blood vessels, which might be excluded from further analysis in certain instances where brain matter physiology is the target, or focused upon if vascular perfusion is the target.

v. Statistical Contrast Images/Volumes

Another type of activation image/volume that may be computed is a statistical contrast image/volume. Images and volumes can also be computed based upon statistical measures of activation for each voxel. This may be useful because these maps indicate measures of the reliability with which a given voxel's activity correlates with some condition(s), such as a stimulus, or behavior. One type of statistical contrast map that can be computed may be a t-test map, that may compute the p-value from a t-test comparing the set of measurements for a voxel during one condition, such as a background or rest condition, with the measurements during a different condition, such as a stimulus or behavior condition. Another type of statistical contrast map may be an F-test map, that may make a comparison of these same sets of measurements using an F-test and a predictor model such as a boxcar or sin-wave function representing different behavioral periods, or a boxcar function convolved with a haemodynamic response function such as an alpha function. Another type of statistical contrast map is a map that may be corrected for the large number of degrees of freedom inherent in fMRI data reflecting serial measurements, or corrected for spatial correlation among proximate voxels. The computations involved have been described extensively in the literature, and in the manuals and supporting literature for existing MRI/fMRI/PET data processing packages.

vi. Contour Maps of Activation Images/Volumes

Another type of activation image/volume that may be computed is a contour map, which may be computed to designate the contour lines on an activation image or volume for a set of one or more contrast levels. This may be useful for displaying and viewing activation images/volumes, or for localizing regions of activation.

vii. Thresholded Maps of Activation Images/Volumes

Another type of activation image/volume that may be computed is a thresholded map. Thresholds may be computed and used to cut out certain most relevant portions of the data from activation images/maps. Thresholds can be defined as a mean value of a region, or some fraction of the mean value. The fraction can be defined by a measure of the variance. An example threshold would be two standard deviations below the mean value of an entire activity pattern image. In some cases it may be helpful to set all values below or above a set threshold to a background level.

C. Displaying Activation Images/Volumes

Anatomical and physiological data representations may be presented to the subject in substantially real time using a display 180. In addition, these data may be presented to a device operator on one or more additional displays. In one embodiment, activation image/volume data from an fMRI is transformed into a variety of intensity-coded or color-coded 2-D image maps. These maps may be presented a 2-D sections, such as coronal, sagittal, axial, or oblique sections. They may also be presented as 3-D images such as transport or cutaway volume images, rendered 3-D volume images, or wire-mesh images. Physiological measurements can also be overlayed onto anatomical measurements either using 2-D anatomical images as seen in 9950 or 3-D rendered brain images. These methods are familiar to one skilled in the art and are described in available documentation for existing MRI/fMRI/PET data processing packages (see definitions). The resultant images are presented using the displays described in Examples section 2.

D. Computation of Activity Metrics

Data from activation images/volumes can be used to compute activity metrics. These activity metrics are computed measures from regions of interest within activation images/volumes. The input to these computations are the time series data from a single measurement point or voxel, or from a group of voxels that constitute a region of interest or an entire image or volume. A simple example of an activity metric is an average value at a single time point for all of the voxels within a region of interest. Some example activity metrics are described here. All of these metrics can be computed in substantially real time.

i. Average Value Metrics at a Single Time Point

One type of activity metric that may be computed is the average value from a region of interest at a single time point. This value gives an indication of the average level of activation for the region of interest, which can be used in training subjects to increase or decrease this level of activation.

ii. Spatial Pattern Comparison Metrics

Another type of activity metric that may be computed is a spatial pattern comparison metric. Spatial pattern comparison metrics can be used to compare the pattern of activity in a region of interest with a target or reference pattern. This is useful, for instance, if a subject is being trained to approximate a target pattern of activation. In this case, the subject receives information regarding the difference between the currently measured pattern and the target pattern, and is trained to decrease this difference. One type of spatial pattern comparison metric can be computed as the sum of the voxel-by-voxel differences between the current pattern and the target pattern in an ROI, indicating overall closeness to the target. Another type of spatial pattern comparison metric can be computed as the sum of the voxel-by-voxel sums of the current pattern and the target pattern in an ROI. The two preceding spatial pattern comparison metrics can be divided by the target pattern sum to give a percentage value. Another type of spatial pattern comparison metric can be computed as the dot product between the vector comprising the current pattern and the vector comprising the target pattern in an ROI, indicating overall closeness to the target.

iii. Correlation Metrics

Another type of activity metric that may be computed is a correlation metric. Correlation metrics can be computed that correspond to the correlation between the activity of two voxels, or two regions of interest over time. This may be useful in training subjects to generate great correlation between to brain regions, for instance in order to create stronger functional coupling between the activity in two brain regions. One type of correlation metric can be computed as a correlation coefficient between two activity metrics, r. Another type of correlation metric can be computed as an activity-triggered average between two activity metrics, such as the average level of activity at one point for one or more ranges of activity level at another point. Another type of correlation metric can be computed using 'network analysis' to determine functional connectivity between different points within the brain as described in "Functional neuroimaging: network analysis", L Nyberg and A. R. McIntosh, in Hand-Book of Functional Neuroimaging of Cognition eds Roberto Cabeza and Alan Kingstone.

iv. Threshold Crossing Metrics

Another type of activity metric that may be computed is a threshold crossing metric. Threshold crossing information can be used to measure when an already-computed activity metric crosses a given threshold level. This can be useful to indicate to a subject when they have achieved a target level of a given activity metric, such as playing a sound that indicates success at those times. Another type of threshold crossing metric can be computed as the time when the signal crosses a defined threshold value. Another type of threshold crossing metric can be computed as an indicator of whether the signal is above or below that threshold value. Another type of threshold crossing metric can be computed as an indicator of whether there has been a change in whether the signal is above or below that threshold since the last time point, and the direction of the threshold crossing. Another type of threshold crossing metric can be computed as a positive value at time points when the threshold is crossed, and a zero value at other time points.

v. Movement Metrics

Another type of activity metric that may be computed is a movement metric. Movement information can be used to measure determine whether a subject's movement in the scanner is confounding other measurements. Movement measurements give an indication of the position or change in position of the subject's head, brain or some other anatomically defined structure within the scanner. One type of movement metric take the form of x, y, z cartesian coordinate information, as well as pitch, roll and yaw rotational information. Another type of movement metric take the form of the chance in x, y, z cartesian coordinate information, as well as pitch, roll and yaw rotational information between two time points. A position metric can be computed by thresholding the brain scan volume data to zero for values below ⅛th of the mean value, and 1 for values above this threshold, and then computing the x, y, and z values for the centroid of the resultant volume. This centroid vector can be compared with a centroid vector at a reference time such as the first scan to give measures of change in position. Subjects can be instructed to remain more still if movement exceeds certain limits. More detailed methods for computing movement metrics will be familiar to one of ordinary skill and are described in available documentation for existing MRI/fMRI/PET data processing packages.

vi. Movement Correlation Metrics

Another type of activity metric that may be computed is a movement correlation metric. Once movement metrics and activity metrics have each been computed, then metrics of the correlation between the two can be derived. These metrics are helpful in determining whether a subject's movement is contributing significantly to the activity metrics that have been observed. An F-test can be used to compute the relationship between an activity metric and a movement metric. Once a relationship has been determined, the contribution of the movement can be regressed out of the activity pattern data. This can yield measures of activity pattern data in the absence of the contribution of movement.

vii. Signal Processing Metrics

Another type of activity metric that may be computed is a signal processing metric. A number of other mathematical measures can be made on activity metrics that provide additional useful information to characterize these signals, and in turn to control them. Certain of these metrics may correspond with particular behavioral or cognitive states, and thereby be used as a measure of the presence of those states, or to train subjects in reproducing those states. For example, active states may have more power at high frequencies of an activation metric, whereas passive or relaxed states may have less power at those high frequencies. Example signal processing measures include: the power spectrum of the activity metric, the power of an activity metric within a limited band-pass filter band, and the spectrogram of the activity metric.

viii. Activity Position

Another type of activity metric that may be computed is an activity position metric, that may compute the position of highest activity within a region of interest. In this example, the voxel or group of voxels showing the highest level of an activity metric are determined. This activity position can in turn be used as a method for decoding what is being represented by mapped neural activity. It has long been known that activity in many brain areas is 'mapped'. Activation in different regions corresponds with particular stimulus or movement features. For this reason, a center of activation at any one point on a map can be used to determine the corresponding feature on a known map as the feature that is being encoded. This may be useful in forming an estimate of what is being represented in the brain of the subject at any point or period in time. This, in turn, can be used to guide training, such as by selecting a next stimulus of a character that is related to that which is being coded at a particular moment.

ix. Vector Average Metrics

Another type of activity metric that may be computed is a vector average metric. Vector average metrics may involve computing an estimate of the decoded object or feature being represented by a given activity pattern. One example of this decoding is the measurement of a vector average of activity. In this example, the measure of an activity metric at each voxel within a region of interest is computed, and is multiplied by a feature vector assigned to that voxel that corresponds to the voxel's underlying feature selectivity or representational function. The vectors are then averaged to produce a vector average activity metric. This vector average can be used to compute an estimated feature being represented by the underlying physiology in the region of interest. The feature vectors that area used for each voxel may correspond to what the voxel has been determined to be involved in the processing of, or to the voxel's relative position on a defined representational map such as a cortical map of visual or motor space.

For example, for visual brain areas, the feature vector for each voxel may correspond to a position in visual space, or to a combination of other visual features, that are represented by activity in the brain of the corresponding voxel. The feature vector may also be determined by a voxel's position on a visuotopic map. For auditory brain areas, the feature vector for each voxel may by the preferred sound frequency for that voxel, or to its relative position on a tonotopic map. For somatosensory areas, the vectors may be positions on the body that the voxels are involved in receiving input from, or the voxels relative position on a somatotopic map. For motor areas, the feature vectors for each voxel may be points in space reached by a motion preferentially activating the voxel involved, or may be muscle groups that are preferentially activated in conjunction with the activation of the measured voxel. They may also be the information or function designation on a motor map of the area. Taking the motor example, it has been shown that by taking the vector average of the level of activity times the preferred movement target for each of a number of points in the motor cortex, an estimate can be made of the movement target for a particular activation pattern (see Motor area activity during mental rotation studied by time-resolved single-trial fMRI. W. Richter R. Somorjai R. Summers M. Jarmasz R. S. Menon J. S. Gati A. P. Georgopoulos C. Tegeler K. Ugurbil S. G. Kim; J Cogn Neurosci. March, 2000; 12(2):310-20, Primate motor cortex and free arm movements to visual targets in three-dimensional space. II. Coding of the direction of movement by a neuronal population. A. P. Georgopoulos R. E. Kettner A. B. Schwartz J Neurosci. August, 1988; 8(8):2928-37). In this way, the vector average method may provide one indication of what is being represented by a given pattern of activation within a region of interest.

x. Feature Decoding Metrics

Another type of activity metric that may be computed is a feature decoding metric. Additional methods are available for decoding what is being represented by brain areas through computations involving the vector of activity at a large number of points in the brain. These additional decoding metrics may also be useful in forming an estimate of what is being represented in the brain of the subject at any point or period in time. This decoding indicates that a relation is formed between different states or patterns of activity in a region of interest and objects or movements that may be encoded. Many types of methods have been developed for creating this relation (see for instance Real-time control of a robot arm using simultaneously recorded neurons in the motor cortex, J. K. Chapin K. A. Moxon R. S. Markowitz M. A. Nicolelis, Nat Neurosci. July, 1999; 2(7):664-70), and these methods may be used by this invention. Once an estimate is available of what is being represented in the region of interest, this, in turn, may be used to guide training, such as by selecting a next stimulus of a character that is related to that which is being represented at a particular moment, or a behavior based upon what is being represented.

xi. Time Average Metrics

Another type of activity metric that may be computed is a time average metric. Once the activity metrics described have been computed, they can each be averaged over periods of time. Average values can be usefully employed to compare different conditions. In one example of a time average metric, the average of an activation metric can be computed for all time points within a recent period of time to determine a subject's recent level of activation in an ROI. In another example of a time average metric, the rolling average of an activation metric can also be computed. In another example of a time average metric, averages can be computed for different types of conditions, such as the average of a metric for all time points falling within a particular behavioral or stimulation condition. In another example of a time average metric, averages can be computed for all time points falling within a background or rest condition.

xii. PETH Metrics

Another type of activity metric that may be computed is a peri-event time histogram metrics (PETH) metric. PETH metrics are particularly useful for determining the average time course of a metric following a behavioral event, stimulus, or other event. PETH metrics are computed as the average over several trials of an activity metric, computed separately for a number of time points before or after a reference time point, such as the beginning of a trial.

xiii. Likelihood of Behavioral Success Metrics

Another type of activity metric that may be computed is a likelihood of behavioral success metric. There are some time periods when a subject is more likely to succeed at a given task than others. It is generally desirable to identify when a subject is most likely to succeed or have a positive outcome in performing a behavioral task such as a perceptual or behavioral task or training. For example, when the occipital or temporal cortical brain regions subserving the visual perception of a particular stimulus are activated, and frontal regions involved in extraneous tasks such as unrelated thoughts are not activation, the subject is more likely to succeed at a visual discrimination task. Related findings have also shown that people remember better when areas of the brain involved in memory are more active. Previous studies have documented this retrospectively. Prospective measures of a subject's activity in a region of interest involved in subserving a given task can be used to predict when the subject will have a positive successful behavior, or perform a task quickly, or learn or remember more effectively. Therefore, these measures are helpful in training and exercising the subject.

A measure of the likelihood of success in any task can be made based upon an activity metric measured before or during a task if there is some correlation between the activity metric and success in the task. A relationship may be measured between the distribution of activity metrics over many trials, and the distribution of success at performing a task over many trials. This relationship may include an average likelihood of behavioral success for each of a number of ranges of the distribution of the activity metrics. Using this relationship, it may be possible to form an estimate of the likelihood of behavioral success for a trial conducted when the activity metric is at any particular value.

Take for example, an activity metric that varies primarily over the range of 0-1%, and 100 observed trials of a behavioral task that the subject gets right on 50% of occasions on average. The average percent correct trials can be computed for all of the measured trials that followed a 5 second period when the measured activity metric was between 0.2 and 0.3%. Similarly, the average percent correct can be computed for all other 9 increments from 0-1% for the activity metric. If there is a correlation between the activity metric value and behavioral performance, this may lead to a curve showing that at the low values of the activity metric, the subject got less trials correct on average, whereas at the high values, the subject got more trials correct on average.

Likelihood of success metrics can be computed separately for different stimuli or behaviors. For example, one observed pattern of activity may correlate with a high likelihood of success for one stimulus or task, while a different pattern correlates with a high likelihood of success for a different stimulus or task. Computing the likelihood of success for both stimuli/tasks allows the selection of whichever stimulus or task is more likely to be successful at a given moment.

Using the relation between the activity metrics and percent of positive behavioral outcomes determined by the curve, which can often be fit with a line, exponential, or logistical function, it may be possible to predict the likelihood of success on a given trial using a given stimulus from the value of an activity metric.

xiv. Combinations and Comparisons of Activity Metrics from the Same or Different ROIs Another type of activity metric that may be computed are combinations and comparisons of activity metrics from the same or different ROIs. It is often useful to make comparisons between different activity metrics, or to compare the same activity metric for different time points, or time periods. All of the activity metrics described above can serve as inputs to combination and comparison functions such as sums, averages, differences, and correlations. A useful comparison metric may be the difference between an activation metric for a recent period of time and the same activation metric computed for a reference period of time, such as an earlier period of time. This value indicates the changing level of activation in an ROI. The difference can also be computed between the average value of an activity metric computed from one time period, such as the difference between the average of a metric for all time points falling within a particular behavioral or stimulation condition, or for all time points falling within a background or rest condition. Combinations can also be made between separate activity metrics, including such as sums, averages, differences, and correlations. An example is the difference in activation level between one ROI and another ROI at the same time point. This can be useful in indicating when one area is more active than another, and can be used for training subjects in creating a higher activity level for one area than another. Differences can also be computed for different time points, which can be useful in determining whether one area is leading or lagging another area.

E. Displaying Activity Metrics

Activity metric data may be presented to the subject in substantially real time using a display 180. In addition, these data may be presented to a device operator on one or more additional displays. The resultant images may be presented in a variety of ways, as described in the examples presented in the following section.

2. Examples of Information Displays

As has been noted, an important aspect of the present invention relates to the provision of information to the subject as the subject's brain activity is measured in order to influence how the subject performs training exercises. In one variation, information is communicated to the subject through computer generated displays which the subject is able to observe during training.

The information can relate to instructions, brain measurements, sensory stimuli, and training performance. Each of these different types of information may be displayed by itself or in combination with other types of information.

The layout of the content of the information displayed can be widely varied. For example, the information can be in graphical and/or in text form. The displayed information can include static images as well as moving images, and optionally can also be accompanied by sound, or by other forms of sensory stimulation. The subject or device operator can select multiple types of information that will be displayed together from among those described and depicted here.

Described herein are examples of what types of information may be displayed to assist the subject. Example display panels are shown in FIGS. 8-12.

A. Instructions

An important type of information that may be displayed to a subject is instructions. These instructions alert a subject regarding different things that the subject is asked to do including perform a training exercise, rest and other forms of response that may be asked of the subject. The instructions may be displayed concurrently with other forms of information.

Moving visual images or a sequence of sounds or verbal instructions or other means of communication can instruct the subject to perform ongoing sequenced behaviors, with each successive element in the sequence controllable based upon measured physiological activity. Provided herein are examples of different instructions and ways of communicating brain measurements that may be displayed.

B. Measured Information

Another important type of information that may be displayed to a subject is information relating to brain measurements. Provided herein are examples of different brain measurements and ways of communicating brain measurements that may be displayed. This display may include raw anatomical brain image, raw functional brain image, moment-by-moment representations of activity metrics, scrolling charts of the average level of activity in a particular voxel or region of interest. This display may also include performance measurements, including both measurements of performance of an overt behavioral task, and measurements of performance of the subject's modulation of a region of interest.

C. Stimuli

Another important type of information that may be displayed to a subject is stimuli. Provided herein are examples of different ways of communicating stimuli. Types of stimuli that may be presented include static or moving visual displays, tactile, proprioceptive or heat stimuli, odors, sounds, and other forms of sensory information.

D. Examples of Information Displayed

Many types of information may be presented, as will now be described in detail. One type of display panel is an Anatomy Section 10200. This panel may present a T1, T2, or T2* weighted anatomical section of the subject. This section may be a coronal, sagittal, axial, horizontal view, or some other plane of section through the brain. This panel may also include a scale 10210 that indicates the correspondence between levels of brightness and measured values. This panel may be used for localizing anatomical structures, such as when the device operator uses anatomical knowledge to look at one or more sections and determine the location of relevant anatomical structures. This panel may also be used for defining the location for a region of interest. For example, once the device operator has located an anatomical structure, he or she may select pixels or select a bounded area on this display that will correspond to a region of interest. This display can also be used to compare with another subject or a standard reference brain. For example, the device operator may select sections of the subject's brain that correspond with known locations defined in a reference brain such as described in the Talairach atlas brain or MNI reference brain. This operator may do this by comparing images of the subject's brain with images of a standard brain to find like structures. This may take place while the subject is in the scanner. This may be part of the process of determining a region of interest. This region of interest may be used in the training of the subject.

Another use of this panel is to present outlines of defined regions. These outlined defined regions can be used in defining a region of interest for training. For example, if the device operator would like to select Brodmann's area 4 as a region of interest, the software can outline Brodmann's area 4 on the display, and the device operator can use this information to select the appropriate voxels or area as the region of interest. Anatomically defined regions can include any of the regions defined in a standard reference atlas such as the Talairach atlas or the MNI atlas. Defined regions can also include the saved regions of interest defined for the subject or for previous subjects or groups of subjects. The display can show lines outlining a defined structure. These defined regions when displayed can also be labeled on the display according to their names. In addition, these defined regions can be transformed into the appropriate space to match the anatomical section of the subject, and presented overlayed onto the subject's anatomical section. This can be useful in localizing anatomical regions in the subject, because it indicates which voxels in the current subject correspond to defined structures in a reference brain. The process of this transformation, which can serve as the input to this display, is described in Examples section 6.

Another type of display panel is an Anatomy Selector 10250. This panel may present controls usable by the subject or device operator to select or manipulate the displayed anatomical section. These controls can include controls for selecting the plane of section to display, such as coronal, sagittal, and the position of the plane of section, and selecting the number of the scan plane within a scan volume, such as a rostral, central, or caudal section. This panel may also include additional controls to adjust the brightness and contrast of the image, the ability to select the scaling and zoom and cropping of the image, to turn on and off subject information, and to make text or graphical annotations on the section and mark regions of interest.

Another type of display panel is a Physiology section 10300. This panel may present an activation image as computed as output as described in Examples section 1.B. This panel, and all anatomical and physiological activity panels, may also show regions of interest 10310 being used for training, or for measurement of an activity metric. Physiological activity panels may also present scales 10320 that indicate the level of activity being presented, as well as a numerical units scale, and may be color coded or intensity coded. One type of activation image that may be displayed is a correlation map 10400. Another type of activation image that may be displayed is a difference map 10500. All of the types of computed activation images/volumes may be selected for presentation by the device operator or user using the selector panel, or pre-defined in the software.

One primary use of a physiology section panel is to allow the subject or the device operator to select the area of a region of interest. This process is described in section 4. The subject or device operator may use a pointing device to select a combination of voxels, or one or more bounded area corresponding to the region of interest. By inspecting the physiology section, this selection can be made to correspond to activated or inactivated brain regions. This region of interest can then be used in subject training.

Another use of this panel is to present physiological results from a comparison brain or from an average of a group of brains, such as a standard brain, which may be used by the subject or device operator to make comparisons to the physiology section. The physiological results from the standard brain may be transformed into the coordinate frame of the current subject using the same transform and methods described for transforming an anatomical structure, as described in Examples section 6. The device operator or subject may select a standard brain, and a physiological activation condition from the standard brain, for display by the software. The subject or device operator may then be able to select voxels or bounded areas from the standard brain that had been activated by the current task, which they may use as a region of interest. Also, using this standard brain, the device operator or subject may be able to find regions with higher or lower activation in the subject than were observed in a standard subject performing a similar task. Images or volumes may additionally be presented of a subtraction or other comparison of data collected for a standard brain or group of brains during a similar task from the current subject's brain, to highlight differences in activation patterns.

These comparisons may facilitate the localization of structures for use as a region of interest. These structures may be used as regions of interest for training. Another use of this panel is to present outlines of anatomically defined regions overlayed onto physiological activation patterns. This is very similar to the use of outlined regions of interest just described for anatomical panels. These outlined defined regions can be used in defining a region of interest for training. For example, if the device operator would like to select Brodmann's area 4 as a region of interest, the software can outline Brodmann's area 4 on the display, and the device operator can use this information to select the appropriate voxels or area as the region of interest. Anatomically defined regions can include any of the regions defined in a standard reference atlas such as the Talairach atlas or the MNI atlas. Defined regions can also include the saved regions of interest defined for the subject or for previous subjects or groups of subjects. The display can show lines outlining a defined structure. These defined regions when displayed can also be labeled on the display according to their names. This can be useful in localizing anatomical regions in the subject, because it indicates which voxels in the current subject correspond to defined structures in a reference brain. The process of this transformation, which can serve as the input to this display, is described in Examples section 6.

Another type of display panel is an ROI map 10600. This panel may present any of the types of physiological activity maps with one or more regions of interest overlayed. Each region of interest 10610 may be presented in a different color or using a different line weight or line style. The regions of interest may be geometric shapes such as rectangles, circles, or elipses, or they may be selected from an arbitrary combination of pixels. The user may select regions of interest on these displays using a pointing device such as a mouse. This selection can take place either by selecting the corners of a regular geometric shape such as a rectangle, or by selecting the center and diameter of a circle or elipse, or by selecting individual voxels. The regions of interest may be used to select areas from which additional computations will be made, such as computations of activity metrics. The regions of interest may be used in training a subject to modulate a defined region of interest.

Another type of display panel is a Subject information 10700 panel. This panel may present any type of information about the subject that is being scanned or trained, or information about the scan session, such as Subject Name, Age, Weight, Scan Date, Scan Time, Device Operator, Goal of training, brain region being targeted.

Another type of display panel is a Text instructions 10900 panel. This panel may present instructions to a subject in text form. These instructions may be for use in training, or in influencing the subject to improve the course of training. For example, a subject may view the display comprising the instructions and then perform training according to the present invention based on the instructions. These instructions may be commands for what a subject is intended to do in a task. These instructions may be generated or selected by the software of this invention to control the subject's behavior. For example, the software may monitor brain measurements, and determine instructions based on the brain measurements. The subject may then view the display comprising the instructions and perform training according to the present invention based on the instructions. These instructions may be generated by the device operator for presentation to the subject, typically during training. For example, an instructor may input instructions, software taking the instructions and causing them to be displayed to a subject, the subject then performing training according to the present invention based on the displayed instructions. The timing and content of instructions presented on this panel may be generated by the software disclosed, as described in Examples section 3.

Another type of display panel may be a Movement information 11000 panel. This panel may present information about the movement of the subject, computed as described in section 6.B.iv. One item that this panel may include is a trace of movement over time 11050. Another item that this panel may include is a motion scale 11100. Another item that this panel may include is a rotation scale. Another item that this panel may include is translational motion 11200, indicating the motion of voxels in x, y, and/or z direction, or position in x, y, z direction. Another item that this panel may include is rotational motion 11300, indicating motion in roll, pitch and/or yaw. Another item that this panel may include is a time scale 11400, indicating the time points of each measurement. This panel may scroll in time, so that with each new point presented, the older points move along so that a fixed period of time before the present is always visible. Another item that this panel may include is a trial indicator bar 11500. This may indicate some component of a behavioral trial, such as the period of a stimulus or behavior.

This movement information panel may be used by the subject to become aware of when he or she has moved within the scanner. The movement information may allow the subject to realize that they need to be more stationary. The movement information panel may also be used by the device operator to realize that the subject has moved. This might allow them to provide instructions to the subject to be more stationary, or to abort a trial, or a training session. This movement information may also be used to discard data from further processing if the movement exceeds a certain threshold.

Another type of display panel is an Image instructions 11100 panel. This panel may present images meant to convey instructions to a subject. These images may constitute graphical icons known to the subject to denote certain types of behavior. For instance, they may contain images indicating a body part to move, or to imagine moving. These images may be selected by the data analysis/behavioral control software 130, as described in Examples section 3. This presentation of image instructions may be useful in instructing the subject. In particular, the presentation of images may be useful in instructing the subject based upon the brain activity metric measured for the subject, and this may further be useful in guiding subject training. An image instructions panel also has all of the uses described for a Text instructions 10900 panel.

Another type of display panel is a Video instructions 11200 panel. This panel may present video, or moving images. These moving images may constitute instructions for the subject. For example, the subject may be instructed to perform actions, or imagine actions, in accordance with what the subject sees on the video. For example, if the video shows the sequential movement of each finger on the hand, the subject may use this as an instruction to perform those movements. These videos may constitute graphical icons known to the subject to denote certain types of behavior. These videos may be selected by the data analysis/behavioral control software 130, as described in Examples section 3. This presentation of video instructions may be useful in instructing the subject. In particular, the presentation of video may be useful in instructing the subject based upon the brain activity metric measured for the subject, and this may further be useful in guiding subject training. A video instructions panel also has all of the uses described for a Text instructions 10900 panel.

Another type of display panel is a Reward information 11300 panel. This panel may present information to the subject regarding his or her success in training. The computation of information presented on this panel is described in section 6.C. and 6.D. One type of information that may be presented on this panel may be whether a subject was successful on the most recent trial. Another type of information that may be presented on this panel is the level of activity or an activity metric achieved for some period of the most recent trial. Another type of information that may be presented on this panel is the subjects success or failure at the most recent behavioral trial if the subject is performing concurrent behavioral trials. Another type of information that may be presented on this panel may be the target level of activation or an activity panel metric that the subject was supposed to reach. Another type of information that may be presented on this panel may be the challenge level that the subject is at, corresponding to the level of difficulty, or degree of modulation of the region of interest. Another type of information that may be presented on this panel may be whether the difficulty will increase or decrease on the next trial. Another type of information that may be presented on this panel may be a time-out period indicating that the subject has performed a trial incorrectly and will have to wait a period of time before the next trial as a punishment. Some or all of these types of information may be useful in rewarding the subject for performing trials correctly, or punishing the subject for performing trials incorrectly. The subject may view this information to gauge their performance, and may continue or change their strategy and effort level accordingly. This may be beneficial in training the subject.

Another type of display panel is a Behavioral % correct 11400. This panel may present information regarding the subjects behavior on a concurrent behavioral trial such as a visual discrimination task that takes place during training. Another type of information that may be presented on this panel may be the overall percent of trials that the subject has been successful on. Another type of information that may be presented on this panel may be the percent correct for each of a series of different stimuli or behavioral conditions. Another type of information that may be presented on this panel may be the standard errors or standard deviations of performance for each of a series of different stimuli or behavioral conditions. The subject may view this information to gauge their performance, and may continue or change their strategy and effort level accordingly. This may be beneficial in training the subject. These types of information may all be useful in behavioral training of a subject, and/or in concurrent training of the subject to modulate a brain region.

Another type of display panel is a Brain % correct 11500 panel. This panel may present information regarding the subject's successful trial performance in modulating the activity of a defined brain region. One type of information that may be presented on this panel may be the overall percent of trials for which the subject was able to achieve a level of an activity metric higher than the target level. Another type of information that may be presented on this panel may be the percent of trials for which the subject was able to achieve a level of an activity metric higher than the target level for each of a group of stimuli. Another type of information that may be presented on this panel may be the threshold for the subject to achieve a certain percentage of successful trials. Another type of information that may be presented on this panel may be the standard errors or standard deviations of the percent of successful trials for each stimulus. These types of information may all be useful in training of the subject to modulate a brain region. The subject may use this information to gauge their performance, and may continue or change their strategy and effort level accordingly. Another type of information that may be presented on this panel may be icons 11510 for each of the different types of trials, such as stimuli or behaviors. The subject may select these icons using a pointing device to indicate the type of stimuli or behaviors that the subject would like to engage in, or the type of stimulus of behavior to be used in a next trial.

Another type of display panel is an ROI Activity 11600 panel. This panel may present the level of an activity metric measured for a defined region of interest. One type of information that may be presented on this panel may be the trace of the activity metric 11610 measured over some period of time for the region of interest. This may constitute a scrolling panel such that as each new value of the activity metric is computed. The chart values may take positions to show all the most recent values, such as the most recent 100 seconds. Another type of information that may be presented on this panel may be a marker indicating the most recent value of the activity metric 11620. Another type of information that may be presented on this panel may be an indicator of period of one or more behavioral trial 11630, such as an indicator of when some period of a trial was taking place, such as the period of a stimulus, behavior, or activiation. Another type of information that may be presented on this panel may be a target 11640 indicating the level of activation that the subject is instructed to reach on a particular trial. Another type of information that may be presented on this panel may be a scale of values of the activity metric 11650. Another type of information that may be presented on this panel may be a timescale of values of the activity metric 11660. The values used for activity metrics can correspond to any value computed for an activity metric. The computation of these values are described in Examples section 1.D. Multiple copies of an ROI Activity 11600 panel may be present at the same time, allowing comparison of the level of activity between different activity metrics. These may include a trace of the activity metric measured from a background or alternate region of interest 11700. This may provide an indication of an activity metric from a brain region not undergoing training. Another trace that may be presented is a trace of the difference in activity between the region of interest undergoing training and a background region of interest 11800, or a difference between the activation pattern for the current subject and some other subject or a reference subject. Panels 11700 and 11800 may include all of the same features as described for 11600. These panels may be useful in determining the state of activity in a localized brain region in a subject. These panels may also be useful in guiding training of a subject. These panels may also be useful in guiding performance of a subject. These panels may also be useful in determining when a subject will be most likely to perform a trial or task successfully. The subject may view this information to gauge their performance, and may continue or change their strategy and effort level accordingly. This may be beneficial in training the subject.

Another type of display panel is a PETH 11900 panel. This panel may present a peri-event time histogram metric. The computation of these metrics is described in Examples section 1.D.xi. One type of information that may be presented on this panel may be a trace of the peri event time histogram. Another type of information that may be presented on this panel may be a trace of the PETH +/− standard errors. Another type of information that may be presented on this panel may be a trial bar indicating time periods from a trial. Another type of information that may be presented on this panel may be a scale of values of the PETH. Another type of information that may be presented on this panel may be a timescale of values of the PETH. These panels may be useful to the subject and device operator in determining the state of activity in a localized brain region in a subject. These panels may also be useful in guiding training of a subject. These panels may also be useful in guiding performance of a subject. These panels are also useful in defining a region of interest as described in section 4.

Figure 10:
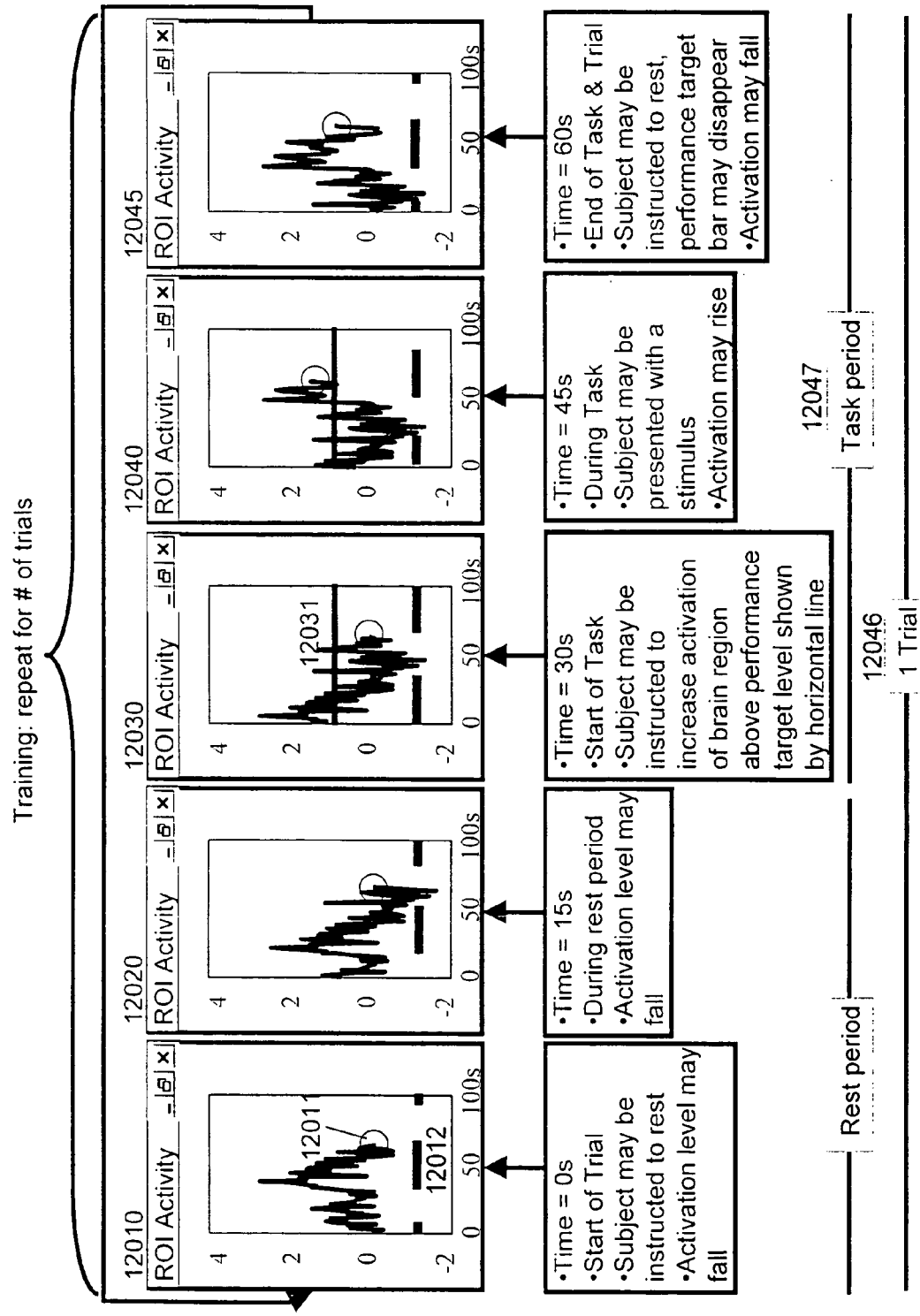
FIG. 10 shows an example time progression of displays on an ROI panel, and the structure of an example trial.
Figure 11:
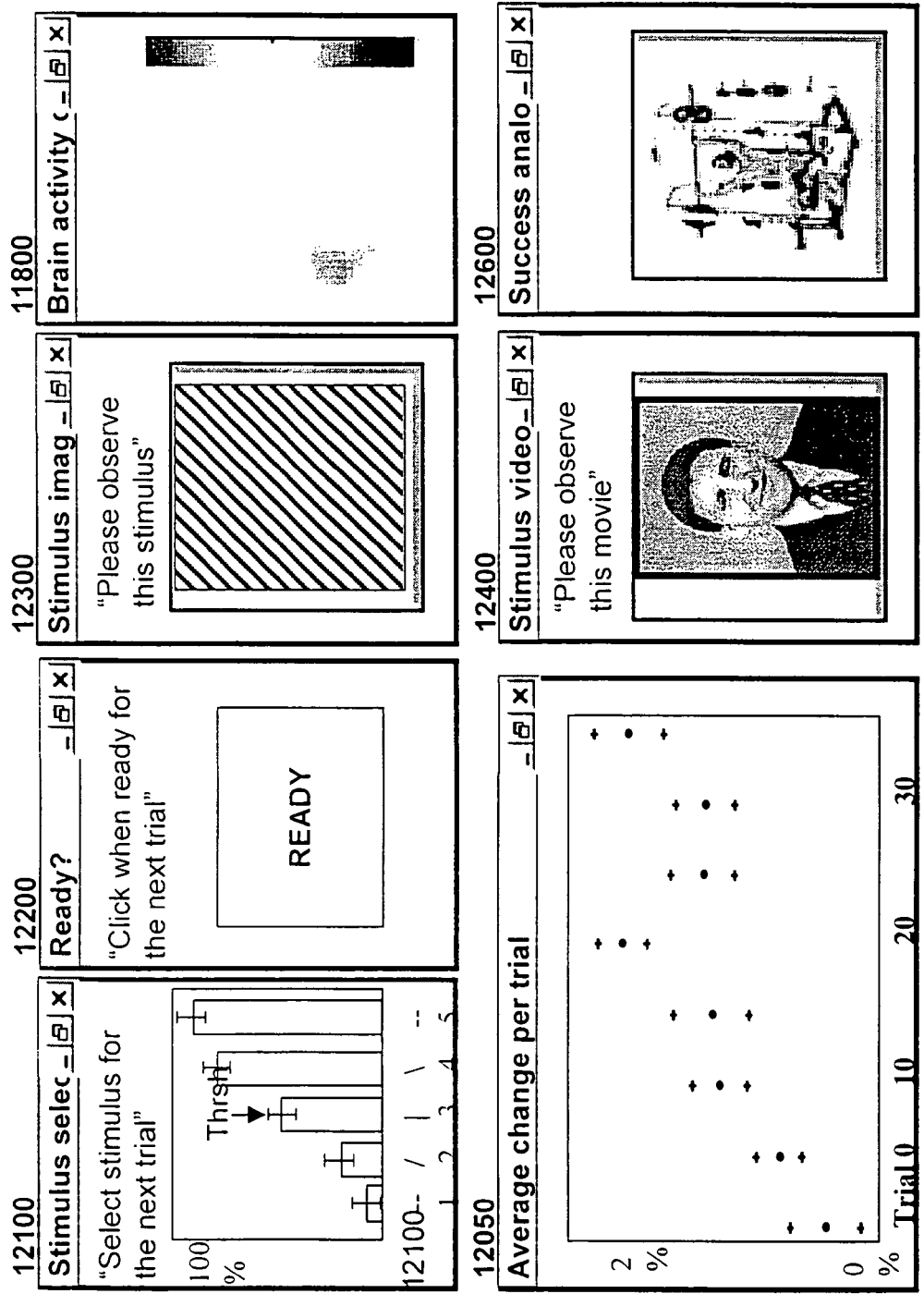
FIG. 11 shows examples of display panels that may be presented.
Figure 12:
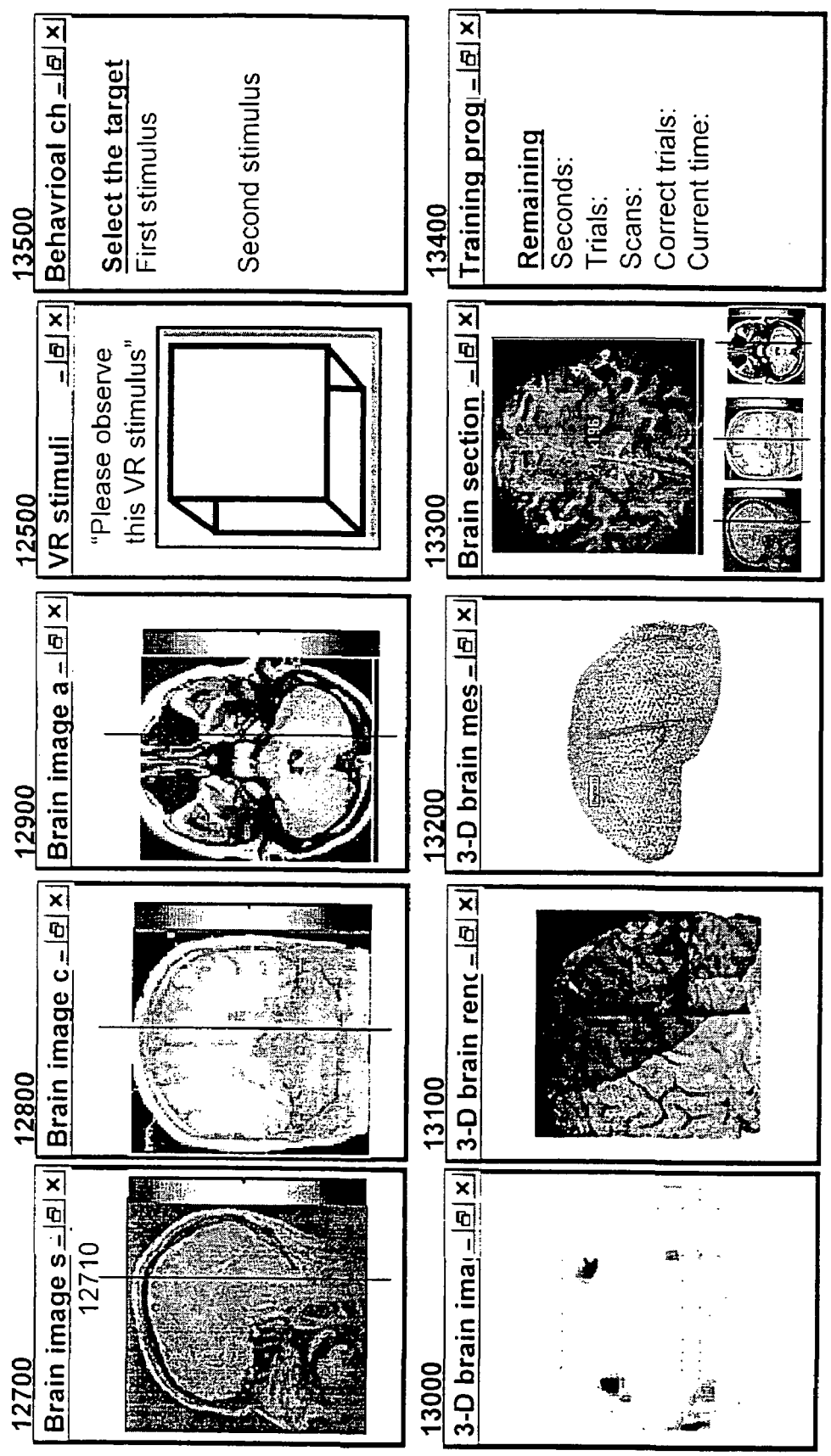
FIG. 12 shows further examples display panels that may be presented.

The various panels described may change in the information that they present from moment to moment. An example of this is depicted in FIG. 10. FIG. 10 shows the same panel, an ROI Activity panel, at 5 different time points during a single trial. The trial lasts 60 seconds, and begins at start time 0, shown in 12010. At this point, the subject's displayed activity metric happens to be fairly low as seen in 12011, and the subject is seen to be at the end of a task period, entering a rest period, as seen in the task indicator bars 12012. At time=15 s in panel 12020, the chart of the activity metric has shifted left by 15 s as new data has been collected and processed. The subject's activity metric continues to be low. At time=30 s in panel 12030, the subject may be instructed to activate a brain region using a defined task, and to achieve a level of the activity metric above the performance target indicated by the horizontal bar 12031, which thereby supports a form of instruction and also serves as an indicator of the subject's past performance. At time=45 s as shown in panel 12040 the subject's activity metric is still up, as intended. The subject may be presented with a stimulus, which may further increase the level of the metric. At time=60 s in panel 12045, the performance target bar may disappear, and/or the subject may be instructed to rest. The entire trial 12046 may last 60 s, and the task period during which the subject activates a brain region may last 30 s. At this time, the next trial is begun. Repeating trials may constitute training of the subject. Continued performance of training may constitute exercise. It should be noted that this example represents only one form of trial. In particular, the durations, ordering, and number of each type of time period, instruction, stimulus, display or other component may vary for different types of trials.

Another type of display panel is an Average change per trial 12050 panel. One type of information that may be presented on this panel may be the difference in an activity metric between two periods in a trial, such as between a stimulus or behavior and a background period. Another type of information that may be presented on this panel may be the average difference in an activity metric between two periods in a trial across several trials, such as between a stimulus or behavior and a background period. Another type of information that may be presented on this panel may be the standard error of this difference. Another type of information that may be presented on this panel may be a timescale of when the trials displayed took place in sequence. Another type of information that may be presented on this panel may be a magnitude scale of the size of the difference measured. These panels may be useful in determining the change of activity in a localized brain region in a subject between conditions. These panels may also be useful in guiding training of a subject. These panels may also be useful in guiding performance of a subject. The subject may view this information to gauge their performance, and may continue or change their strategy and effort level accordingly. This may be beneficial in training the subject.

Another type of display panel is a Stimulus selector 12100 panel. This panel may present icons representing stimuli or behaviors 12100. The subject or device operator may select these icons using a pointing device such as a mouse to select a stimulus or behavior that will be used for training, or that will not be used for training. The subject or device operator may select these icons using a pointing device such as a mouse to select a stimulus or behavior that will be used for the next trial, or that will not be used for the next trial. This panel can include all of the types of information described for panel 11500.

Another type of display panel is a Ready? 12200 panel. This panel may present an indicator which designates that a next trial is ready, or that asks the subject or device operator when they are ready to begin the next trial. The subject or device operator can then be made aware that a trial is ready to begin. The subject or device operator can also optionally use a pointing device or other means of indicating when they are ready to begin a trial. This can be used in aiding a subjects performance of tasks, or aiding a subject in training as described in this invention.

Another type of display panel is a Stimulus images 12300 panel. This panel may present visual stimuli to the subject. These visual stimuli may be selected as described in Examples section 3. The subject may use this display panel to observe and perceive the presented stimuli in accordance with the remainder of this invention. These stimuli may include, for example: 1) photos of faces, 2) photos of objects, 3) photos of the subject, 4) checkerboard stimuli, 5) sin wave or square wave gratings, 6) other types of visual stimuli as described in the physiology and psychological literature. These displays may be used to selectively stimulate activation of defined regions of the subject's brain. These displays may be used as the basis of selection in psychophysical or cognitive behavioral tasks, such as tasks in which the subject must make a selection between different stimuli based upon a defined characteristic. For example, the display may present a nearly vertical grating stimulus, with the subject being required to indicate whether the stimulus was exactly vertical or not. The stimuli presented may enable a two alternative choice task, in which two stimuli are presented, and the subject selects one of the stimuli that possesses a defined feature, such as being an exactly vertical grating as opposed to a slightly tilted grating. These displays may be used as an aid in subject training, including by activating certain brain regions.

Another type of display panel is a Stimulus video 12400 panel. This panel may present video for use in visual stimulation. The subject may use this display panel to observe and perceive the presented stimuli in accordance with the remainder of this invention. These visual stimuli may be selected as described in Examples section 3. These stimuli may include: 1) moving images, 2) cinematographic material, 3) 3-D virtual reality material that simulates a 3-D environment, 4) stimuli designed to stimulation visual motion areas, 6) other types of moving stimuli as described in the physiology and psychological literature. These displays may be used to selectively stimulate activation of defined regions of the subject's brain. These displays may be used as the basis of selection in psychophysical or cognitive behavioral tasks. These displays may be used as an aid in subject training, including by activating certain brain regions. For example, the display may present a nearly vertical moving grating stimulus, with the subject being required to indicate whether the motion was exactly vertical or not.

Another type of display panel is a VR stimuli 12500 panel. This panel may present virtual reality stimuli, such as stimuli designed to simulate a 3-D experience for the subject. This panel may have two sides, one viewed by each eye to form a stereo image.

Another type of display panel is a Success analogy 12600 panel. This panel may present an analogy of the subject's level of success on a current trial. This analogy may be used to indicate the level of an activity metric. The computations of values for activity metrics are described in Examples section 1. Examples of success analogies that may be used to indicate the level of an activity metric include:

1) Bars that increase in length in proportion to the measured level
2) Polygons that increase in size in proportion to the measured level
3) Scrolling charts of the measured level over a period of time
4) Scrolling charts of the rolling average of the measured level
5) Computer games that move more quickly or more slowly, or that 'succeed' in their goal in proportion to the measured activity level
6) Sounds that indicate the presence of a particular measured level
7) Sounds that are proportional to the measured level in some parameter, such as pitch or amplitude
8) Colors that change in proportion to the measured level according to a color map
9) Objects that move at an apparent speed related to the measured level
10) Movie images
11) Objects that assume a position related to the measured level
12) Objects that move at a speed related to a measured level
13) Conceptual 'success analogies' such as the level to which a weight lifter has lifted a weight being correlated with the level of activity in a brain region
14) Metrics can also be presented using auditory cues such as the pitch, frequency, intensity or repeat rate of sounds.

These success analogies are useful in indicating a subject the level of an activity metric. The subject can view the success analogy panel in order to quickly grasp the level of success or activation that they are achieving. The subject can choose which type of success analogy is the most helpful in getting a sense of their success level. These panels are therefore useful in training a subject. They can also be useful in enhancing motivation in a subject.

Another type of display panel is a Brain image saggital 12700 panel, a Brain image coronal 12800 panel, and a Brain image axial 12800 panel. These panels may present aligned images of anatomical or physiological sections through the brain. The alignment bar 12710, which may be present on any of these panels, may indicate the position of section of the other panels with respect to the present panel. The subject or device operator may select the position of the alignment bar to select a new section. By selecting the position of the alignment bar, the user can choose what section will be presented, for either anatomical or physiological section displays. If the user selects the position of the alignment bar on one section to reflect the position of a new plane of section, this may alter what sections are displayed on the remaining to of the three planes of section to correspond to planes at that level. This is useful in selecting sections for defining regions of interest, for substantially real time selection of ROIs, and for aiding in subject training.

Another type of display panel is a 3-D brain transparent 13000 panel, 3-D brain rendered 13100 panel, or a 3-D brain mesh 13200 panel. These panels may present 3-D views of the subject's brain using a variety of algorithms. These algorithms are described in the manuals and literature describing existing fMRI/MRI data analysis packages. The physiological activity of the subject as measured through an activation volume as described in Examples section 1.B. may be depicted in three dimensions. In particular, activation regions or 'blobs' may be superimposed upon 3D images of the brain, or presented so as to show their internal positions relative to the 3D structures as will be familiar to one skilled in the art. In addition, the physiological activity may be overlayed onto the anatomy of the subject. These displays may be made either in the coordinate space of the subject, or in a standard coordinate space such as Talairach space or MNI space. These displays may be useful in localizing regions of interest in three dimensions, or in 3-D in substantially real time. These displays may be useful in determining areas of activation in a subject in 3-D and/or in substantially real time. The subject or device operator may observe these displays to determine the regions activated by a task. The subject or device operator may observe these displays to localize a region of interest for training.

Another type of display panel is a Brain section montage 13300 panel. This panel may present the data described for panels 12700-12800 on a single panel, as well as including controls to allow the user or device operator to rotate the brain image, zoom in and out, and select sections. These selections may be used to update the views shown in other panels corresponding to the same brain. This may be useful in localizing regions of interest and in training subjects. The subject or device operator may interact with this panel to select the view presented of the brain data. This selection may apply throughout the displayed panels, or only to certain panels.

Another type of display panel is a Training progress indicators 13600 panel. This panel may present indicators of the progress through training, such as the number of trials completed, the number remaining, and the time remaining. The subject and device operator can view this panel to determine the progress through training. This can be useful in maintaining the motivation of the subject, and in training.

Another type of display panel is a Behavioral choice 13500 panel. This panel may present choices for a subject, and allow the subject to register responses. These choices may be choices for the subject to make during a concurrently presented behavioral task. For example, if the subject is engaged in a two alternative sequential task, the panel may present the subject with the two choices to select from. The subject may use this panel to select with a pointing device such as a mouse or a joystick which choice they would like to make. This may be useful in behavioral training. This may also be useful in training of brain activation patterns.

E. Combinations of Information Panels

It is noted that one or more different types of information panels may be displayed simultaneously or sequentially. For example, display panels comprising one or more combinations of different types of information including, for example, instructions, physiological measurement related information, subject performance related information, and stimulus information, may be simultaneously displayed. Alternatively, panels of different types of information may be displayed.

By displaying multiple different types of information at the same time or sequentially, different methods according to the present invention may be performed and facilitated. In particular, the subject can be instructed regarding what to do as well as how well the subject is doing during training. For example, by displaying behavior instructions with subject performance related information and/or physiological measurement related information, the subject can be informed regarding his or her performance as the subject performs the training.

3. Selection and Triggering of Measured Information/Stimuli/Instructions

A key element of the current invention regards the generation of information, and the selection of stimuli or instructions to be presented to a subject, as well as the timing of when this presentation will take place. This selection may be made by performing computations on the activity metrics defined above in Examples section 1.D. Selections can be made from a pre-defined set of stimuli or instructions, or stimuli or instructions can be generated de novo. The inputs to this process are one or more of the activity metrics described, plus one or more sets of instructions or stimuli, and optionally plus measurements of a subject's behavior in cases where this is being measured. For this selection process, in some instances one or more stimuli are selected alone, and no instruction is given. In another example one or more instructions are selected alone, and no other form of stimulus is given. In another example, stimuli and instructions are tied together in pre-defined pairs, and one or more pair is selected together. In another example, one or more stimulus and one or more instructions are each selected independently.

The methods of selection and presentation for stimuli and for instructions are conceptually similar, and they will be explained together. For instance, their might be a set of ten visual stimuli, or ten visual images corresponding to instructions to imagine a movement. In either case, the same algorithm could be used to select from among the ten, and the same display means could be used to present them to the subject. However, stimuli or behaviors used and the means of selection must, of course, be appropriate to the goal being sought. This process of generating information for stimulus or behavior selection may be integrated into the various methods of the present invention. For example, the methods may include accessing a subject's likelihood of succeeding at a training activity; and communicating an instruction based on the assessed likelihood.

A. Random Selection

One example of selecting a stimulus is random selection. It may be desired to randomly intermix different stimuli or instructions for behavior. This may be done, for example, when more precise control of the training stimuli is not required, and serves as a default method. Random intermixing may also be used to prevent habituation of neural responses that can take place if the same stimulus or behavior is presented repeatedly on successive trials. In such instances, the stimulus or behavior to be employed for each trial may be selected fully or partially at random from the stimulus set.

B. Selection Based Upon an Activity Metric

Another example of selecting a stimulus is stimulus selection based upon an activity metric measured from a region of interest. In this example, stimuli may be selected based upon the level of an activity metric. For example, each of a set of stimuli may be assigned to one range of the activity metric, so that if the activity metric is within this range then that stimulus will be presented. For example, if the activity metric varies approximately evenly from 0-1% over time, then each one of ten stimuli might correspond to a range of 0.1% of the range in the activity metric, from 0-0.1% for the first stimulus, up to 0.9-1% for the last stimulus. At the moment that a stimulus should be presented to a subject, the activity metric value is measured, and the stimulus is selected whose range corresponds to the measured value. A use for this method in training is that some stimuli are more challenging than others, and this method can match the more challenging stimuli to the periods of higher (or lower) activation of a region of interest involved in the perceptual processing of those stimuli. One example of this use is that overall trial performance can be improved if activation metrics are used to select stimuli or behaviors. Subjects can perform tasks more effectively, learn and remember more effectively, and undergo more effective and more rapid learning and training when the appropriate stimulus or behavior is selected for the observed value of the activity metric for a relevant region of interest.

Another example of selecting a stimulus is stimulus selection based upon a likelihood of behavioral success metric. The use of these metrics to select stimuli and instructions can also be used to help subjects to perform tasks more effectively, learn and remember more effectively, and undergo more effective and more rapid learning and training. If a likelihood of behavioral success metric has been computed (as explained above in Examples section 1.D.xii.) for each of two or more stimuli, then at different moments, the likelihood of success metric will be different for each of the stimuli. Stimuli may be selected based upon the stimulus with the highest current likelihood of success metric given the current activity metric. However, the overall likelihood of success metric may be higher for one of the two stimuli, so it may be preferable to use a measure of the difference between the current likelihood of success and the average likelihood of success for each stimulus. This way, the stimulus will be selected whose likelihood of success is the most elevated from its average level. Using likelihood of success metrics can improve the overall performance of subjects in performing tasks, and in behavioral training, because subjects are, on average, presented with stimuli and tasks that they are more likely to succeed with at the moment that they are presented.

Another example of selecting a stimulus is selection based upon a spatial pattern comparison metric. A target pattern may be selected. This target pattern may correspond to the average pattern activated by each stimulus or behavior. The target pattern may correspond to the pattern measured for successfully completed trials or for unsuccessful trials for a given stimulus or behavior. When a spatial pattern comparison metric reaches a target level of similarity between the observed pattern and the target pattern for a given stimulus or behavior, then that stimulus or instruction is presented. This can be used to present stimuli or instructions when the subject is most likely to successful with that stimulus or task.

Another example of selecting a stimulus is selection based upon a performance target level. A stimulus that may be presented to that subject is a representation of the performance target that the subject is supposed to achieve. The level of the target presented may be selected based upon the computed level of a performance target. A performance target may be presented, for example, on an ROI activity panel 11600. Other kinds of stimuli may also be selected based upon a performance target. For example, different stimuli or sets of stimuli from a stimulus set may be associated with different levels of a performance target. Some stimuli may be more challenging to perceive or discriminate, and these may be associated with higher or lower values of the performance target. For example, when the performance target is high, the subject is presented with more challenging stimuli.

C. Selection by the Subject or Device Operator

Another example of selecting a stimulus is selection by the subject or the device operator. Through observing the conducting of trials, and the resultant activity maps and activation metrics displayed, the subject or device operator may form an opinion as to what stimulus will be best. Either the subject or the device operator may select the stimuli or behaviors for use from the selected stimuli or instructions for behavior set, using one of the display panels designed for the purpose, such as shown in 11500, 12100. This process may comprise having a subject perform a plurality of trials involving different stimuli and/or behaviors, measuring and displaying activity metrics during the plurality of trials, having the subject select one or more of the different stimuli and or behaviors to perform on a future trial based upon a review of the measured activation from the plurality of trials.

D. Creating a Stimulus or Behavior Continuum Corresponding to a Level of Activation In another example, stimuli or behaviors are created de novo along a pre-defined continuum described by one or more parameter. That continuum is formed into a correspondence with levels of an activity metric that allows automated choice of the one or more parameter that defines the stimuli based upon the activity metric level as measured at or just before the time that a stimulus should be presented to the subject. For example, given a visual sin wave grating stimulus that can have any period based upon a parameter that varies from 0.1-1 cycles/degree, and an activity metric with continuous values from 0.1-1%, a sin wave grating stimulus can be created de novo based upon the value of an input parameter (cycles/degree) corresponding to the level of an activity metric. Stimuli with a higher value of the cycles/degree parameter may be more challenging to perceive or discriminate, so it may be useful to select those stimuli at times of higher measured activation for a region of interest involved in perceptual processing of the visual stimuli. This can also be done for instructions. For instance, a smooth continuum in the location of the target of a pointing exercise can be made to correspond to the level of an activity metric in a brain area involved in the generation of this motor behavior.

E. Identifying when to Begin a Trial

It is often desirable for a subject to begin a particular trial or part of a trial, or receive a stimulus or engage in a particular action, or training exercise, at a moment that is determined based upon the measured physiological activity up to that point. The data analysis/behavioral control software 130 can function to select time points for initiation of a trial when a particular activity metric is at a high or low value, or crosses a threshold value. Subjects can perform tasks more effectively, learn and remember more effectively, and undergo more effective and more rapid learning and training when trials are begun at times when the observed value of the activity metric for a relevant region of interest is above a threshold value.

Another example of identifying when to begin a trial is beginning a trial when an activity metric measured from a region of interest involved in mediating a task being performed by a subject has reached a criterion level, such as a criterion activation level. For example, subjects can perform more effectively at a behavioral task if the start time for task trials is selected based upon the level of activation for the brain regions of interest involved in mediating that task reaching a threshold. If a subject is performing a visual discrimination task involving representation by a particular sub-region of the visual cortex such as a motion detection task using randomly moving dots, then visual discrimination trials may be initiated when an activity metric measuring the level of activation for this sub-region of interest reaches a criterion level, such as an activation criterion level reached by a the sub-region of visual areas V1 or MT that mediates visual perception of the visual area corresponding to the position of the dots.

Another example of identifying when to begin a trial is beginning a trial when an activity metric measured from a region of interest undergoing training by a subject has reached a criterion level, such as a criterion activation level. If a subject is performing a motor task involving a particular sub-region of the motor cortex, or is being trained to activate that region of the motor cortex, then trials may be initiated when an activity metric measuring the level of activation for this sub-region of the motor cortex reaches a criterion level.

Another example of identifying when to begin a trial is beginning a trial when an activity metric measured from a region of interest has reached a criterion level, such as a criterion likelihood of success level. For example, as assessed using a likelihood of success metric, subjects may be able to perform a task more effectively when the task is started at times that are selected because a likelihood of success metric as defined above in Examples section 1 has reached a threshold value. For example, if a subject is performing a visual discrimination task such as a motion detection task using randomly moving dots described above, and a measure of the average likelihood of success at the task has been determined for each of several levels of activation in a sub-region of the visual cortex involved in mediating the task, then the task may be begun when the level of activation of the measured region of interest corresponds to a criterion likelihood of success in performing the task. Likelihood of success metric computation is described further in Examples section 1.

Another example of identifying when to begin a trial is beginning a trial when an activity metric measured from a region of interest has reached a criterion level, such as a spatial pattern comparison metric. A target pattern may be selected, and an activity metric may be computed that measures the similarity of this target pattern with the currently observed pattern, as described in Examples section 1. A trial may be begun when this metric reaches a criterion level. The target pattern may correspond to the average spatial activation pattern measured for the region of interest during successful trials. When a comparison metric that measures the dot product between the target pattern and the current pattern reaches a threshold value, a trial may be instigated. This can be used to present stimuli or instructions when the subject is most likely to be successful or have a positive outcome for a stimulus or task. Therefore, this can be used to facilitate successful training and exercise.

F. Identifying when to Provide Training Reinforcement

As training is performed, it is advantageous to provide information to the subject to reinforce their training efforts. For example, when a subject reaches a target level of performance, it is advantageous to provide this information to the subject. In one embodiment, software communicates a message of positive reinforcement (e.g., Good job!) when a desired level of activation is achieved. In another embodiment, software communicates a message of negative reinforcement (e.g., Focus!, or Time for a break?) when the subject's activation is not at a level that is desired or would be expected.

4. Modes of Communication with a Subject

A variety of different modes of communication can be used to relay information between the subject and another party, for example a medical professional. For example, information may be communicated between people, transmitted through a direct electrical connection to a nearby point, or through a connection mediated by land-line or wireless telecommunications equipment or the internet. Various examples of how information may be communicated in the system of the present invention are provided below.

A. Two Way Audio and/or Video Communication

According to this variation, the voice of the subject is picked up using a microphone within the apparatus, transmitted, amplified, and played to the device operator or other healthcare professional, either nearby or distant. This recording can be turned off automatically or manually during the process of scanning. The voice of the device operator or other healthcare professional is picked up using a microphone, transmitted, amplified, and played to the subject. In some instances, one-way or two-way video communication is also used by imaging the patient in substantially real time and presenting the image to the device operator or other healthcare professional, or imaging the device operator or other healthcare professional and presenting the image to the subject in substantially real time on the monitor viewed by the subject.

B. Subject Control of Computer Interface

According to this variation, a computer interface is provided that allows the subject to input information. A wide variety of input devices are known, including, but not limited to computer joystick, mouse, trackball, keyboard, keypad or touch-screen, a botton-box with response buttons that the subject can press, game controller devices, and other computer interface means. These devices can also allowed shared control of a pointer or cursor on a computer with a pointing device controlled by the device operator, such that either device can be used to control the pointer or cursor.

5. Sound Cancelling Headphones

In order to increase patient comfort within the scanner, which can be loud when operational, subjects may be provided with sound cancelling headphones. These headphones can be used to produce an opposite waveform to the sound produced by the scanner. This can be accomplished by using a microphone close to the subject to measure recorded sound, and providing an appropriately amplified complementary signal to defeat the sound heard by the subject. Equipment designed for the purpose is, for example, the Instructioner produced by Resonance Technology, CA.

Sound cancellation can also be accomplished by providing an amplified, digitized, pre-recorded waveform to the subject that is substantially the opposite of the repeated sound waveform produced by the scanner. The subject or device operator is then allowed to adjust the delay of this repeated signal with respect to the scanner noise and the amplification of this signal so as to produce the maximal sound cancellation.

This signal may be presented using either headphones worn by the subject, or using headphones or earplugs with sound-conductive tubing that lead sounds to the subject's ears from a speaker outside of the measurement apparatus.

Figure 9:
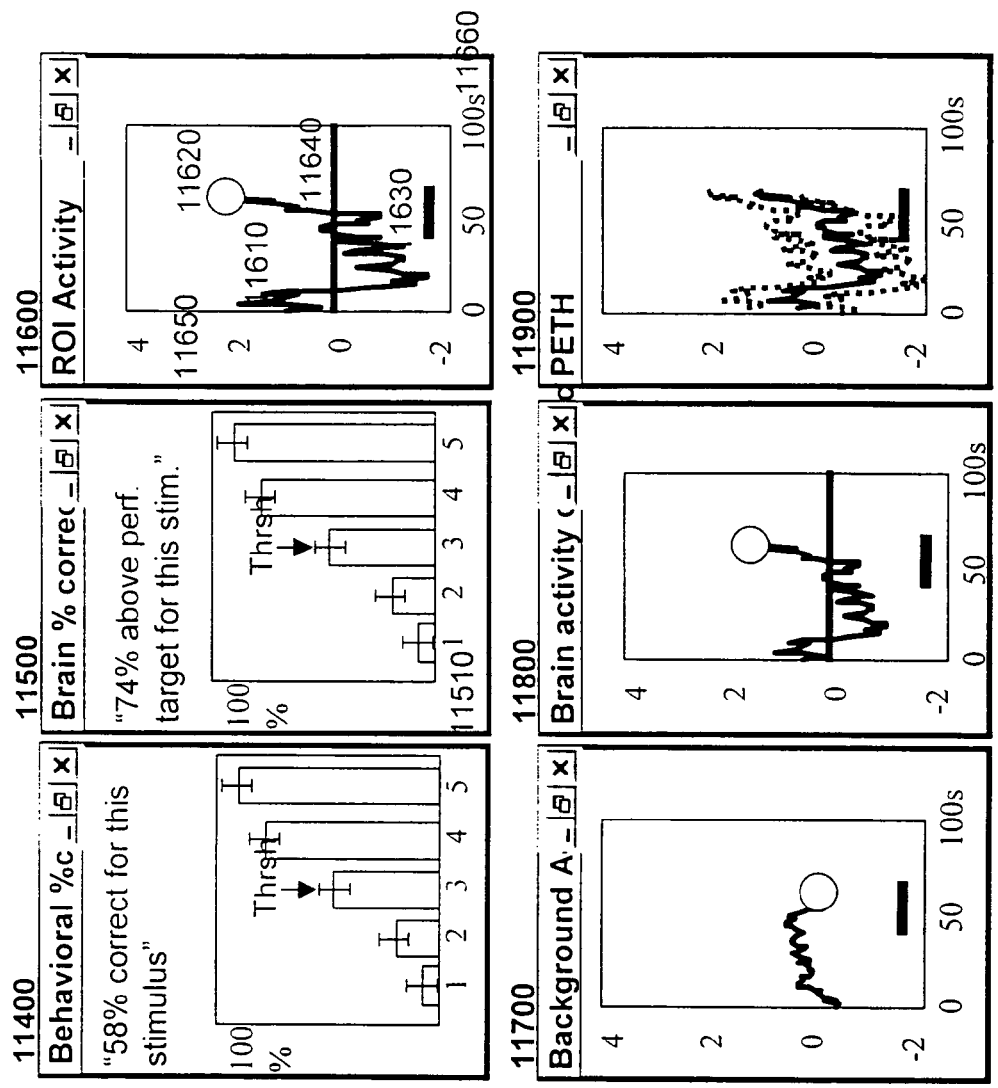
FIG. 9 shows further examples of display panels that may be presented.

6. Localization of Structures Using Standard Coordinates, and Coordinate Transforms This section describes several ways in which one may localize regions of interest from on physiological scan data. If a given anatomically-defined region is to be used as the region of interest for a subject, software may be used to select the voxels of a given subject's physiological and anatomical brain scanning volume corresponding to that anatomically-defined region. This selection may take place in substantially real time. For example, the user may select an anatomical region of interest from a pre-defined database of anatomical regions. Software may then be used to determine the voxels within the physiological or anatomical scans of the subject that correspond to the selected structure. The software can also highlight the structure, draw an outline around it in 2-D or 3-D representations of the subject's brain, and label the structure. The software can also be used to label all structures on a given section of the subject's brain, or all structures that match a selected criterion, such as all cortical areas. The software can also use custom anatomical boundaries defined by the user, which can also be added to this database. Examples of this functionality are shown in FIG. 9.

The first step in this process is for the device operator to select the anatomical area of interest from a standard coordinate system brain, such as the Talairach Atlas or the MNI Atlas with corresponding coordinate system. The device operator can do this by using a text designation of the area of interest (such as a particular Brodmann's Area). This text designation can be either selected from a pull-down menu of pre-defined choices corresponding to the anatomical areas taken from an atlas plus user-defined areas, or entered as free text. This text designation is searched from a database of which voxels correspond to which anatomical areas to produce a list of corresponding voxels. Additional areas defined in the same way can be added to create a combined area, or subtracted to create a difference area. Alternatively, the user can select the region of interest from one or more planes of an anatomical map in standard coordinates. These selected voxels from the standard brain can be saved to disk as a brain volume mask, or as a list of voxel points, and used at the time of scanning.

The transform from standard coordinates to the coordinates of a particular subject being measured must then be defined. This takes place by the user designating a variety of points on the subject's brain that will be used to correspond these points to the pre-defined standard coordinate brain, as shown in FIG. 9a. The first point selected will normally be the anterior commissure, shown on a mid-sagittal section. The program will assume that the subject's brain is identical to the standard coordinate brain, and present on the display the point corresponding to the anterior commissure in a standard brain as a target on top of the section of the subject's brain as a background, while also presenting text designating the name of the structure: "anterior commissure". The device operator can select a different section as the background section. The device operator then mouse-clicks the point of the anterior commissure on the actual section of the brain of the subject as seen in the background section. The program will take in the point of the anterior commissure in 3-D coordinates, so that it can be compared with the reference brain point. The difference in position between the point in the standard coordinate brain and the point measured for the subject's brain is added to subsequent points before they are displayed to the subject, to shift the display point to be closer to that observed for the subject. The program will then go through a variety of additional points in succession and present targets for the point on the subject's brain; the user will select the point of the anatomical location on the subject's brain; and the program will take in this data. The targets are used so that the user may more quickly select each corresponding point on the subject's measured brain volume, without reading a text description of the relevant area to select. The points used will include: anterior commissure, posterior commissure, occipital pole, frontal pole, rostral pole (normally all selected on a mid-saggital section), left and right extremes of brain (normally selected on a coronal or axial or horizontal section). Additional points can be used for an even better fit. Once the locations of all of these points in the standard coordinate brain, and in the measurements for the subject's scan volume, the 3-D to 3-D affine transformation is computed using standard methods that produces the least-squared error in transforming the points in the standard coordinate brain to the points in the subject's observed brain volume. This transformation takes into account translation, rotation, and scaling to locate corresponding points within the subject's physiological or anatomical scanning volumes with those from the standard coordinate brain. This transformation will be used to make the correspondence between all other points. This process can take place while the subject is in the scanner, in a matter of seconds or minutes from the time the data is actually collected, and using the same computers and software used in the scanning and substantially real time data transformation procedures.

If necessary, more complex transforms can be computed, including internal morphing to allow more precise correspondence between defined anatomical points within the two structures with interpolation of the correspondences of points intervening between the defined anatomical points. Also, the transformation can take place by automatic registration of brain volumes (see for example methods described in SPM99 and other existing MRI/fMRI/PET data processing packages).

Once the transformation has been determined, any point in the standard brain can be translated to find the corresponding point(s) in the subject's brain scan volume, and vis. versa. Therefore, a volume mask is generated corresponding to every point in the subject's brain volume that corresponds to a point from the anatomical structure(s) selected by the device user. This volume mask can be overlayed upon the subject's brain images to allow the user to more easily and accurately select the location of a region of interest, or the volume mask can be used as a region of interest itself.

Each voxel in the subject's brain can be assigned a fractional probability of being within a defined brain structure. To do this, all of the points from the standard brain that correspond to a given point in the subject's measured brain volume are determined, along with the fraction of overlap, which is used as a weighting factor. The fractional probability of being within a given structure is then determined as the sum of (the product of each corresponding pixel's being within that structure as determined from existing atlas data, times that pixels weighting factor.)

The software can function in the reverse direction, providing a spatial readout of the location in standard coordinate space of a given location in the brain of a subject selected by the device operator on a screen display, based upon reverse the vector transform. In addition, the resultant location in the standard coordinate space can be used to perform a lookup function within the 3-D database in order to produce the name of the anatomical structure at the corresponding location. Finally, the anatomical boundaries of the structure selected within the subject's brain can be drawn and labeled as a contour map surrounding all voxels included within the structure, or having a threshold probability of being within the structure.

7. Summary of Scanning Scanning Protocol

In this section, an exemplary scanning protocol is provided. It is pointed out that this protocol is for illustration purposes and may be modified as has been described in the other sections. It is also pointed out that aspects of this protocol are directed to performing a fMRI scan. Modifications to the protocol are within the level of skill in the art for other brain scanning methodologies.

After pre-scanning training has been performed, subjects are first placed in the scanner, and a series of scans take place over a period of minutes or hours.

T1-weighted saggittal localization scans are conducted to localize the brain precisely and achieve registration.

T1-weighted anatomical scans are also conducted to precisely image the brain and central nervous system Functional scan(s) may then be performed to localize the regions of interest. During these scans, the subject may be asked to perform a task alternating with rest periods (with each typically lasting about 30 s). After this has been repeated 3-20 times, the average activity may be computed for each voxel within the brain or other body zone in order to determine the region(s) of interest as described above. During this process, the subject observes images of the activity pattern within their brain so that they learn what the activation achieved by a behavior in a particular region looks like, and are encouraged by their success.

Initial training scanning is then performed to train the subject in how to control a brain region. The subject can be asked to control a region of the brain that is 'easier' to control than the ultimate training target so that they learn how to accomplish this and build confidence. In one embodiment, subjects are asked to alternatively activate and inactivate their functionally defined primary motor cortex digit representation of one hand by imagined hand movement. The subjects learn how to control this brain region and are rewarded for their correct performance.

The subject may be given a 'control task' which is identical to the task described below, except that the information presented to the subject does not give accurate information about the state of activation of their brain. The information presented comes from another (pre-recorded) subject, from a different brain region than the one being considered, from an earlier time, or a combination. In one embodiment, the subjects may be given 'sham feedback' which they are told comes from the region of interest the second before, but actually comes from another brain region 30-60 s before. This allows the clear determination that subjects are using the information being presented to them to control their brain activation (in comparison with this control case where they are not).

The subjects may be given multiple training periods of many trials or continuous training. The subjects are shown the screens described above, and asked to perform many trials at the times cued. In each trial, the subject alternated between performing the desired task and resting or performing a different task. The subject is instructed to achieve the desired pattern of brain activation. In one embodiment, this desired pattern is an increase in activation in a defined brain region during the task period compared with the control period. As the subjects progress through the trials, in one embodiment an adaptive tracking procedure is used to aid in their training. This procedure sets a target level of activation for each trial based upon the level achieved in recent trials (using a psychophysical 3 up, one down procedure). As the subject does better, the trials become more challenging. If the subject begins to make errors, the trails become easier. The subject is given both continuous immediate information about the level of activation in the relevant brain region, as well as information about their behavioral performance. This training takes place either using the alternating methodology described, or with the subject's objective being a continuous increase in activation of the target region, or replication of the intended pattern.

The subjects are then given test periods to simulate being outside of the scanner. On certain trials, or periods of trials, subjects are not provided with information about the level of brain activity, and they are tested to determine whether they are nonetheless able to produce the desired modulations. This simulates the situation that the subject will encounter in controlling their brain activation state when no longer in the scanner, and allows the evaluation of their success.

8. Scanning Parameters

For fMRI, an example of scanning parameters that may be used is as follows. It is noted that one of ordinary skill will know how to perform fMRI and thus will know how to deviate as necessary from these parameters.

Scanner fields can range from 0.1-10 Tesla or more. Scan volumes can range from 1 mm to 40 cm, and can be divided into voxels with edge sizes from 1 micron to 20 cm. Scan repeat rates can be 0.01 to 1000 Hz. TE can range from 1-1000 ms, and TR can range from 1-4000 ms.

9. Contrast Agents

It is noted that contrast agents may be optionally used in combination with fMRI for physiological signal measurement when performing the various methods of the present invention. By using contrast agents to assist brain scanning, it may be possible to achieve larger and more reliable activation measurements than using tradition BOLD signals which rely on endogenous contrast particularly as provided by hemoglobin. Examples of exogenous contrast agents that may be used in conjunction with the methods of the present invention include, but are not limited to the contrast agents disclosed in U.S. Pat. No. 6,321,105.

10. Background Conditions

Background conditions for training and measurement are used to set the 'baseline' level of a localized brain region's activation, or another activity metric. Further measurements can be made in comparison to this baseline. For example, a subject might be trained to increase the level of activation of a localized brain region above a baseline level, and that baseline level might be determined by the activation of that region when the subject is resting and not performing a task. If a different baseline level was chosen, such as the level when the subject performed an alternative task, then the increase above this alternative baseline level would be different. Frequently, the activity pattern measure of interest is the difference in activity between a task state and a baseline level measured for a background condition. Therefore, it is important to select an appropriate background condition.

As was described previously, the simplest background condition is typically a rest condition during which the subject is not explicitly instructed to perceived particular stimuli or perform particular behaviors. However, there are circumstances and brain regions for which 'rest' can still produce significant levels of activation. For example, if at 'rest' the subject tends to engage in cognitive activities such as internal dialog or other types of thoughts, there can be activation of certain brain regions associated with these cognitive activities, such as in the frontal lobes.

More complex background conditions are designed to selectively deactivate a region of interest, or to activate other regions than the region of interest. For example, a background condition for a verbal mental rehearsal task is the task of imagining mental images in the absence of internal verbalization. This background condition may lead to a lower or different pattern of activation in the region of interest, such as in the region responsible for verbal mental rehearsal. This background condition may also lead to an increase in activation in other regions, such as occipital and frontal regions responsible for internal visualization. Other background conditions include tasks that will inhibit subjects from engaging excessively in unrelated thoughts, such as a simple reaction time task or a task require select which stimulus was presented of several possibilities. In some instances a background condition to measure a truly low level of activity could be one of the various states of sleep such as slow wave or REM sleep, anesthesia, or other reduced level of awareness.

11. Head Motion Stabilization

For many of the brain scanning technologies, it is important for the subject's head to be kept stationary. This becomes an issue when the subject is trained for an extended period of time. Accordingly, the present invention also relates to devices reduce head movement. Movement cancellation software and technologies may allow less restrained head movement or free head movement during measurement using this invention.

In one embodiment, the subject is placed within a head restraint system similar to the type used following cervical spinal injury. The restraint system may be anchored or placed in such a way as to ensure stability, minimize motion, and allow reproducible placement of the head in space within the scanner on successive occasions. The restraint system preferably is able to conform to a shape of the head and neck of the subject and may include adjustable straps to hold the head securely within the device. The materials used may be semi-rigid or a combination of hard materials coated with softer material to make them comfortable, with all materials being scanning transparent.

In another embodiment, a custom-fitted head mold is provided to hold the head of the subject stationary. This mold is preferably removeably attachable to the scanner so that the mold may be immobilized relative to the scanner. The mold may be created through injection molding using a lightweight, largely rigid yet somewhat soft, and scanning-transparent material such as styrofoam to form a mold shaped to fit all or part of the subject's head, neck, and upper torso. Optionally, the subject's head motion may be additionally stabilized using a bite bar that is placed to allow the subject to embed his/her teach within the material and thereby maintain a fixed position.

For some applications, such as fMRI, it is desirable to precisely position the subject's head, for example relative to the scanner scanner or head coil. This positioning of the head may be accomplished by placing the subject in the scanner so as to precisely locate points on the head by matching localization points with physically constant or precisely adjustable locations attached to the scanner or head coil. In one variation, large plastic or other screws are threaded through holes in the apparatus holding the subject and adjacent to the head may be used. These screws may be screwed in until they just touch the head of the subject, with the number of turns providing a precise a reproducible measure of the location of the point on the head. The screws can also be formed with soft pads attached to their ends that serve to restrain motion of the head. Conventional neurological 'halos' can be adapted to this purpose.

Figure 13:
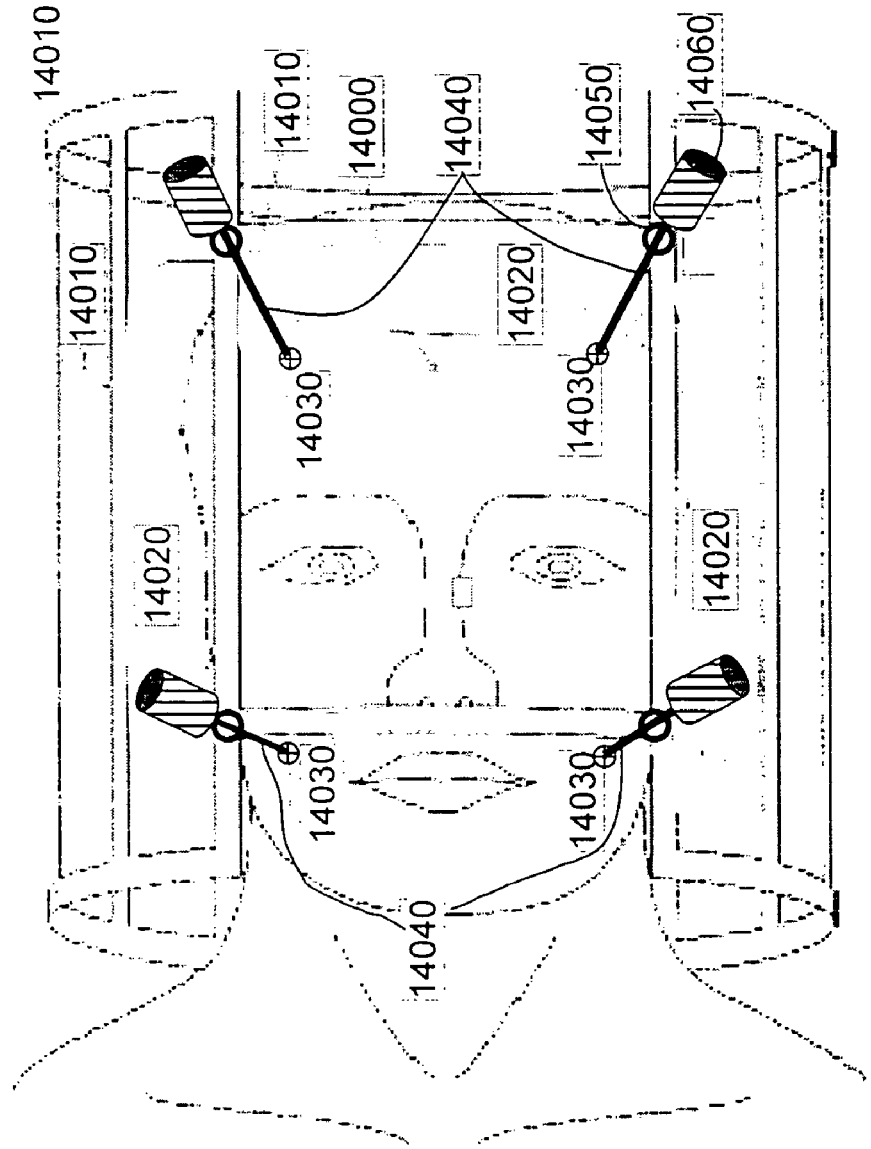
FIG. 13 shows a diagram of an apparatus for stabilizing the head of a subject, which may be particularly suited for use in early and experimental implementations of the device when free head-movement technology is not available.

FIG. 13 shows an embodiment of head motion restraint for the subject. The subject 14000, is placed within a rigid structure 14010 that may be positioned within the measurement apparatus, such as an fMRI scanner. The rigid structure 14010 may serve be function of being an RF receiver coil apparatus. The head of the subject is immobilized in a conformal head mold 14020 that may be selected from a pre-existing stock, may be custom fitted for the subject, or may be injection molded or otherwise fashioned to be in the shape to fit around a portion of the subject's head. Localization points on the subject 14030 may be used to ensure constant placement within the apparatus. These points may be matched up with the ends of either fixed or adjustable positioning members 14040 that are attached to the rigid structure. The positions of these positioning members may be reproducible across scanning sessions. By maintaining contact between the localization points 14030 and the positioning members 14040, the position of the subject's head within the scanner may be held constant. The positioning members may be adjustable in position with respect to the rigid structure 14010. For example, the positioning members may be threaded screws that fit through holes 14050 in the rigid structure and have screw heads 14060 that allow their position to be adjusted. The screw threads and position of the screw heads may be calibrated and marked so that a repeatable depth of the screw may be achieved on successive instances. More sophisticated positioning means be used for the positioning members, such as micromanipulators, for example those manufactured by Kopf, Inc. or Narishige, Inc. Any number of positioning members 14040 may be used such as 1, 2, 3, 4, 6, 8, 10 or more. In addition, the positioning members may be placed on any position on the rigid structure 14010 that will allow them to contact a portion of the body of the subject, such as the top, bottom, sides, front and back of the head. The rigid structure 14010 may also correspond to a neurological or neurosurgical 'halo', or to a structure adapted from a halo for the present purpose by attachment to an MRI RF receiver coil or other element that can be precisely positioned within a measurement apparatus such as an MRI scanner.

12. Cardiac and Respiratory Gating

Some portions of the brain undergo significant movement as a result of the cardiac cycle as well as respiration, and these movements introduce noise into physiological signals measured from the corresponding scan volume voxels. The present invention can be used in combination with techniques that decrease the impact on measured physiological data of physiologically-based motion such as cardiac motion and respiratory motion. One technology that may be used to decrease the observed motion of certain brain regions is cardiac gating. Brain measurement times are triggered by measurements of the timing or phase of the cardiac rhythm cycle so that, on average, successive brain measurements are taken at substantially the same point in the cycle with brain regions in substantially the same position. For instance, the start of each cardiac cycle is detected using an EKG or pulsoxymetry device, and this time is used to trigger the presentation of an MRI RF pulse sequence and ensuing measurements.

Another technology that may be used to decrease the observed motion of certain brain regions is respiratory gating. Brain measurement times are triggered by measurements of the timing or phase of the respiratory rhythm cycle so that, on average, successive brain measurements are taken at substantially the same point in the cycle with brain regions in substantially the same position. For instance, the start of each respiratory cycle is detected using a pulsoxymetry device, and this time is used to trigger the presentation of an MRI RF pulse sequence and ensuing measurements.

13. Measurement of Activity

This invention may be used in conjunction with a variety of means for measuring physiological activity from a subject. Examples of measurement technologies include, but are not limited to, functional magnetic resonance imaging (fMRI), PET, SPECT, magnetic resonance angiography (MRA), diffusion tensor imaging (DTI), trans-cranial ultrasound and trans-cranial doppler shift ultrasound. It is anticipated that future technologies may be developed that also allow for the measurement of activity from localized brain regions, preferably in substantially real time. Once developed, these technologies may also be used with the current invention. These measurement techniques may also be used in combination, and in combination with other measurement techniques such as EEG, EKG, neuronal recording, local field potential recording, ultrasound, oximetry, peripheral pulsoximetry, near infrared spectroscopy, blood pressure recording, impedence measurements, measurements of central or peripheral reflexes, measurements of blood gases or chemical composition, measurements of temperature, measurements of emitted radiation, measurements of absorbed radiation, spectrophotometric measurements, measurements of central and peripheral reflexes, and anatomical methods including X-Ray/CT, ultrasound and others.

Any localized region within the brain, nervous system, or other parts of the body that is measured using physiological monitoring equipment as described (or other physiological monitoring equipment that may be devised) may be used as the region of interest of this method. For example, if measurement equipment is used for the monitoring of activity in a portion of the peripheral nervous system, such as a peripheral ganglion, then subjects may be trained in the regulation of activity of that peripheral ganglion. In addition, this invention may be used to monitor the blood, blood volume, blood oxygenation level, and blood flow in the vasculature of the brain and other bodily areas, which may serve as regions of interest.

14. Behavioral Training

Using this invention, subjects may be trained in a variety of tasks. Training corresponds to performing a task with the intent to improve at a desired outcome, and is typically repeated. Tasks may include covert behavioral tasks in which a subject performs a cognitive or mental activity such as imagining a movement in order to activate a brain region, or overt behavioral tasks in which a subject performs a physically observable action such as making a prescribed movement or responding to a question. In either case, the task may lead to changes in the activity of the brain of the subject, and these changes may be measured as provided for in this invention. Overt and covert tasks may be performed separately, or substantially concurrently.

One example of behavioral training is covert training of a subject to activate a brain region of interest. In this example, the subject may be provided with information about the level of activity in a brain region of interest, such as an activity map including the region, or an activity metric that measures the activity in the region of interest. This training may be with the intent of increasing the activity in the region of interest, decreasing it, changing its pattern, or altering it in other ways as measured by the activity pattern metrics described in Examples section 1. The subject may also be presented with stimuli, which may additionally serve to activate a brain region of interest. The subject may also be presented with performance information indicating his or her level of performance at the task being performed. The subject may monitor these types of measured information, stimuli, and performance information, and may respond to them. One response of the subject may be to select or modify a cognitive strategy that the subject uses to activate the brain region. For example, if the subject is performing the covert task of imagining a given hand movement in an attempt to activate the motor cortex, the subject may observe that one particular imagined hand movement is more effective at activating the motor cortex than another particular imagined hand movement. The subject may then select the more effective movement for use in future trials. This monitoring of information and response may take place in combination with performing training. While the results of a covert task may be observed using physiological measurement equipment, they are not observable in the sense of producing an overt, physically observable, visibly viewable action of the subject.

Another example of behavioral training is overt training of a subject to perform a physically observable, overt task. The subject may engage in overt tasks such as psychological, learning, motor, or psychophysical tasks. These may include such as things as making a computer selection of which of two stimuli presented has a particular feature, or making a prescribed motion, or answering a stated question. The subject may additionally be given performance information regarding their performance at these covert tasks, such as whether they performed tasks correctly or incorrectly. The performance of covert tasks may take place substantially concurrently with overt tasks. For example, the subject may be instructed to make selections between different stimuli or to perform particular movements while the subject also attempts to increase the level of activation in a brain region of interest.

It will be apparent to those skilled in the art that various modifications and variations can be made to the methods, software and systems of the present invention. The foregoing examples and figures are presented for purposes of illustration and description. It is not intended to be exhaustive or to limit the invention to the precise forms disclosed. Many modifications and variations will be apparent to practitioners skilled in this art and are intended to fall within the scope of the invention.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

What is claimed is:

1. A method comprising:
   (a) taking fMRI activity measurements of at least one localized region of a brain of a subject who is inside a fMRI scanner;
   (b) communicating a representation of said activity measurements to said subject using a computer executable logic; and
   (c) training said subject while inside said fMRI scanner to use said representation of said activity measurements to control said activity, wherein said representation is communicated in the form of presenting a display of said subject's level of success in modulating said activity in said brain to said subject.

2. The method of claim 1 wherein said representation is communicated in substantially real time.

3. The method of claim 1 wherein said at least one localized region is internal relative to the surface of said brain.

4. The method of claim 1 comprising taking said fMRI activity measurements of a plurality of different internal localized regions of interest.

5. The method of claim 1 wherein said representation is communicated via a graphical user interface.

6. The method of claim 1 wherein said representation is communicated in a form selected from the group consisting of physiological images of said subject's brain, matched anatomical images at the same level of section, 3-D reconstructions of either anatomy or physiological activation patterns, and both difference activity level images and statistical maps.

7. The method of claim 1 wherein said representation is communicated using virtual reality stimuli.

8. The method of claim 1 wherein modulating said activity modulates a sensation of experienced pain by said subject.

9. The method of claim 1 wherein said subject has depression.

10. The method of claim 1 wherein said subject has anxiety disorder.

11. The method of claim 1 wherein said subject has attention deficit hyperactivity disorder.

12. The method of claim 1 wherein said subject has brain injury.

13. The method of claim 1 wherein said subject has had a stroke.

14. The method of claim 1 wherein said subject has epilepsy.

15. The method of claim 1 wherein modulating said activity modulates the release of a neuromodulator.

16. The method of claim 15 wherein said neuromodulator is selected from dopamine, acetylcholine and serotonin, an endogenous opiate, adrenaline, and norepinephrine.

17. The method of claim 1 wherein said fMRI activity measurements include real time motion correction.

18. The method of claim 1 wherein said fMRI measurements are spatially registered to measurements made across days.

19. The method of claim 1 wherein said fMRI activity measurements include a spatial pattern comparison metric that compares a spatial pattern of activity in said at least one localized region with another spatial pattern.

20. The method of claim 1 wherein said subject further communicates with an operator by audio and/or video communication.

21. The method of claim 1 wherein a computer interface is provided that allows said subject to input information.

22. The method of claim 1 further comprising repeating said method across multiple training sessions.

23. The method of claim 1 wherein step (a) further comprises collecting volume data; and, pre-processing said volume data by at least one process selected from the group consisting of spatial smoothing, temporal filtering, slice time correction, transformation into standard coordinates, resampling of data, motion correction of data, and regression filtering.

24. The method of claim 1 wherein said subject suffers from pain.

25. The method of claim 1 wherein said subject suffers from substance abuse.

26. The method of claim 1 wherein said fMRI activity measurements are taken from an anatomically-defined region of interest.

27. The method of claim 1 wherein said fMRI activity measurements are taken from a physiologically-defined region of interest.

28. The method of claim 1 wherein said subject suffers from schizophrenia.

29. The method of claim 1 wherein said subject suffers from memory loss.

30. A method comprising:
(a) taking fMRI activity measurements of at least one localized region of a brain of a subject who is inside a fMRI scanner, wherein said fMRI activity measurement include real time motion correction;
(b) communicating information about changes in said level of said activity to said subject using a computer executable logic; and
(c) training said subject while inside said fMRI scanner to use said information about changes in said level of said activity to control said activity.

31. The method of claim 30 wherein said fMRI activity measurements are averaged from a plurality of fMRI image volumes.

32. The method of claim 30 comprising taking said fMRI activity measurements of a plurality of different internal localized regions of interest.

33. The method of claim 30 wherein said fMRI activity measurements include a comparison of activity metrics from different regions of interest.

34. The method of claim 30 wherein said fMRI activity measurements include a comparison of activity metrics from the same region of interest during different time points.

* * * * *